United States Patent
Behzadi et al.

(10) Patent No.: US 11,375,975 B2
(45) Date of Patent: Jul. 5, 2022

(54) QUANTITATIVE ASSESSMENT OF IMPLANT INSTALLATION

(71) Applicant: Kambiz Behzadi, Pleasanton, CA (US)

(72) Inventors: Kambiz Behzadi, Pleasanton, CA (US); Michael E. Woods, Brisbane, CA (US)

(73) Assignee: Kambiz Behzadi, Pleasanton, CA (US)

( * ) Notice: Subject to any disclaimer, the term of this patent is extended or adjusted under 35 U.S.C. 154(b) by 420 days.

(21) Appl. No.: 16/375,736

(22) Filed: Apr. 4, 2019

(65) Prior Publication Data

US 2020/0069280 A1   Mar. 5, 2020

Related U.S. Application Data

(63) Continuation-in-part of application No. 16/030,603, filed on Jul. 9, 2018, which is a continuation-in-part of application No. 15/716,533, filed on Sep. 27, 2017, now Pat. No. 11,109,802, which is a continuation-in-part of application No. 15/687,324, filed on Aug. 25, 2017, now Pat. No. 11,191,517, said
(Continued)

(51) Int. Cl.
| | |
|---|---|
| *A61B 7/00* | (2006.01) |
| *A61B 7/02* | (2006.01) |
| *A61F 2/34* | (2006.01) |
| *A61F 2/46* | (2006.01) |
| *A61B 90/00* | (2016.01) |

(52) U.S. Cl.
CPC ............ *A61B 7/023* (2013.01); *A61F 2/34* (2013.01); *A61F 2/468* (2013.01); *A61B 2090/064* (2016.02)

(58) Field of Classification Search
CPC combination set(s) only.
See application file for complete search history.

(56) References Cited

U.S. PATENT DOCUMENTS

| 1,455,621 A | 5/1923 | Joyner |
| 2,121,193 A | 6/1938 | Erich |
(Continued)

FOREIGN PATENT DOCUMENTS

| EP | 1433445 A1 | 6/2004 |
| WO | 2007096476 A2 | 8/2007 |
(Continued)

OTHER PUBLICATIONS

PCT International Search Report for International application No. PCT/US17/26417, dated Jul. 3, 2017.
(Continued)

*Primary Examiner* — Sameh R Boles
(74) *Attorney, Agent, or Firm* — Patent Law Offices Michael E. Woods; Michael E. Woods

(57) ABSTRACT

A system and method for quantitatively assessing a press fit value (and provide a mechanism to evaluate optimal quantitative values) of any implant/bone interface regardless the variables involved including bone site preparation, material properties of bone and implant, implant geometry and coefficient of friction of the implant-bone interface without requiring a visual positional assessment of a depth of insertion. The following description is presented to enable one of ordinary skill in the art to make and use the invention and is provided in the context of a patent application and its requirements.

14 Claims, 40 Drawing Sheets

Related U.S. Application Data application No. 16/030,603 is a continuation-in-part of application No. 15/284,091, filed on Oct. 3, 2016, now Pat. No. 10,441,244, said application No. 15/716,533 is a continuation-in-part of application No. 15/284,091, filed on Oct. 3, 2016, now Pat. No. 10,441,244, said application No. 15/687,324 is a continuation of application No. 15/284,091, filed on Oct. 3, 2016, now Pat. No. 10,441,244, which is a continuation-in-part of application No. 15/234,782, filed on Aug. 11, 2016, now Pat. No. 10,912,655, said application No. 15/716,533 is a continuation-in-part of application No. 15/234,782, filed on Aug. 11, 2016, now Pat. No. 10,912,655, which is a continuation-in-part of application No. 15/202,434, filed on Jul. 5, 2016, now abandoned, said application No. 15/716,533 is a continuation-in-part of application No. 15/202,434, filed on Jul. 5, 2016, now abandoned.

(60) Provisional application No. 62/743,042, filed on Oct. 9, 2018, provisional application No. 62/742,851, filed on Oct. 8, 2018, provisional application No. 62/651,077, filed on Mar. 31, 2018, provisional application No. 62/355,657, filed on Jun. 28, 2016, provisional application No. 62/353,024, filed on Jun. 21, 2016, provisional application No. 62/277,294, filed on Jan. 11, 2016.

(56) References Cited

U.S. PATENT DOCUMENTS

| | | |
|---|---|---|
| 3,818,514 A | 6/1974 | Clark |
| 3,874,003 A | 4/1975 | Moser et al. |
| 4,135,517 A | 1/1979 | Reale |
| 4,301,551 A | 11/1981 | Dore et al. |
| 4,457,306 A | 7/1984 | Borzone |
| 4,530,114 A | 7/1985 | Tepic |
| 4,608,019 A | 8/1986 | Kumabe et al. |
| 4,608,053 A | 8/1986 | Keller |
| 4,712,951 A | 12/1987 | Brown |
| 4,728,329 A | 3/1988 | Mansat |
| 5,108,400 A | 4/1992 | Appel et al. |
| 5,133,765 A | 7/1992 | Cuilleron |
| 5,318,570 A | 6/1994 | Hood et al. |
| 5,358,532 A | 10/1994 | Evans et al. |
| 5,431,657 A | 7/1995 | Rohr |
| 5,534,006 A | 7/1996 | Szabo et al. |
| 5,591,164 A | 1/1997 | Nazre et al. |
| 5,665,091 A | 9/1997 | Noble et al. |
| 5,693,088 A | 12/1997 | Lazarus |
| 5,702,473 A | 12/1997 | Albrektsson et al. |
| 5,713,901 A | 2/1998 | Tock |
| 5,769,092 A | 6/1998 | Williamson, Jr. |
| 5,806,518 A | 9/1998 | Mittelstadt |
| 5,849,015 A | 12/1998 | Haywood et al. |
| 5,980,528 A | 11/1999 | Salys |
| 6,048,365 A | 4/2000 | Burrows et al. |
| 6,110,179 A | 8/2000 | Flivik et al. |
| 6,146,425 A | 11/2000 | Hoermansdoerfer |
| 6,161,545 A | 12/2000 | Chow |
| 6,197,062 B1 | 3/2001 | Fenlin |
| 6,204,592 B1 | 3/2001 | Hur |
| 6,231,612 B1 | 5/2001 | Balay et al. |
| 6,585,771 B1 | 7/2003 | Buttermilch et al. |
| 7,036,211 B1 | 5/2006 | Panks |
| 7,645,281 B2 | 1/2010 | Marik |
| 7,875,083 B2 | 1/2011 | Sudmann |
| 8,167,823 B2 | 5/2012 | Nycz et al. |
| 8,328,849 B2 | 12/2012 | Nydegger et al. |
| 8,603,100 B2 | 12/2013 | Muller |
| 8,876,529 B2 | 11/2014 | Mayer et al. |
| 9,232,968 B2 | 1/2016 | Moumene et al. |
| 9,999,518 B2 | 6/2018 | Mani et al. |
| 10,251,663 B2 | 4/2019 | Behzadi |
| 10,299,930 B2 | 5/2019 | Behzadi |
| 10,849,766 B2 | 12/2020 | Behzadi |
| 10,864,083 B2 | 12/2020 | Behzadi |
| 10,905,456 B2 | 2/2021 | Behzadi |
| 10,912,655 B2 | 2/2021 | Behzadi et al. |
| 11,026,809 B2 | 6/2021 | Behzadi et al. |
| 2002/0082695 A1 | 6/2002 | Neumann |
| 2002/0183851 A1 | 12/2002 | Spiegelberg et al. |
| 2003/0065398 A1 | 4/2003 | Cueille et al. |
| 2003/0229357 A1 | 12/2003 | Dye |
| 2004/0019382 A1 | 1/2004 | Amirouche et al. |
| 2004/0044397 A1 | 3/2004 | Stinson |
| 2004/0097952 A1 | 5/2004 | Sarin et al. |
| 2005/0004680 A1 | 1/2005 | Saladino et al. |
| 2005/0015154 A1 | 1/2005 | Lindsey et al. |
| 2005/0101962 A1 | 5/2005 | Schwenke et al. |
| 2005/0154398 A1 | 7/2005 | Miniaci et al. |
| 2005/0209597 A1 | 9/2005 | Long et al. |
| 2006/0015110 A1 | 1/2006 | Pepper |
| 2006/0142754 A1 | 6/2006 | Irion et al. |
| 2006/0247638 A1 | 11/2006 | Trieu et al. |
| 2007/0005144 A1 | 1/2007 | Leisinger et al. |
| 2007/0162038 A1 | 7/2007 | Tuke |
| 2007/0219641 A1 | 9/2007 | Dorr et al. |
| 2007/0233131 A1 | 10/2007 | Song et al. |
| 2008/0091271 A1 | 4/2008 | Bonitati et al. |
| 2008/0109085 A1 | 5/2008 | Tulkis et al. |
| 2008/0234833 A1 | 9/2008 | Bandoh et al. |
| 2008/0255560 A1 | 10/2008 | Myers et al. |
| 2009/0112265 A1 | 4/2009 | Hudgins et al. |
| 2009/0192626 A1 | 7/2009 | Keefer et al. |
| 2009/0248083 A1 | 10/2009 | Patterson et al. |
| 2009/0292321 A1 | 11/2009 | Collette |
| 2010/0023014 A1 | 1/2010 | Romagnoli et al. |
| 2010/0249796 A1 | 9/2010 | Nycz |
| 2011/0004318 A1 | 1/2011 | Tulkis et al. |
| 2011/0178521 A1 | 7/2011 | Siravo et al. |
| 2011/0264009 A1 | 10/2011 | Walter et al. |
| 2012/0172939 A1 | 7/2012 | Pedicini |
| 2012/0209277 A1 | 8/2012 | Leparmentier et al. |
| 2013/0204264 A1 | 8/2013 | Mani et al. |
| 2013/0211535 A1 | 8/2013 | Cueille |
| 2013/0226189 A1 | 8/2013 | Young |
| 2013/0261762 A1 | 10/2013 | Kennedy |
| 2014/0012391 A1 | 1/2014 | Gugler et al. |
| 2014/0058526 A1 | 2/2014 | Meridew et al. |
| 2014/0128986 A1 | 5/2014 | Podolsky |
| 2014/0135773 A1 | 5/2014 | Stein et al. |
| 2014/0135791 A1 | 5/2014 | Nikou et al. |
| 2014/0207123 A1 | 7/2014 | Mueller |
| 2014/0257293 A1 | 9/2014 | Axelson, Jr. et al. |
| 2014/0303743 A1 | 10/2014 | Choudhury et al. |
| 2014/0330281 A1 | 11/2014 | Aghazadeh |
| 2014/0363481 A1 | 12/2014 | Pasini et al. |
| 2014/0370462 A1 | 12/2014 | Porter et al. |
| 2014/0371897 A1 | 12/2014 | Lin et al. |
| 2015/0182350 A1 | 7/2015 | Behzadi |
| 2015/0182351 A1 | 7/2015 | Behzadi |
| 2015/0196343 A1 | 7/2015 | Donald et al. |
| 2015/0201918 A1 | 7/2015 | Kumar et al. |
| 2015/0216668 A1 | 8/2015 | Smith |
| 2015/0282856 A1 | 10/2015 | Haiat et al. |
| 2016/0029952 A1* | 2/2016 | Hunter ............ A61B 5/0022 623/22.17 |
| 2016/0058519 A1 | 3/2016 | Herr |
| 2016/0166390 A1 | 6/2016 | Dye et al. |
| 2016/0206430 A1 | 7/2016 | Grostefon et al. |
| 2016/0206433 A1 | 7/2016 | Grostefon et al. |
| 2016/0220315 A1 | 8/2016 | Falardeau et al. |
| 2016/0338751 A1 | 11/2016 | Kellar et al. |
| 2017/0056205 A1 | 3/2017 | Biegun et al. |
| 2017/0196506 A1 | 7/2017 | Behzadi |
| 2017/0196701 A1 | 7/2017 | Behzadi et al. |
| 2017/0196704 A1 | 7/2017 | Behzadi et al. |
| 2017/0196705 A1 | 7/2017 | Behzadi |
| 2017/0196706 A1 | 7/2017 | Behzadi |
| 2017/0196707 A1 | 7/2017 | Behzadi |

(56) References Cited

U.S. PATENT DOCUMENTS

| | | |
|---|---|---|
| 2017/0196708 A1 | 7/2017 | Behzadi et al. |
| 2017/0196710 A1 | 7/2017 | Behzadi |
| 2017/0196711 A1 | 7/2017 | Behzadi |
| 2017/0290666 A1 | 10/2017 | Behzadi |
| 2017/0290667 A1 | 10/2017 | Behzadi |
| 2017/0325972 A1 | 11/2017 | Steif |
| 2017/0340448 A1 | 11/2017 | Behzadi |
| 2017/0340456 A1 | 11/2017 | Behzadi |
| 2017/0354505 A1 | 12/2017 | Behzadi |
| 2018/0049891 A1 | 2/2018 | Termanini |
| 2018/0235764 A1 | 8/2018 | Moore et al. |
| 2018/0235765 A1 | 8/2018 | Welker et al. |
| 2018/0296364 A1 | 10/2018 | Harris et al. |
| 2018/0325695 A1 | 11/2018 | Wozencroft |
| 2019/0336307 A1 | 11/2019 | Sungu et al. |
| 2020/0069279 A1 | 3/2020 | Behzadi et al. |
| 2020/0069280 A1 | 3/2020 | Behzadi et al. |
| 2020/0205988 A1 | 7/2020 | Behzadi et al. |
| 2020/0261232 A1 | 8/2020 | Mistry |
| 2020/0297499 A1 | 9/2020 | Behzadi et al. |

FOREIGN PATENT DOCUMENTS

| | | |
|---|---|---|
| WO | 2017029173 A1 | 2/2017 |
| WO | 2018031752 A1 | 2/2018 |

OTHER PUBLICATIONS

PCT Written Opinion of The International Searching Authority for International application No. PCT/US17/26417 dated Jul. 3, 2017.
International Search Report regarding International application No. PCT/US2017/037042 dated Oct. 6, 2017.
Written Opinion of the International Searching Authority regarding International application No. PCT/US2017/037042 dated Oct. 6, 2017.
International Search Report for International application No. PCT/US2017/012753, dated May 5, 2017.
Written Opinion of the International Searching Authority for International application No. PCT/US2017/012753 dated May 5, 2017.
International Search Report for International application No. PCT/US2017/046261, dated Oct. 18, 2017.
Written Opinion of the International Searching Authority for International application No. PCT/US2017/046261, dated Oct. 18, 2017.
U.S. Appl. No. 17/446,985, filed Sep. 7, 2021, Kambiz Behzadi.
U.S. Appl. No. 17/449,245, filed Sep. 28, 2021, Kambiz Behzadi.
U.S. Appl. No. 17/457,761, filed Dec. 6, 2021, Kambiz Behzadi.
U.S. Appl. No. 17/586,359, filed Jan. 27, 2022, Kambiz Behzadi.
U.S. Appl. No. 17/587,389, filed Jan. 28, 2022, Kambiz Behzadi.
U.S. Appl. No. 17/587,835, filed Jan. 28, 2022, Kambiz Behzadi et al.
U.S. Appl. No. 17/588,793, filed Jan. 31, 2022, Kambiz Behzadi.
U.S. Appl. No. 62/277,294, filed Jan. 11, 2016, Kambiz Behzadi.
U.S. Appl. No. 62/353,024, filed Jun. 21, 2016, Kambiz Behzadi.
U.S. Appl. No. 62/355,657, filed Jun. 28, 2016, Kambiz Behzadi.
U.S. Appl. No. 62/373,515, filed Aug. 11, 2016, Kambiz Behzadi.
U.S. Appl. No. 62/651,077, filed Mar. 31, 2018, Kambiz Behzadi.
U.S. Appl. No. 62/742,851, filed Oct. 8, 2018, Kambiz Behzadi.
U.S. Appl. No. 62/743,042, filed Oct. 9, 2018, Kambiz Behzadi et al.
U.S. Appl. No. 15/202,434, filed Jul. 5, 2016, Kambiz Behzadi.
U.S. Appl. No. 15/234,782, filed Aug. 11, 2016, Kambiz Behzadi et al.
U.S. Appl. No. 15/234,880, filed Aug. 11, 2016, Kambiz Behzadi et al.
U.S. Appl. No. 15/235,032, filed Aug. 11, 2016, Kambiz Behzadi et al.
U.S. Appl. No. 15/235,053, filed Aug. 11, 2016, Kambiz Behzadi.
U.S. Appl. No. 15/284,091, filed Oct. 3, 2016, Kambiz Behzadi.
U.S. Appl. No. 15/362,675, filed Nov. 28, 2016, Kambiz Behzadi.
U.S. Appl. No. 15/396,785, filed Jan. 2, 2017, Kambiz Behzadi et al.
U.S. Appl. No. 15/398,996, filed Jan. 5, 2017, Kambiz Behzadi.
U.S. Appl. No. 15/453,219, filed Mar. 8, 2017, Kambiz Behzadi.
U.S. Appl. No. 15/592,229, filed May 11, 2017, Kambiz Behzadi.
U.S. Appl. No. 15/687,324, filed Aug. 25, 2017, Kambiz Behzadi.
U.S. Appl. No. 15/716,529, filed Sep. 27, 2017, Kambiz Behzadi et al.
U.S. Appl. No. 15/716,533, filed Sep. 27, 2017, Kambiz Behzadi.
U.S. Appl. No. 16/030,603, filed Jul. 9, 2018, Kambiz Behzadi.
U.S. Appl. No. 16/030,824, filed Jul. 9, 2018, Kambiz Behzadi.
U.S. Appl. No. 16/154,033, filed Oct. 8, 2018, Kambiz Behzadi et al.
U.S. Appl. No. 16/276,639, filed Feb. 15, 2019, Kambiz Behzadi.
U.S. Appl. No. 16/278,085, filed Feb. 16, 2019, Kambiz Behzadi.
U.S. Appl. No. 16/278,668, filed Feb. 18, 2019, Kambiz Behzadi.
U.S. Appl. No. 16/374,750, filed Apr. 4, 2019, Kambiz Behzadi et al.
U.S. Appl. No. 16/571,180, filed Sep. 15, 2019, Kambiz Behzadi.
U.S. Appl. No. 16/586,960, filed Sep. 28, 2019, Kambiz Behzadi.
U.S. Appl. No. 16/589,099, filed Sep. 30, 2019, Kambiz Behzadi.
U.S. Appl. No. 16/595,341, filed Oct. 7, 2019, Kambiz Behzadi.
U.S. Appl. No. 16/596,410, filed Oct. 8, 2019, Kambiz Behzadi et al.
U.S. Appl. No. 16/819,092, filed Mar. 14, 2020, Kambiz Behzadi et al.
U.S. Appl. No. 16/842,415, filed Apr. 7, 2020, Kambiz Behzadi.
U.S. Appl. No. 16/945,908, filed Aug. 2, 2020, Kambiz Behzadi et al.
U.S. Appl. No. 17/010,769, filed Sep. 2, 2020, Kambiz Behzadi et al.
U.S. Appl. No. 17/164,780, filed Feb. 1, 2021, Kambiz Behzadi.
U.S. Appl. No. 17/238,148, filed Apr. 22, 2021, Kambiz Behzadi.

* cited by examiner

QUANTITATIVE ASSESSMENT OF IMPLANT INSTALLATION

CROSS REFERENCE TO RELATED APPLICATIONS

This application claims the benefit of U.S. Provisional Application 62/743,042 filed on Oct. 9, 2018. This application claims the benefit of U.S. Provisional Application 62/742,851 filed on Oct. 8, 2018. This application is a Continuation-in-part of application Ser. No. 16/030,603 filed on Jul. 9, 2018. Application Ser. No. 16/030,603 claims the benefit of U.S. Provisional Application 62/651,077 filed on Mar. 31, 2018. Application Ser. No. 16/030,603 is a Continuation-in-part of application Ser. No. 15/716,533 filed on Sep. 27, 2017. Application Ser. No. 15/716,533 is a Continuation-in-part of application Ser. No. 15/687,324 filed on Aug. 25, 2017. Application Ser. No. 15/687,324 is a Continuation of application Ser. No. 15/284,091 filed on Oct. 3, 2016. Application Ser. No. 15/284,091 is a Continuation-in-part of application Ser. No. 15/234,782 filed on Aug. 11, 2016. Application Ser. No. 15/234,782 is a Continuation-in-part of application Ser. No. 15/202,434 filed on Jul. 5, 2016. Application Ser. No. 15/202,434 claims the benefit of U.S. Provisional Application 62/277,294 filed on Jan. 11, 2016. Application Ser. No. 15/234,782 claims the benefit of U.S. Provisional Application 62/355,657 filed on Jun. 28, 2016. Application Ser. No. 15/234,782 claims the benefit of U.S. Provisional Application 62/353,024 filed on Jun. 21, 2016. Application Ser. No. 15/716,533 is a Continuation-in-part of application Ser. No. 15/284,091 filed on Oct. 3, 2016. Application Ser. No. 15/716,533 is a Continuation-in-part of application Ser. No. 15/234,782 filed on Aug. 11, 2016. Application Ser. No. 15/716,533 is a Continuation-in-part of application Ser. No. 15/202,434 filed on Jul. 5, 2016. Application Ser. No. 16/030,603 is a Continuation-in-part of application Ser. No. 15/284,091 filed on Oct. 3, 2016. All of the these identified applications, including direct and indirect parent applications, are hereby expressly incorporated by reference thereto in their entireties for all purposes.

FIELD OF THE INVENTION

The present invention relates generally to assessing a quality of an installation of an implant structure installed in a body, and more specifically, but not exclusively, to quantitative assessment of prosthesis press-fit fixation into a bone cavity, for example, assessment of press-fit fixation of an acetabular cup into a prepared (e.g., relatively under-reamed acetabulum) bone cavity, assessment of connective tissue installation and repair.

BACKGROUND OF THE INVENTION

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

Initial stability of metal backed acetabular components is an important factor in an ultimate success of cement-less hip replacement surgery. The press fit technique, which involves impaction of an oversized (relative to a prepared cavity in an acetabulum) porous coated acetabular cup into an undersized cavity (relative to the prosthesis to be installed) of bone produces primary stability through cavity deformation and frictional forces, and has shown excellent long term results. This press fit technique avoids use of screw fixation associated with risk of neurovascular injury, fretting and metallosis, and egress of particulate debris and osteolysis.

However, it has been difficult to assess a primary implant stability due to complex nature of bone-implant interface, or to evaluate an optimal press fit fixation. The initial interaction of the implant with bone is due the circumferential surface interference at the aperture transitioning to compression of the cavity with deeper insertion. A compromise exists between seating the cup enough to get sufficient primary stability and avoiding fracture of bone. There is no quantitative method in current clinical practice to assess the primary stability of the implant, with surgeons relying solely on their qualitative proprioceptive senses (tactile, auditory, and visual) to determine point of optimal press fit fixation.

Four factors associated with difficulty obtaining optimal press fit fixation: i) no current method exists to gauge the resulting stress field in bone during the impaction of an oversized implant; ii) the material properties of bone (bone density) vary significantly based on age and sex of the patient, and are unknown to the surgeon; iii) current mallet based techniques for impaction do not allow surgeons to control (quantify and increment) the magnitude of force using in installation; and iv) surgeons are charged with the difficult task of: a) applying and modulating magnitude of force; b) deciding when to stop application of force; and c) assessing a quality of press fit fixation all simultaneously in their "mind's eye" during the process of impaction.

A significance of this problem on patients, medical practice and economy is great. Although Total Hip Replacement (THR) is widely recognized as a successful operation, 3 to 25% of operations fail requiring revision surgery. Aseptic loosening of press fit THR components is one of the most common causes of failure at 50% to 90% and closely associated with insufficient initial fixation. Inadequate stabilization may lead to late presentation of aseptic loosening due to formation of fibrous tissue and over stuffing the prosthesis may lead to occult and/or frank peri-prosthetic fractures. The cost of poor initial press fit fixation resulting from (loosening, occult fractures, subsidence, fretting, metallosis, and infections) maybe under reported however estimated to be in tens of billions of dollars. Over 400,000 total hip replacements are done in US every year, over 80% of which are done by surgeons who do less than ten per year. The limitations of this procedure produce frustration and anxiety for surgeons, physical and emotional pain for patients, at great costs to society.

Initial implant fixation can be measured by pullout, lever out, and torsional test in vitro; however, these methods have minimal utility in a clinical setting in that they are destructive. Vibration analysis, where secure and loose implants can be distinguished by the differing frequency responses of the implant bone interface, has been successfully employed in evaluating fixation of dental implants however, this technology has not been easily transferable to THR surgery, and currently has no clinical utility.

In clinical practice, surgeons err on the side of not overstuffing the prosthesis which leads to a smaller under ream (or line to line ream) and screw fixation with attendant risks.

Finally, several visual tracking methods (Computer Navigation, Fluoroscopy, MAKO Robotics) are utilized to assess the depth of cup insertion during impaction in order to guide application of force; however, these techniques, from and engineering perspective, are considered to be open loop, where the feedback response to the surgeon is not a force (sensory) response, and therefore does not provide any information about the stress response of the cavity.

Injury to connective tissue is common, particularly for those that are physically active. A common type of injury among certain sports and activities is the ACL injury. A healing potential of a ruptured ACL has been poor, and reconstruction of the ACL is often required for return to activity and sports. Various types of tendon grafts are used to reconstruct the ACL including allograft and autograft tissues. In general, bony tunnels are created in the tibia and femur and a variety of fixation devices are used to fix a graft that has been pulled into the knee joint, within the tunnels, to the tibia and femur. Various types of fixation are utilized to fix the graft to the bone tunnels. These fixation methods broadly categorized into cortical suspensory button fixation vs. aperture interference screw fixation.

A system and method are needed to quantitatively assess a press fit value (and provide a mechanism to evaluate optimal quantitative values) of any implant/bone interface regardless the variables involved including bone site preparation, material properties of bone and implant, implant geometry and coefficient of friction of the implant-bone interface without requiring a visual positional assessment of a depth of insertion.

What is needed is a solution that improves connective tissue repair options while reducing disadvantages.

BRIEF SUMMARY OF THE INVENTION

Disclosed is a system and method for quantitatively assessing a press fit value (and provide a mechanism to evaluate optimal quantitative values) of any implant/bone interface regardless the variables involved including bone site preparation, material properties of bone and implant, implant geometry and coefficient of friction of the implant-bone interface without requiring a visual positional assessment of a depth of insertion.

Also disclosed is a system and method for an improved connective tissue repair option that reduces disadvantages of conventional fixation options. The following summary of the invention is provided to facilitate an understanding of some of the technical features related to connective tissue preparation and repair systems and methods, and is not intended to be a full description of the present invention. A full appreciation of the various aspects of the invention can be gained by taking the entire specification, claims, drawings, and abstract as a whole. The present invention is applicable to other connective tissue repair systems and methods in addition to repair of an anterior cruciate ligament (ACL) injury including other connective tissue repairs using a suspensory-type or aperture-type solution.

The following summary of the invention is provided to facilitate an understanding of some of the technical features related to installation of an acetabular cup prosthesis into a relatively undersized prepared cavity in an acetabulum, and is not intended to be a full description of the present invention. A full appreciation of the various aspects of the invention can be gained by taking the entire specification, claims, drawings, and abstract as a whole. The present invention is applicable to other press fit fixation systems, including installation of different prostheses into different locations, and installation of other structures into an elastic substrate.

Some embodiments of the proposed technology may enable a standardization of: a) application of force; and b) assessment of quality of fixation in joint replacement surgery, such that surgeons of all walks of life, whether they perform five or 500 hip replacements per year, will produce consistently superior/optimum/perfect results with respect to press fit fixation of implants in bone.

From the surgeon perspective this standardization process will level the playing field between the more and less experienced surgeons, leading to less stress and anxiety for the surgeons affecting their mental wellness. From the patient perspective there will be a decrease in the number of complications and ER admissions leading to decrease in morbidity and mortality. From an economic perspective there will be a significant cost savings for the government and insurance companies due to a decrease in the number of readmissions and revision surgery's, particularly since revision surgery in orthopedics accounts for up to 30% of a 50-billion-dollar industry.

To address this deficiency, some embodiments and related applications have considered a novel means of accessing and processing various force responses of bone (Invasive Sensing Mechanism) and propose that this mechanism can guide application of force to the bone cavity, to obtain optimal press fit technologically without reliance on surgeon's proprioception. There are several possible outcomes of this proposal, if validated, including that it may make joint replacement surgery a significantly safer operation leading to less morbidity and complications, readmissions, and revision surgery; resulting in great benefits to patients, surgeons and society in general.

An embodiment of the present invention may include a series of operations for installing a prosthesis into a relatively undersized cavity prepared in a portion of bone, including communicating, using an installation agency, a quantized applied force to a prosthesis being press-fit into the cavity; monitoring a rigidity metric and an elasticity metric of the prosthesis with respect to the cavity (some embodiments do this in real-time or near real-time without requiring imaging or position-determination technology); further processing responsive to the rigidity and elasticity metrics, including continuing to install the prosthesis at present level of applied force while monitoring the metrics when the metrics indicate that installation change is acceptable and a risk of fracture remains at an acceptable level, increasing the applied force and continuing applying the installation agency while monitoring the metrics when the metrics indicate that installation change is minimal and a risk of fracture remains at an acceptable level, or suspending operation of the installation agency when the metrics indicate that installation change is minimal when a risk of fracture increases to an unacceptable level. Some embodiments may determine rigidity/elasticity from position, or vibration spectrum in air (sound) or bone. In some embodiments, while rigidity and elasticity may be determined in several different ways, some of which are disclosed herein, some implementations may determine a quantitative assessment responsive to evaluations of both responsive rigidity and elasticity factors during controlled operation of an insertion agency communicating an application force to a prosthesis (best fixation short of fracture—BFSF). BFSF may be related to one or both of these rigidity and elasticity factors.

An apparatus for insertion of a prosthesis into a cavity formed in a portion of bone, the prosthesis relatively oversized with respect to the cavity, including an insertion device providing an insertion agency to the prosthesis, the insertion agency operating over a period, the period including an initial prosthesis insertion act with the insertion device and a subsequent prosthesis insertion act with the insertion device; and a system physically coupled to the insertion device configured to provide a parametric evaluation of an extractive force of an interface between the prosthesis and the cavity during the period, the parametric evaluation including an evaluation of a set of factors of the prosthesis with respect to the cavity, the set of factors including one or more of a rigidity factor, an elasticity factor, and a combination of the rigidity factor and the elasticity factor.

A method for an insertion of an implant into a cavity in a portion of bone, the cavity relatively undersized with respect to the implant, including a) providing, using a device, an implant insertion agency to the implant to transition the implant toward a deepen insertion into the cavity; and b) predicting, responsive to the implant insertion agency, a press-fit fixation of the implant at an interface between the implant and the cavity during the providing of the implant insertion agency.

An impact control method for installing an implant into a cavity in a portion of bone, the cavity relatively undersized with respect to the implant, including a) imparting a first initial known force to the implant; b) imparting a first subsequent known force to the implant, the first subsequent known force about equal to the first initial force; c) measuring, for each the imparted known force, an Xth number measured impact force; d) comparing the Xth measured impact force to the Xth-1 measured impact force against a predetermined threshold for a threshold test; and e) repeating steps b)-d) as long as the threshold test is negative.

A method for an automated installation of an implant into a cavity in a portion of bone, including a) initiating an application of an installation agency to the implant, the installation agency including an energy communicated to the implant moving the implant deeper into the cavity in response thereto; b) recording a set of measured response forces responsive to the installation agency; c) continuing applying and recording until a difference in successive measured responses is within a predetermined threshold to estimate no significant displacement of the implant at the energy as the implant is installed into the cavity; d) increasing the energy; e) repeating steps b)-c) until a plateau of the set of the measured response forces; and f) terminating steps b)-e) when a steady-state is detected.

A method for insertion of a prosthesis into a cavity formed in a portion of bone, the prosthesis relatively oversized with respect to the cavity, including a) applying an insertion agency to the prosthesis, the insertion agency operating over a period, the period including an initial prosthesis insertion act with the insertion device and a subsequent prosthesis insertion act with the insertion device; and b) providing a parametric evaluation of an extractive force of an interface between the prosthesis and the cavity during the period, the parametric evaluation including an evaluation of a set of factors of the prosthesis with respect to the cavity, the set of factors including one or more of a rigidity factor, an elasticity factor, and a combination of the rigidity factor and the elasticity factor.

An apparatus for installing a prosthesis into a relatively undersized prepared cavity in a portion of a bone, including a force applicator operating an insertion agency for installing the prosthesis into the cavity; a force transfer structure, coupled to the force applicator and to the prosthesis, for conveying an application force F1 to the prosthesis, the application force F1 derived from the insertion agency; a force sensing system determining a force response of the prosthesis at an interface of the prosthesis and the cavity, the force response responsive to the application force F1; and a controller, coupled to force applicator and to the force sensing system, the controller setting an operational parameter for the insertion agency, the operational parameter establishing the application force F1, the controller responsive to the force response to establish a set of parameters including one or more of a rigidity metric, an elasticity metric, and combinations thereof.

A method for installing a prosthesis into a relatively undersized cavity prepared in a portion of bone, including a) communicating an application force F1 to the prosthesis; b) monitoring a rigidity factor and an elasticity factor of the prosthesis within the cavity during application of the application force F1; c) repeating a)-b) until the rigidity factor meets a first predetermined goal; d) increasing, when the rigidity factor meets the predetermined goal, the application force F1; e) repeating a)-d) until the elasticity factor meets a second predetermined goal; and f) suspending a) when the elasticity factor meets the first goal and the rigidity factor meets the second goal.

An acetabular cup for a prepared cavity in a portion of bone, including a generally hemispherical exterior shell portion defining a generally hemispherical interior cavity; and a snubbed polar apex portion of the generally hemispherical exterior shell portion without degradation of the generally hemispherical interior cavity producing a polar gap within the prepared cavity when fully seated.

An implant for a prepared cavity in a portion of bone, including an exterior shell portion having an interior cavity; and a snubbed polar apex portion of the exterior shell portion without degradation of the interior cavity producing a polar gap within the prepared cavity when fully seated.

An apparatus for insertion of a prosthesis into a cavity formed in a portion of bone, the prosthesis relatively oversized with respect to the cavity, including means for applying an insertion agency to the prosthesis, the insertion agency operating over a period, the period including an initial prosthesis insertion act with the insertion device and a subsequent prosthesis insertion act with the insertion device; and means, physically coupled to the insertion device, for determining a parametric evaluation of an extractive force of an interface between the prosthesis and the cavity during the period, the parametric evaluation including an evaluation of a set of factors of the prosthesis with respect to the cavity, the set of factors including one or more of a rigidity factor, an elasticity factor, and a combination of the rigidity factor and the elasticity factor.

An embodiment may include a graft platform (e.g., a table or stage) that is specially configured for pre-repair preparation of a connective tissue graft. This structure temporarily compresses and/or tensions (e.g., stretches) the connective tissue graft which temporarily reduces its outer perimeter (e.g., for a circular graft this may refer to a radius/circumference of the graft) appropriately in advance of installation. After installation, the connective tissue graft naturally expands towards its original unreduced perimeter in situ which may apply high compressive forces at a ligament/bone interface within bone tunnels through, or into, which the reduced graft had been installed.

An embodiment for a graft platform includes a graft compression system. A graft compression system may be implemented in many different ways—it may include a support for a pair of stages that may be coupled together via an optional controllable separation mechanism that controls a distance between these stages. Each stage may include a gripping system that provides compression to reduce and/or profile the perimeter. The compression system may include one or both of these compressive mechanisms: (a) grip and stretch, and/or (b) grip and squeeze.

This may increase the possibility of the more natural "direct-type" tendon to bone healing which decreases risks of repair failures that arise from "indirect-type" healing.

This may allow a surgeon to use repair procedures that preserve more bone. These procedures often include preparing the tunnels in the bone and allowing for use of a reduced perimeter graft allows the surgeon to prepare smaller radius tunnels or to improve graft repair strength of conventionally-sized tunnels, at the surgeon's discretion. More options allow the surgeon to provide better customized solutions to the patience.

An embodiment of the present invention may include a graft-preparation table that includes a pair of relatively-moveable stages (e.g., a distance between these stages is variable). Each stage may be provided with a compressive structure that secures the graft. The stage may compress the graft by direct compression through application of force(s) on the perimeter and/or indirect compression by tensioning the graft such as by stretching the graft through pulling.

Method and Apparatus Claims for creation of Non-cylindrical, asymmetric, conical, frustum like, profiled, curvilinear tunnels for ACL reconstruction (as well as other ligaments in other joints), in which a natural mechanical resistance to pull out is produced for a decompressing and/or expanding compressed connective tissue graft by the inherent asymmetric shape of the tunnel (A) using existing 3D sculpting or existing robotic techniques and/or new bone preparation techniques.

Method and Apparatus for creation of ACL (PCL, MPFL, MCL, LCL) ligament bone tunnels without the use of a pre-determined guide wire and over drilling technique.

Method and Apparatus for correlating precisely or matching precisely (e.g., to within 1mm) the length of ACL graft with the length of bony tunnels+intra articular ACL, when using robotic or 3D bone sculpting techniques, instead of guide wire and over drill techniques.

Method and Apparatus for producing the environment which allows a "biologic press fit" fixation, where high tendon-bone interface forces are achieved with a passively or actively decompressing/expanding (previously compressed) ACL graft, which may be used with or without suspensory cortical fixation and with or without mechanical foreign body (e.g., screw-less) fixation.

Method and Apparatus for delivery of various biological growth factors within a compressed ACL graft to enhance tendon bone healing with direct type and/or indirect type healing at the interface (angiogenesis and osteogenesis) with or without suspensory cortical fixation and with or without mechanical foreign body (e.g., screw-less) fixation.

Method and Apparatus for embedding sensors (biologic and/or electronic) within the substance of ACL (and other ligament) grafts to assess (A) intra-tunnel interface forces (pressures), in order to determine if/when interface forces are adequate (high) enough for direct type and/or indirect type healing (B) intra-articular ligament tensile and shear forces (within the notch) to determine failure mechanisms and maximal load to failure in the case of re injury or re rupture.

Method and Apparatus for pre-compressing and shipping pre-compressed connective tissue graft, including use of a sheathing system having one or more layers, those layers may include: structural elements to maintain compression until pre-operative preparation; time-delaying materials/ construction for manipulation of active/passive decompression/expansion; inclusion of biologic sensors; and/or inclusion of biologic growth/healing/bone or tissue conditioning factors to promote a desired outcome with the installation of the decompressing/expanding compressed graft within a prepared bone tunnel.

Method and Apparatus for embedding a set of one or more prosthetic elements inside a connective tissue graft (conventional or pre-compressed) and securing/deploying/installing a prosthetically-enhanced natural connective tissue within a prepared bone tunnel for fixation, the fixation may include the passive/active decompression/expansion of a pre-compressed prosthetically-enhanced connective tissue graft, the enhancement including a set of one or more natural, synthetic, and/or hybrid materials having a material property different from natural connective tissue.

Method and Apparatus for deploying expansion structures within a natural connective tissue graft, initiating and manipulating enlargement of those expansion structures to actively expand the natural connective tissue graft; and including a prosthetic element, such as described in claim 8, as part of or cooperative with the deployed expansion structures.

Any of the embodiments described herein may be used alone or together with one another in any combination. Inventions encompassed within this specification may also include embodiments that are only partially mentioned or alluded to or are not mentioned or alluded to at all in this brief summary or in the abstract. Although various embodiments of the invention may have been motivated by various deficiencies with the prior art, which may be discussed or alluded to in one or more places in the specification, the embodiments of the invention do not necessarily address any of these deficiencies. In other words, different embodiments of the invention may address different deficiencies that may be discussed in the specification. Some embodiments may only partially address some deficiencies or just one deficiency that may be discussed in the specification, and some embodiments may not address any of these deficiencies.

Other features, benefits, and advantages of the present invention will be apparent upon a review of the present disclosure, including the specification, drawings, and claims.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

FIG. 11 illustrates a comparison of F5 to F1;

FIG. 12 illustrates a comparison of ΔF5 to a predetermined threshold (e.g., 0.0);

FIG. 13 illustrates a comparison of F2 to F1;

FIG. 14 illustrates a comparison of ΔF2 to a predetermined threshold (e.g., 0.0);

FIG. 29 illustrates pre-expansion of a compressed ACL graft;

FIG. 30 illustrates a post-expansion of the compressed ACL graft;

FIG. 31 illustrates pre-expansion of a compressed ACL graft;

FIG. 32 illustrates a post-expansion of the compressed ACL graft;

FIG. 38 illustrates a general biosensor;

FIG. 39 illustrates a point-of-care (PI-POCT) diagnostic device;

FIG. 40 illustrates an implementation of force/displacement sensing with interference fit fixation;

FIG. 41 illustrates an implementation of an aseptic loosening sensing, linear variable displacement transformers (LVDT), with interference fit fixation;

FIG. 42 illustrates a biosensor integrated microelectronic sensor;

FIG. 43 illustrates a sensing system for assessing metallosis and trunnionosis;

FIG. 44 illustrates a sensing system for assessing optimal press fit in ligament reconstruction;

FIG. 45 illustrates a sensing system for assessing poor healing of a reconstructed ligaments;

FIG. 46 illustrates a sensing system for assessing various failure modes of a reconstructed ligament grafts;

DETAILED DESCRIPTION OF THE INVENTION

Figure 1:
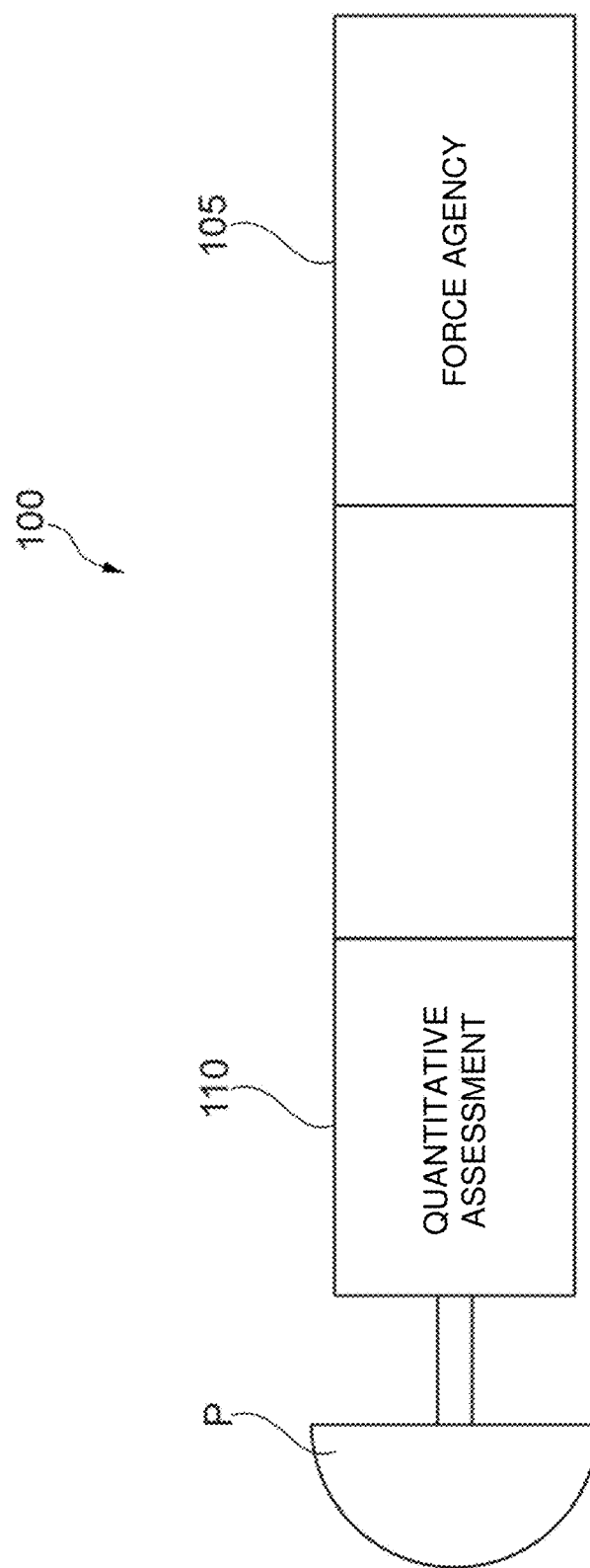
FIG. 1 illustrates a smart tool for prosthesis installation.

Embodiments of the present invention provide a system and method for quantitatively assessing a press fit value (and provide a mechanism to evaluate optimal quantitative values) of any implant/bone interface regardless the variables involved including bone site preparation, material properties of bone and implant, implant geometry and coefficient of friction of the implant-bone interface without requiring a visual positional assessment of a depth of insertion. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

Definitions

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The following definitions apply to some of the aspects described with respect to some embodiments of the invention. These definitions may likewise be expanded upon herein.

As used herein, the term "or" includes "and/or" and the term "and/or" includes any and all combinations of one or more of the associated listed items. Expressions such as "at least one of," when preceding a list of elements, modify the entire list of elements and do not modify the individual elements of the list.

As used herein, the singular terms "a," "an," and "the" include plural referents unless the context clearly dictates otherwise. Thus, for example, reference to an object can include multiple objects unless the context clearly dictates otherwise.

Also, as used in the description herein and throughout the claims that follow, the meaning of "in" includes "in" and "on" unless the context clearly dictates otherwise. It will be understood that when an element is referred to as being "on" another element, it can be directly on the other element or intervening elements may be present therebetween. In contrast, when an element is referred to as being "directly on" another element, there are no intervening elements present.

As used herein, the term "set" refers to a collection of one or more objects. Thus, for example, a set of objects can include a single object or multiple objects. Objects of a set also can be referred to as members of the set. Objects of a set can be the same or different. In some instances, objects of a set can share one or more common properties.

As used herein, the term "adjacent" refers to being near or adjoining. Adjacent objects can be spaced apart from one another or can be in actual or direct contact with one another. In some instances, adjacent objects can be coupled to one another or can be formed integrally with one another.

As used herein, the terms "connect," "connected," and "connecting" refer to a direct attachment or link. Connected objects have no or no substantial intermediary object or set of objects, as the context indicates.

As used herein, the terms "couple," "coupled," and "coupling" refer to an operational connection or linking. Coupled objects can be directly connected to one another or can be indirectly connected to one another, such as via an intermediary set of objects.

The use of the term "about" applies to all numeric values, whether or not explicitly indicated. This term generally refers to a range of numbers that one of ordinary skill in the art would consider as a reasonable amount of deviation to the recited numeric values (i.e., having the equivalent function or result). For example, this term can be construed as including a deviation of ±10 percent of the given numeric value provided such a deviation does not alter the end function or result of the value. Therefore, a value of about 1% can be construed to be a range from 0.9% to 1.1%.

As used herein, the terms "substantially" and "substantial" refer to a considerable degree or extent. When used in conjunction with an event or circumstance, the terms can refer to instances in which the event or circumstance occurs precisely as well as instances in which the event or circumstance occurs to a close approximation, such as accounting for typical tolerance levels or variability of the embodiments described herein.

As used herein, the terms "optional" and "optionally" mean that the subsequently described event or circumstance may or may not occur and that the description includes instances where the event or circumstance occurs and instances in which it does not.

As used herein, the term "bone" means rigid connective tissue that constitute part of a vertebral skeleton, including mineralized osseous tissue, particularly in the context of a living patient undergoing a prosthesis implant into a portion of cortical bone. A living patient, and a surgeon for the patient, both have significant interests in reducing attendant risks of conventional implanting techniques including fracturing/shattering the bone and improper installation and positioning of the prosthesis within the framework of the patient's skeletal system and operation.

As used herein, the term "size" refers to a characteristic dimension of an object. Thus, for example, a size of an object that is spherical can refer to a diameter of the object. In the case of an object that is non-spherical, a size of the non-spherical object can refer to a diameter of a corresponding spherical object, where the corresponding spherical object exhibits or has a particular set of derivable or measurable properties that are substantially the same as those of the non-spherical object. Thus, for example, a size of a non-spherical object can refer to a diameter of a corresponding spherical object that exhibits light scattering or other properties that are substantially the same as those of the non-spherical object. Alternatively, or in conjunction, a size of a non-spherical object can refer to an average of various orthogonal dimensions of the object. Thus, for example, a size of an object that is a spheroidal can refer to an average of a major axis and a minor axis of the object. When referring to a set of objects as having a particular size, it is contemplated that the objects can have a distribution of sizes around the particular size. Thus, as used herein, a size of a set of objects can refer to a typical size of a distribution of sizes, such as an average size, a median size, or a peak size.

As used herein, the term "mallet" or "hammer" or similar refers to an orthopedic device made of stainless steel or other dense material having a weight generally a carpenter's hammer and a stonemason's lump hammer.

As used herein, the term "impact force" for impacting an acetabular component (e.g., an acetabular cup prosthesis) includes forces from striking an impact rod multiple times with the orthopedic device that are generally similar to the forces that may be used to drive a three inch nail into a piece of lumber using the carpenter's hammer by striking the nail approximately a half-dozen times to completely seat the nail. Without limiting the preceding definition, a representative value in some instances includes a force of approximately 10 lbs./square inch.

As used herein, the term "realtime" sensing means sensing relevant parameters (e.g., force, acceleration, vibration, acoustic, and the like) during processing (e.g., installation, reaming, cutting) without stopping or suspending processing for visual evaluation of insertion depth of a prosthesis into a prepared cavity.

As used herein, the term "implant" means, unless the context clearly indicates otherwise, an expansive collection of structures designed and intended to be installed into tissue or bone of a body such as a living body or cadaver and includes prostheses, implants, grafts, and the like.

The following description relates to improvements in a wide-range of prostheses installations into live bones of patients of surgeons. The following discussion focuses primarily on total hip replacement (THR) in which an acetabular cup prosthesis is installed into the pelvis of the patient. This cup is complementary to a ball and stem (i.e., a femoral prosthesis) installed into an end of a femur engaging the acetabulum undergoing repair.

Embodiments of the present invention may include one of more solutions to the above problems. U.S. Pat. No. 9,168, 154, expressly incorporated by reference thereto in its entirety for all purposes, includes a description of several embodiments, sometimes referred to herein as a BMD3 device, some of which illustrate a principle for breaking down large forces associated with the discrete blows of a mallet into a series of small taps, which in turn perform similarly in a stepwise fashion while being more efficient and safer. The BMD3 device produces the same displacement of the implant without the need for the large forces from the repeated impacts from the mallet. The BMD3 device may allow modulation of force required for cup insertion based on bone density, cup geometry, and surface roughness. Further, a use of the BMD3 device may result in the acetabulum experiencing less stress and deformation and the implant may experience a significantly smoother sinking pattern into the acetabulum during installation. Some embodiments of the BMD3 device may provide a superior approach to these problems, however, described herein are two problems that can be approached separately and with more basic methods as an alternative to, or in addition to, a BMD3 device. An issue of undesirable torques and moment arms is primarily related to the primitive method currently used by surgeons, which involves manually banging the mallet on the impaction plate. The amount of force utilized in this process is also non-standardized and somewhat out of control.

With respect to the impaction plate and undesirable torques, an embodiment of the present invention may include a simple mechanical solution as an alternative to some BMD3 devices, which can be utilized by the surgeon's hand or by a robotic machine. A direction of the impact may be directed or focused by any number of standard techniques (e.g., A-frame, C-arm or navigation system). Elsewhere described herein is a refinement of this process by considering directionality in the reaming process, in contrast to only considering it just prior to impaction. First, we propose to eliminate the undesirable torques by delivering the impacts by a sledgehammer device or a (hollow cylindrical mass) that travels over a stainless rod.

As noted in the background, the surgeon prepares the surface of the hipbone which includes attachment of the acetabular prosthesis to the pelvis. Conventionally, this attachment includes a manual implantation in which a mallet is used to strike a tamp that contacts some part of the acetabular prosthesis. Repeatedly striking the tamp drives the acetabular prosthesis into the acetabulum. Irrespective of whether current tools of computer navigation, fluoroscopy, robotics (and other intra-operative measuring tools) have been used, it is extremely unlikely that the acetabular prosthesis will be in the correct orientation once it has been seated to the proper depth by the series of hammer strikes. After manual implantation in this way, the surgeon then may apply a series of adjusting strikes around a perimeter of the acetabular prosthesis to attempt to adjust to the desired orientation. Currently such post-impaction result is accepted as many surgeons believe that post-impaction adjustment creates an unpredictable and unreliable change which does not therefore warrant any attempts for post-impaction adjustment.

In most cases, any and all surgeons including an inexperienced surgeon may not be able to achieve the desired orientation of the acetabular prosthesis in the pelvis by conventional solutions due to unpredictability of the orientation changes responsive to these adjusting strikes. As noted above, it is most common for any surgeon to avoid post-impaction adjustment as most surgeons understand that they do not have a reliable system or method for improving any particular orientation and could easily introduce more/greater error. The computer navigation systems, fluoroscopy, and other measuring tools are able to provide the surgeon with information about the current orientation of the prosthesis during an operation and after the prosthesis has been installed and its deviation from the desired orientation, but the navigation systems (and others) do not protect against torsional forces created by the implanting/positioning strikes. The prosthesis will find its own position in the acetabulum based on the axial and torsional forces created by the blows of the mallet. Even those navigation systems used with robotic systems (e.g., MAKO) that attempt to secure an implant in the desired orientation prior to impaction are not guaranteed to result in the installation of the implant at the desired orientation because the actual implanting forces are applied by a surgeon swinging a mallet to manually strike the tamp.

A Behzadi Medical Device (BMD) is herein described and enabled that eliminates this crude method (i.e., mallet, tamp, and surgeon-applied mechanical implanting force) of the prosthesis (e.g., the acetabular cup). A surgeon using the BMD is able to insert the prosthesis exactly where desired with proper force, finesse, and accuracy. Depending upon implementation details, the installation includes insertion of the prosthesis into patient bone, within a desired threshold of metrics for insertion depth and location) and may also include, when appropriate and/or desired, positioning at a desired orientation with the desired threshold further including metrics for insertion orientation). The use of the BMD reduces risks of fracturing and/or shattering the bone receiving the prosthesis and allows for rapid, efficient, and accurate (atraumatic) installation of the prosthesis. The BMD provides a viable interface for computer navigation assistance (also useable with all intraoperative measuring tools including fluoroscopy) during the installation as a lighter more responsive touch may be used.

The BMD encompasses many different embodiments for installation and/or positioning of a prosthesis and may be adapted for a wide range of prostheses in addition to installation and/or positioning of an acetabular prosthesis during THR, including examples of a device, which may be automated, for production and/or communication of an installation agency to a prosthesis.

FIG. 1 illustrates a smart tool 100 for prosthesis installation, including structures and methods for operation of a force agency 105 and a responsive quantitative assessment 110 with respect to installation of a prosthesis P (e.g., an acetabular cup) into a prepared cavity in a portion of bone (e.g., an acetabulum). Agency 105 may include several different types of force applicators, including vibratory insertion agencies and/or controlled impaction agencies and/or constant applied force and/or other force profile as described in the incorporated patents and applications. Quantitative assessment 110 may include a processor and sensors for evaluating parameters and functions as described herein including a rigidity metric and an elasticity metric, for press-fit fixation of prosthesis P, such as in realtime or near-realtime operation of force agency 105.

Figure 2:
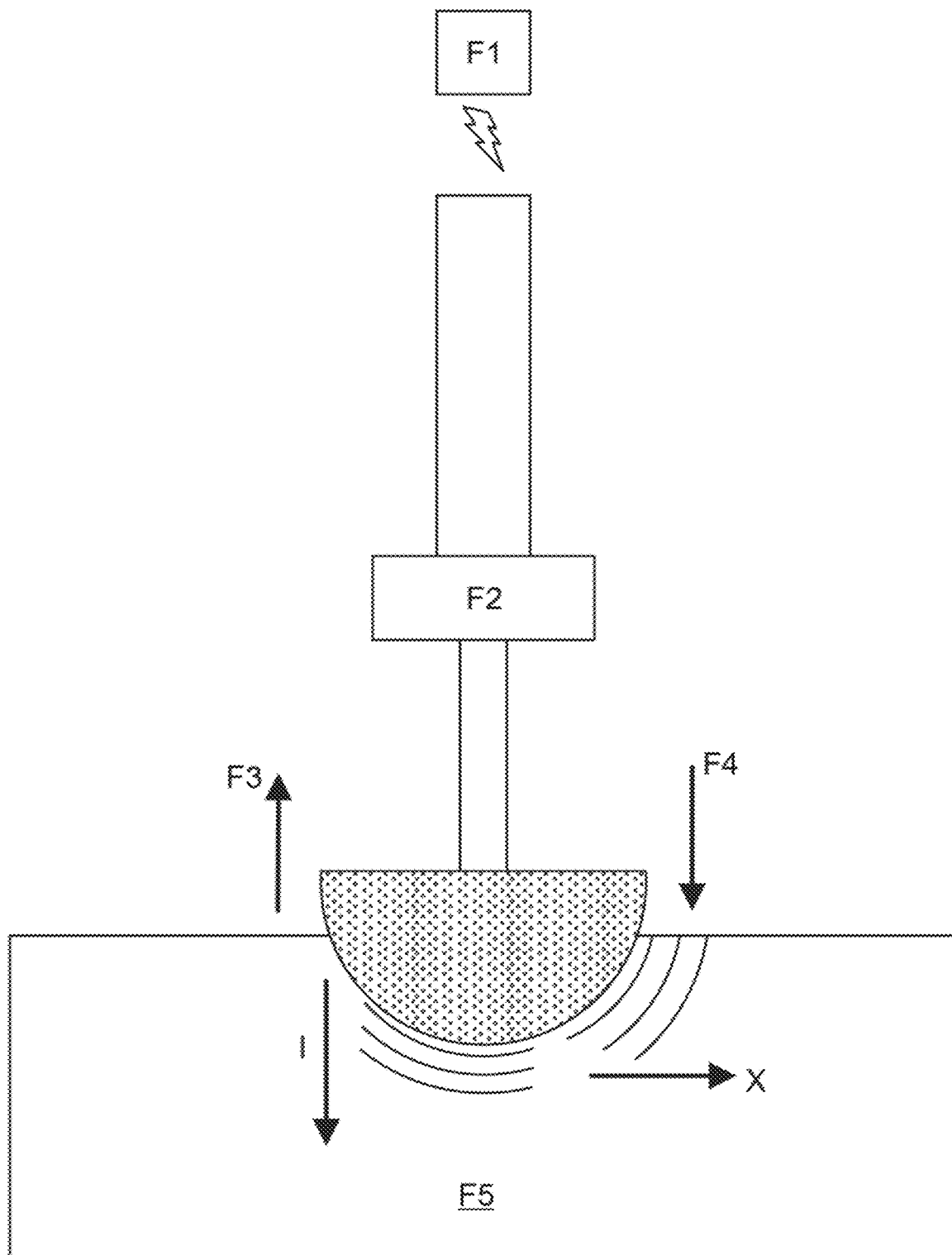
FIG. 2 illustrates an identification of forces in a press fit fixation installation of a prosthesis.

FIG. 2 illustrates an identification of forces in a press fit fixation installation of a prosthesis. These forces, as illustrated, include F1 (applied force), F2 (responsive force in smart tool), F3 (resistive force to installation), F4 (axial extractive force), and/or F5 (force in bone substrate). There may be other forces that may be measured or determined to be correlated, responsive, and/or related to these forces. In some circumstances, multiple related or correlated forces may be "fused" into a fusion force that provides a robust evaluation of the component forces, with any appropriate individual weightings of component forces in the fused force. That is some embodiments, a press-fit fixation may be assessed based upon contributions from multiple forces fused together rather than evaluations of individual forces or derivatives thereof.

When press fitting an acetabular component into an undersized cavity, one may expect to encounter three regions with distinct characteristics: (a) poor seating and poor pull out force; (b) deep insertion and good pull out force; and (c) full insertion which may also have strong fixation but includes higher (and possibly much higher) risk of fracture.

Some embodiments may exhibit relationships between extraction force (F4) and cup insertion CI with respect to similarity and proportionality to a standard stress/strain curve of material deformation.

While two collisions occur during the process of prosthesis impaction into bone in some embodiments for each force application, a proximal collision is usually elastic and typically presents a maximum value of F1 for any given impact energy E of the force application. A distal collision is conversely initially inelastic and progresses to an elastic state as insertion no longer occurs. In some experiments, force measurements in the impaction rod (F2) and bone (F5) may represent the distal collision.

Figure 3:
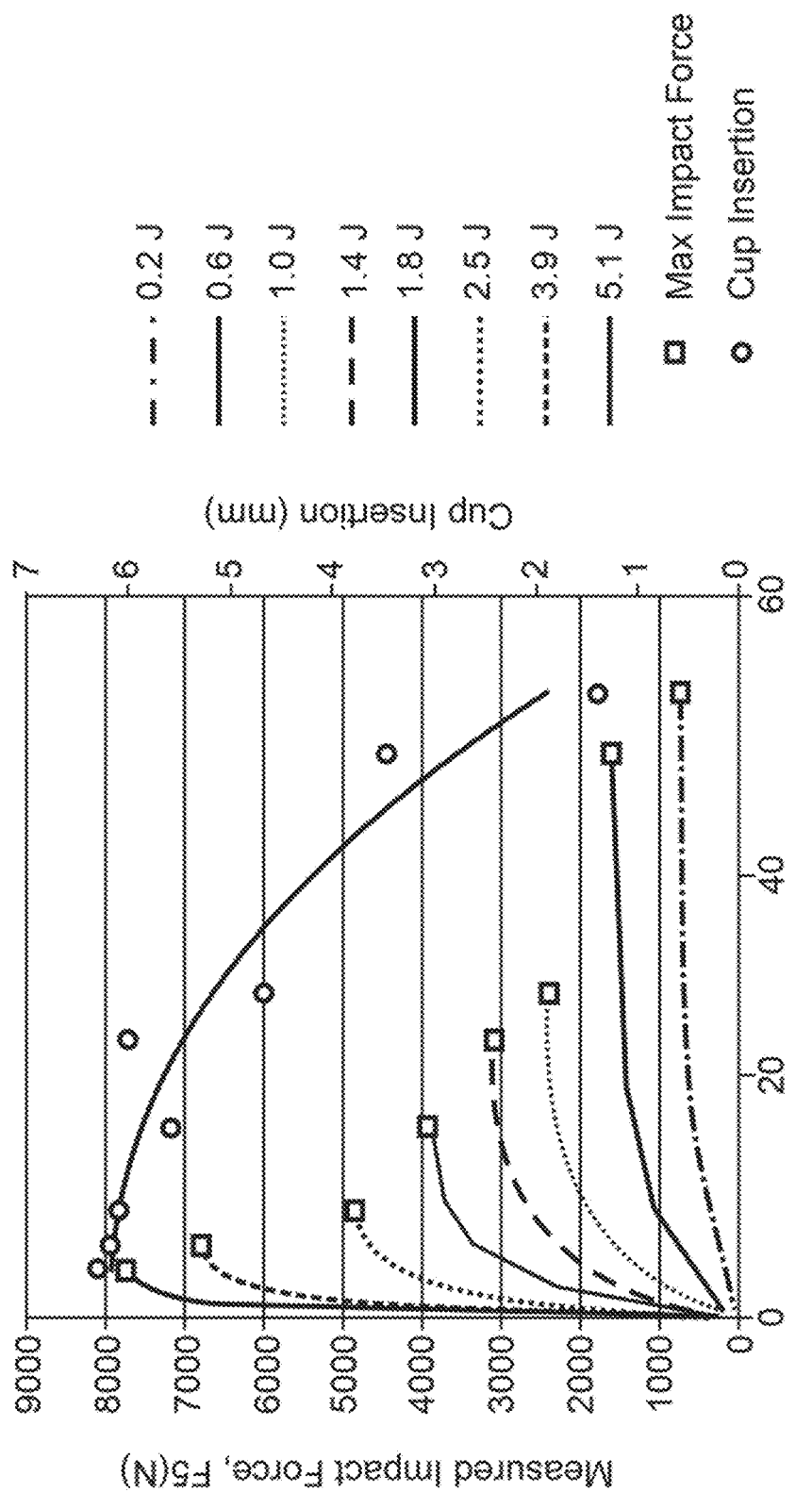
FIG. 3 illustrates a set of relationships between measured impact force (e.g., F5), number of impacts (NOI), cup insertion (CI), and impact energy Joules (J)

FIG. 3 illustrates a set of relationships between measured impact force (e.g., F2, F3, and/or F5 and/or derivatives and/or combinations thereof), number of impacts (NOI), cup insertion (CI), and impact energy Joules (J). Experiments in the study of vibratory insertion of orthopedic implants [Published Patent App. Invasive Sensing Mechanism: Pub No. 20170196506, incorporated herein by reference in its entirety for all purposes] where an oversized acetabular prosthesis, Zimmer Continuum Cup (62 mm) was inserted into an undersized (61 mm) bone substitute cavity (20 lbs Urethane foam), using three different insertion techniques including controlled impaction, vibratory insertion, and constant insertion. The forces at play were considered in FIG. 2. An 8900N force gauge was placed within the polyurethane sample to measure forces in the cavity F5.

With the controlled impaction technique we tested eight-drop heights producing a range of impact energies from 0.2 J to 5.0 J corresponding to impact forces ranging from 550N to 8650N. Five replications were performed for each height, with a total sample population of 40 units. For each sample, impacts were repeated at a selected drop height until implant displacement between impacts were within the measurement error of 0.05 mm. Peak impact force in bone F5, total cup insertion CI, and number of impacts NOI to full insertion were recorded for each sample. Cup stability was measured by axial extraction force by means of a pull test using Mark 10 M5-100 test stand and force gauge. The results are shown in Table I.

TABLE I

Drop Test Results

| Drop Height (mm) | Impact Energy (J) | Maximum Impact Force in bone F5 (N) | Mean Number of Impacts | Cup Insertion (mm) | Extraction Force F4 (N) |
|---|---|---|---|---|---|
| 10 | 0.2 | 774 | 52 | 1.4 | 71 |
| 30 | 0.6 | 1641 | 47 | 3.5 | 258 |
| 50 | 1.0 | 2437 | 27 | 4.7 | 480 |
| 70 | 1.4 | 3104 | 23 | 6.0 | 676 |
| 90 | 1.8 | 3927 | 16 | 5.6 | 765 |
| 130 | 2.5 | 4870 | 9 | 6.1 | 827 |
| 200 | 3.9 | 6814 | 6 | 6.2 | 849 |
| 260 | 5.1 | 7757 | 4 | 6.3 | 867 |

These data indicate that every level of impact energy is associated with a final depth of cup insertion CI, a plateauing of the force response in bone F5 to an asymptote, and a certain rate of insertion inversely related to the number of impacts NOI required for insertion. As an example, it took 4 impacts for a maximum applied force of 7757 N to insert the cup 6.3 mm, whereas it took 52 impacts for a maximum applied force of 774 N to insert the cup 1.4 mm.

Figure 4:
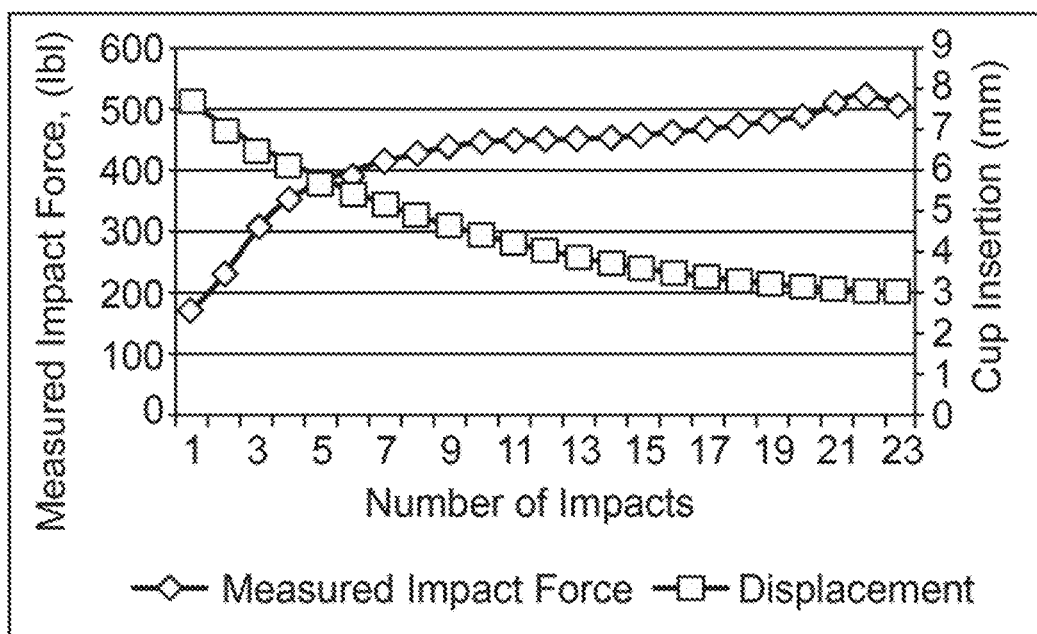
FIG. 4 illustrates a relationship of force in bone (e.g., F5) and cup insertion (CI) for 1.0 Joules (J)
Figure 5:
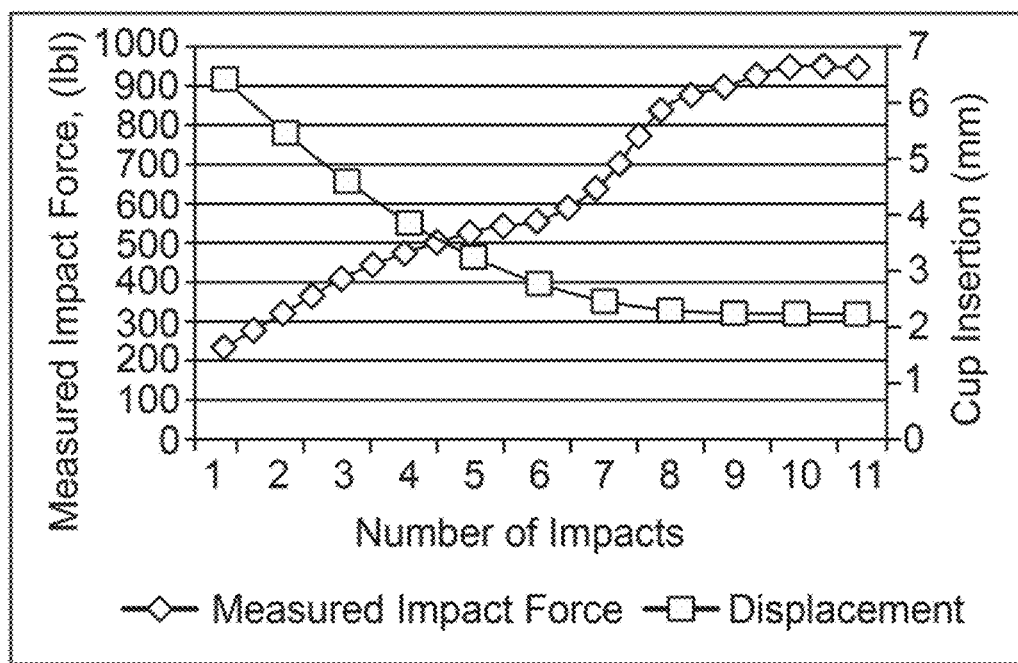
FIG. 5 illustrates a relationship of force in bone (e.g., F5) and cup insertion (CI) for 1.8 Joules (J)

FIG. 4 illustrates a relationship of force in bone (e.g., F5) and cup insertion (CI) for 1.0 Joules (J) and FIG. 5 illustrates a relationship of force in bone (e.g., F5) and cup insertion (CI) for 1.8 Joules (J). A decaying of the force response in bone F5 to an asymptote (when ΔF5 approaches 0) could be used as a parametric value guiding incremental application of energy to obtain optimal press fit fixation of implants. This phenomena is identified herein as the rigidity factor (or rigidity metric) which appears to reach a maximum for any given impact energy.

Figure 6:
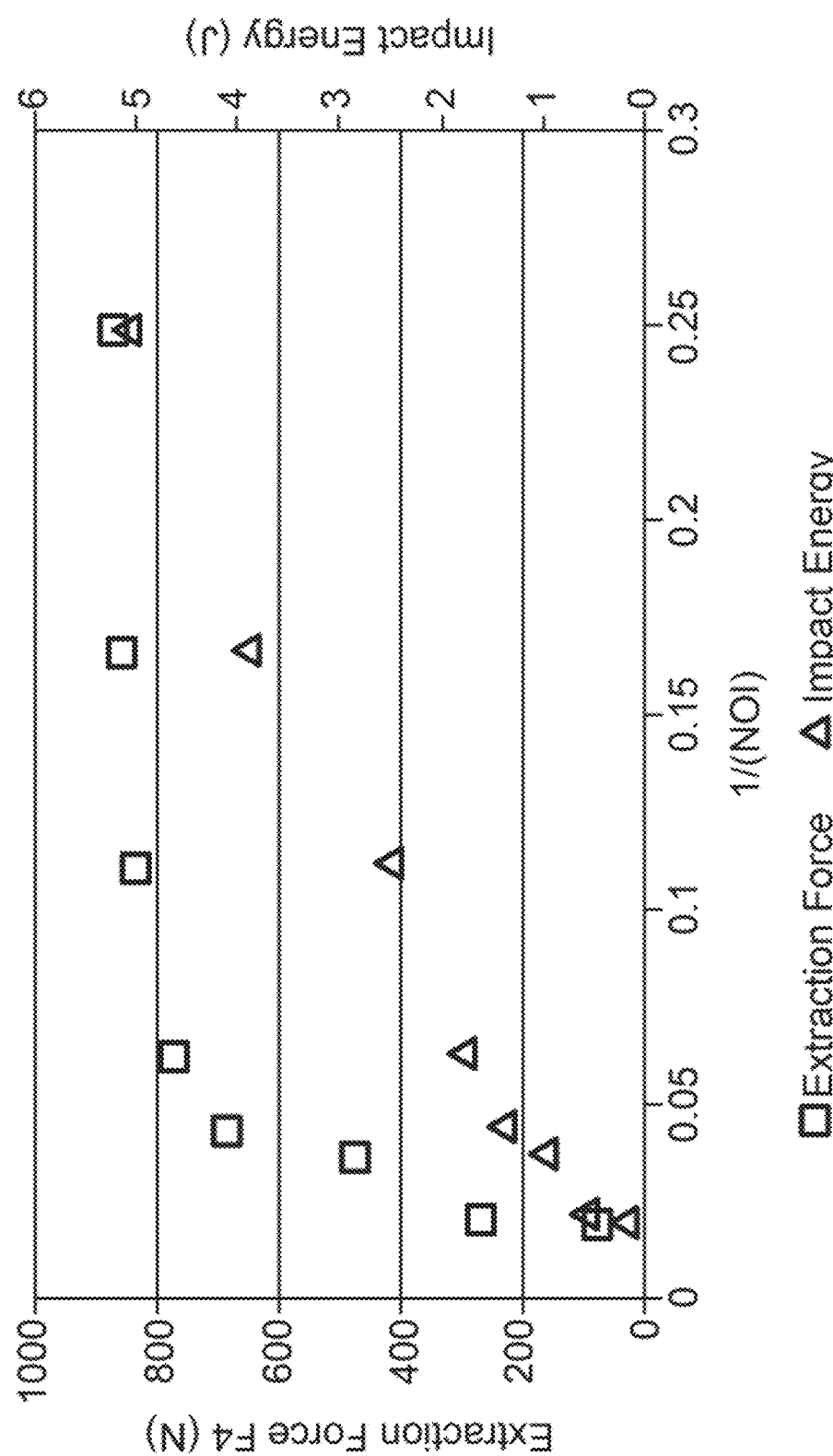
FIG. 6 illustrates a relationship between a rate of insertion (1/NOI), extractive force (e.g., F4), and impact energy.

FIG. 6 illustrates a relationship between a rate of insertion (1/NOI), extractive force (e.g., F4), and impact energy. A direct relationship was observed between rate of insertion, inversely related to number of impacts NOI, and the extractive force F4, and this phenomenon is termed an elasticity factor (or elasticity metric), which appears to provide a real-time estimation of the extractive force of the implant/bone interface, as well as an indirect measure of the elastic/plastic behavior of the aperture of bone. A decaying rate of insertion is considered and appears inversely related to a number of impacts and suggests an ultimate stress point of the cavity aperture.

Figure 7:
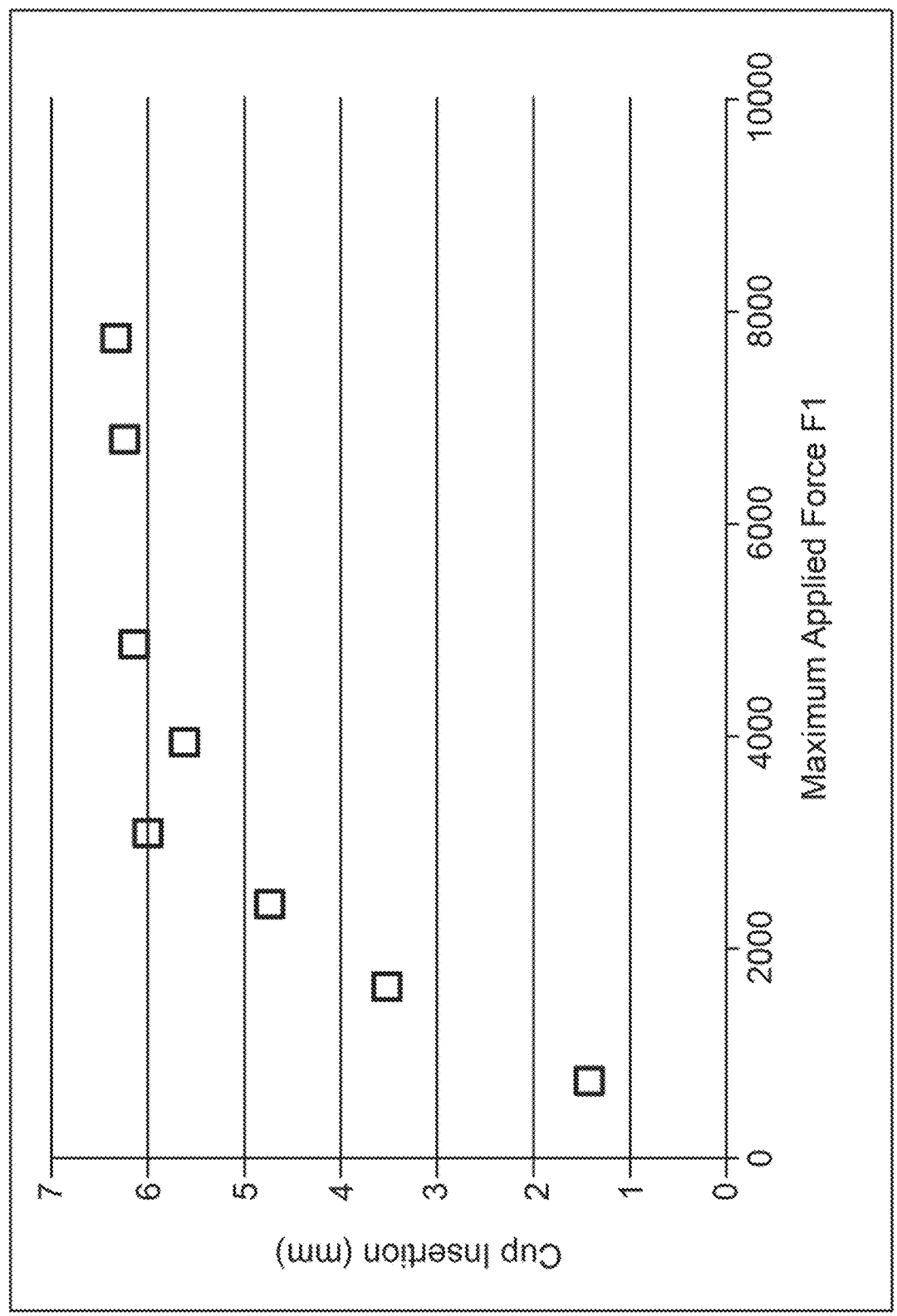
FIG. 7 illustrates a relationship between maximum applied force (e.g., F1) and cup insertion (CI)
Figure 8:
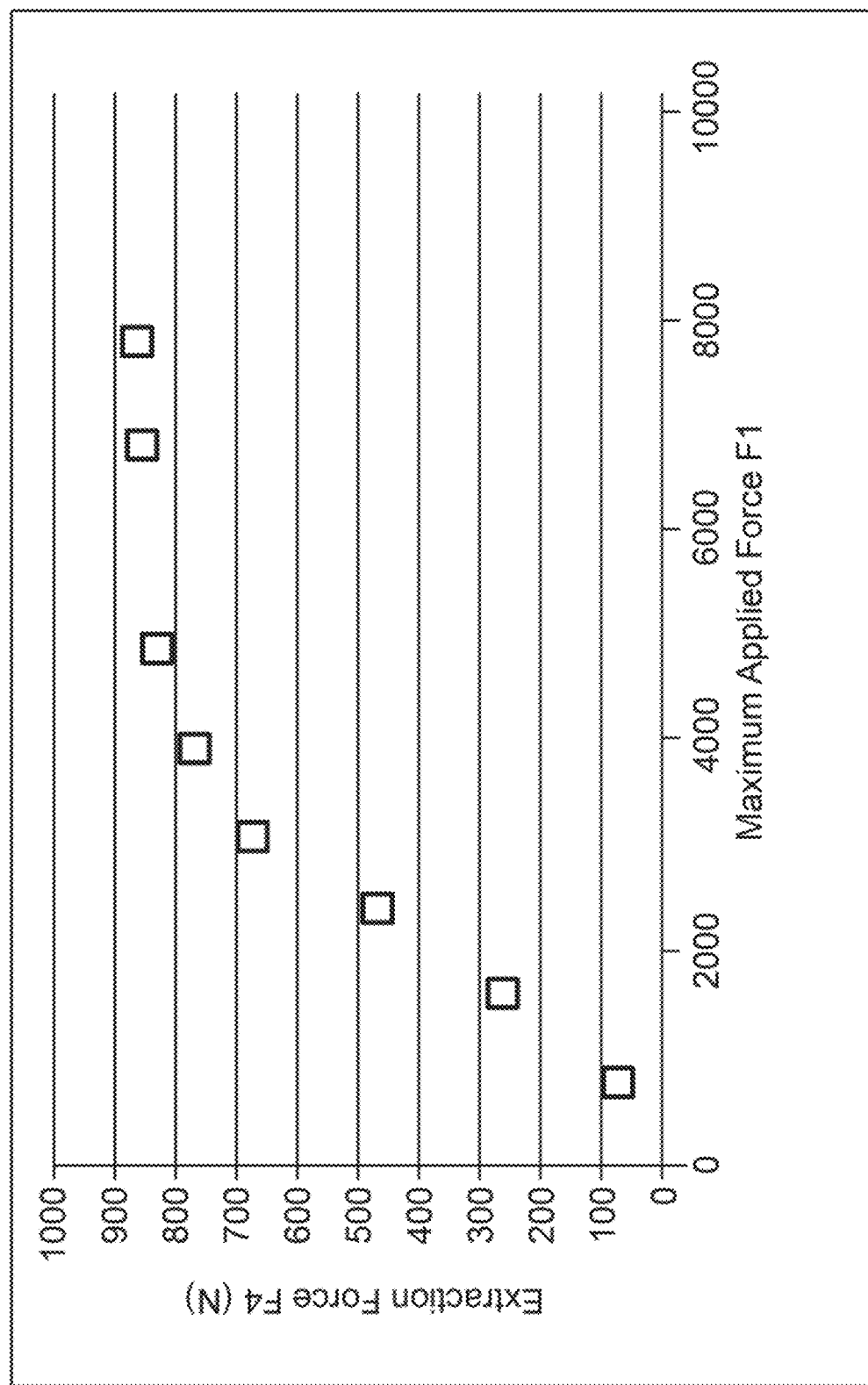
FIG. 8 illustrates a relationship between maximum applied force (e.g., F1) and an extractive force (e.g., F4)

FIG. 7 illustrates a relationship between maximum applied force (e.g., F1) and cup insertion (CI) and FIG. 8 illustrates a relationship between maximum applied force (e.g., F1) and an extractive force (e.g., F4). The relationships of applied force F1 and cup insertion CI as well as applied force F1 and extractive force F4 were evaluated and showed characteristic non-linear curves.

Of note was the observation that an inflection point or (range) exists above which increased applied force F1 (impact energies) did not appear to provide any meaningful increase in cup insertion CI or extraction force F4. As example 1.8 joules of impact energy produced 5.6 mm (89%) of cup insertion CI and 827N (88%) of extraction force F4. An additional 3.3 joules of impact energy was required for a marginal insertion gain of 0.7 mm and extraction force gain of 102N.

Questions were posed as to how much force is required for optimal press fit fixation? Does the insistence to fully seat the cup work against the patients and surgeon? Do surgeons risk fracturing the acetabulum in the desire to fully seat the cup? The existence of polar gaps in acetabular press fit fixation have been clinically studied and shown no adverse outcomes.

It was contemplated that a point or (a small range), defined by the parametric values above, exists which could produce the best fixation short of fracture (BFSF) and an embodiment may propose BFSF as an ideal endpoint for all press fit joint replacement surgery. BFSF may, in some situations, act not only as a point of optimal press fit, but also define a sort of speed limit or force limit for the surgeon.

In this application an embodiment may develop a method described as the invasive sensing mechanism (ISM), by which the end point BFSF can be defined in four chosen systems. Additionally, an embodiment may develop an Automatic Intelligent Prosthesis Installation Device (AI-PID) that can quantitatively access this point. The following concept is proposed for a fixation algorithm to achieve BFSF for any implant/cavity interface. (A Double Binary Decision)

Figure 9:
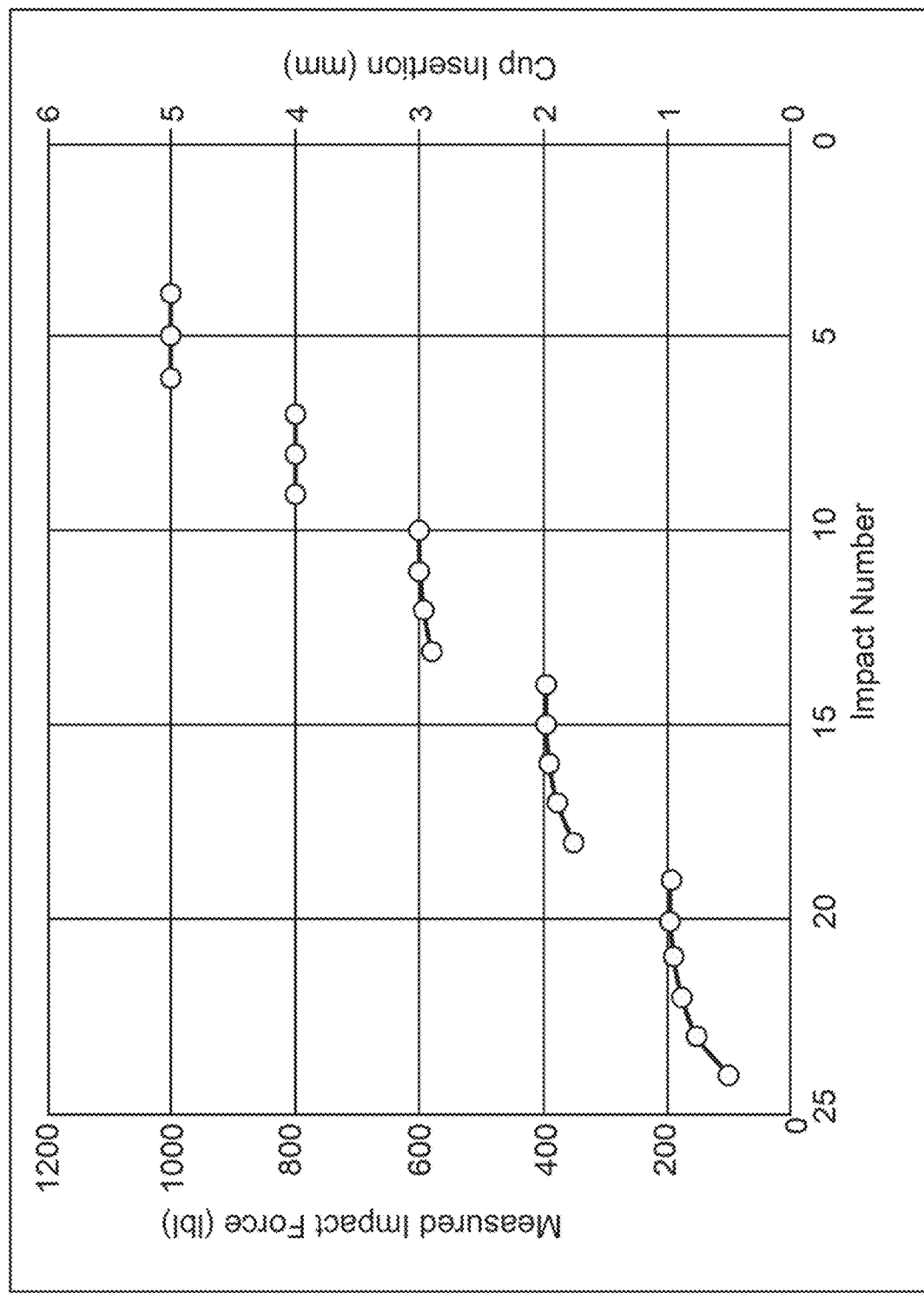
FIG. 9 illustrates a representative force response for incrementing impact energies.

FIG. 9 illustrates a representative force response for incrementing impact energies. The rigidity factor represented by plateauing levels of force in bone (e.g., F5) can be used to guide incremental increase in impact energy J. For any impact energy J, as the force in bone plateaus to a maximum, no further insertion is occurring; a decision can be made as to whether impact energy should be increased or not. This is the first binary decision. The elasticity factor represented by the speed of insertion of an implant (e.g., inversely related to number of impacts (NOI) required for insertion) can be used to guide the surgeon as to whether application of force should continue or not. This is the second binary decision. Two binary decisions for BFSF which may not include full seating.

Figure 10:
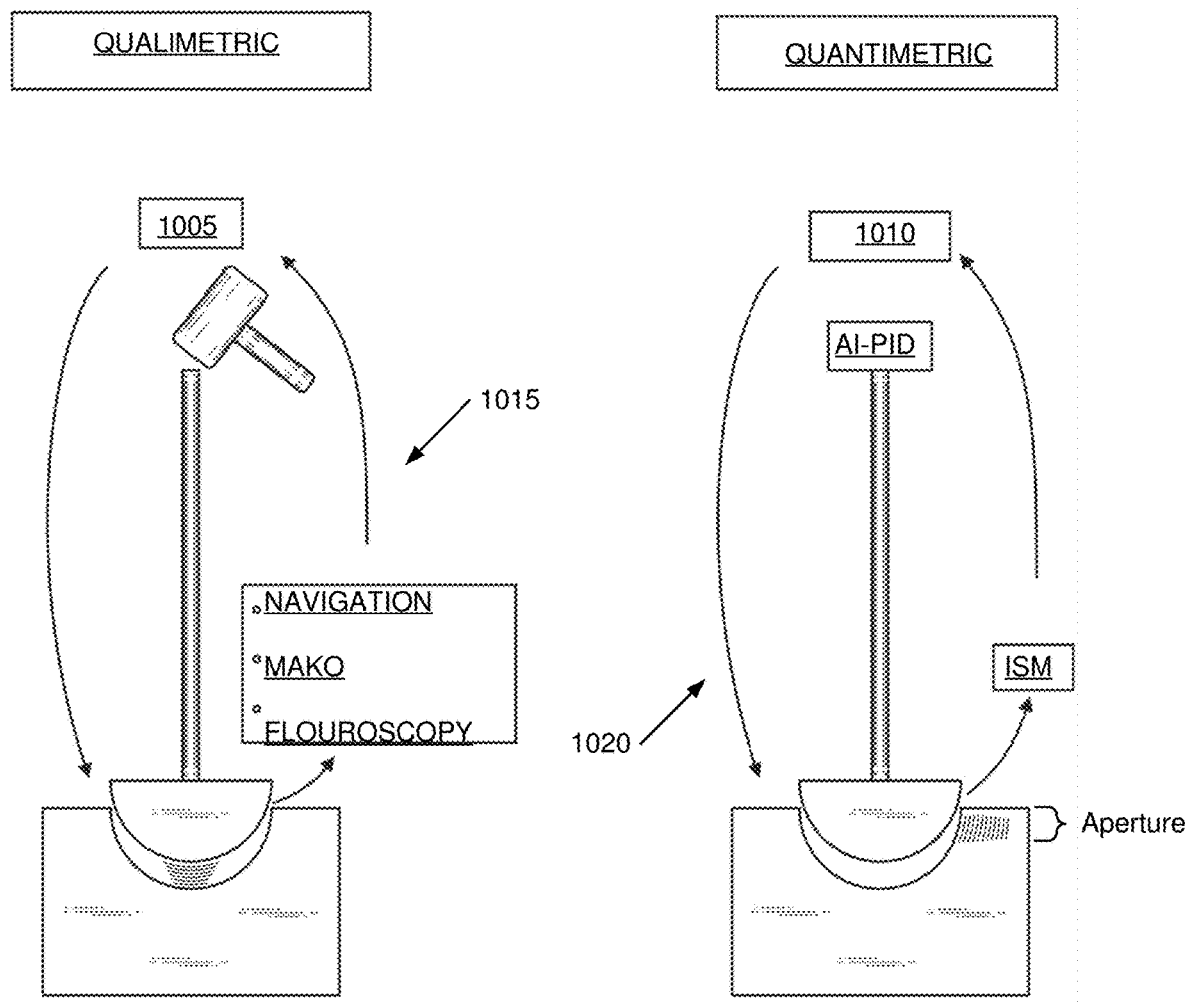
FIG. 10 illustrates a comparison of a quantitative system versus a qualimetric system for evaluating a real time non-visually tracked press fit fixation.

FIG. 10 illustrates a comparison of a quantimetric system (including a measured quantitative determination/use of BFSF) versus a qualimetric system (typically based on a visual qualitative assessment of a depth of insertion) for evaluating a real time non-visually tracked press-fit fixation. An invasive sensing mechanism (ISM) and an automatic intelligent prosthesis installation device (AI-PID) may standardize an application of force and an assessment of a measured quality of fixation in joint replacement surgery, through exploitation of the relationships between the force responses in the installation tool, bone and the interface.

The qualimetric system includes various visual tracking mechanisms (e.g., computer navigation, MAKO assistant, fluoroscopy, and the like) in which an uncontrolled force is applied manually such as by a mallet 1005. The quantitative system operates an insertion agency 1010 which enables application of controlled forces (e.g., force vectors of controlled direction and/or controlled magnitude). The insertion agency may involve ISM which, in some implementations, may assess the stress response of bone at the implant/bone interface as opposed to qualimetric discussed in the above paragraph that does visual tracking.

The qualimetric system includes a striking-evaluation system 1015 in which a mallet strikes a rod which drives a prosthesis into a prepared cavity. The surgeon then qualitatively assesses the placement using secondary cues (audio, tactile, visual imaging) to estimate a quality of insertion and assume a quality of fixation. This cycle of strike and assess continues until the surgeons stop, often wondering whether stopping is appropriate and/or whether they have struck the rod too many times/too hard.

In contrast, a quantitative cycle 1020 in the quantimetric system includes operation of an insertion agency, measurement of force response(s) to determine elastic and rigidity factors, and use these factors to determine whether to continue operation and whether to modify the applied force from the insertion agency. The quantitative system assumes BFSF and optimal press-fit fixation relies primarily on a cavity aperture of a relatively oversized prosthesis/relatively undersized cavity which provides a contact area around a "rim" of the cavity where bone contacts, engages, and fixates the prosthesis. A depth of the aperture region may depend upon a degree of lateral compression of the prepared bone as the prosthesis is installed.

The parametric values of the quantimetric system provide meaningful actionable information to surgeons as to when to increment the magnitude of force, and as to when to stop application of force. Additionally, surgeons currently utilize qualitative means (auditory and tactile senses) as well as auxiliary optical tracking means (fluoroscopy, navigation) to assess the depth of insertion and estimate a quality of fixation during press fit arthroplasty. Application of force to achieve press fit fixation is uncontrolled and based on human proprioceptive and auxiliary optical tracking means. The optimal endpoint for press fit fixation remains undefined and elusive.

An embodiment may include development of a reliable quantitative technique for real-time intra-operative determination of optimal press fit, and the development of a smart tool to obtain this point automatically. The ability to base controlled application of force for installation of prosthesis in joint replacement surgery on the force response of the implant/bone interface is an innovative concept allowing a quantimetric evaluation of the implant/bone interface.

An embodiment for a quantimetric system may include a hand-held tool (See, e.g., FIG. 1) that can produce impact energies of the necessary magnitude and accuracy. A variety of actuation methods can be used to create controlled impacts, including pneumatic actuators, electro magnetics actuators, or spring-loaded masses. An example implementation using pneumatic, vibratory, motorized, controlled, or other actuation The device shall have industry standard interfaces in order to allow for use with a variety of cup models.

A slide hammer pneumatic prototype is created to allow precise and incremental delivery of energy E. It is equipped with inline force sensors in order to measure resulting forces F1 and F2 and controlled by integrated electronics that provides analysis of F1, F2, $\Delta$F2, number of impacts, and impact energy E. Programed algorithms based on the double binary system described herein will produce successive impacts of a known energy, making two simultaneous binary decisions before each impact: (a) modify energy or not; and (b) apply energy or not. These two binary decisions will be based on parametric values produced by the control electronics, which provides an essential feedback of the implant/bone interface, and the elastic response of bone at the aperture. The following algorithm provides a basic example of the double binary decision making process.

A method for assessing a seatedness and quality of press fit fixation includes a series of operations for installing a prosthesis into a relatively undersized cavity prepared in a portion of bone, including communicating, using an installation agency, a quantized applied force to a prosthesis being press-fit into the cavity; monitoring a rigidity metric and an elasticity metric of the prosthesis with respect to the cavity (some embodiments do this in real-time or near real-time without requiring imaging or position-determination technology); further processing responsive to the rigidity and elasticity metrics, including continuing to install the prosthesis at present level of applied force while monitoring the metrics when the metrics indicate that installation change is acceptable and a risk of fracture remains at an acceptable level, increasing the applied force and continuing applying the installation agency while monitoring the metrics when the metrics indicate that installation change is minimal and a risk of fracture remains at an acceptable level, or suspending operation of the installation agency when the metrics indicate that installation change is minimal when a risk of fracture increases to an unacceptable level.

1. Apply energy E1 and measure F2, number of impacts (NOI), $\Delta$F2.

2. Monitor F2 over number of impacts (NOI), and/or monitor $\Delta$F2 as it approaches zero.

3. When $\Delta$F2 approaches zero, insertion is not occurring for that particular energy E1. If NOI required to achieve this point is sufficiently large (low speed of insertion) as determined by the control algorithm, then E1 is increased to E2

4. Continue steps 1 through 3 until the NOI required for ΔF2 to approach zero is sufficiently small (high speed of insertion) as determined by the control algorithm.

5. The smart tool may be implemented so it will not generate automated impacts after this level is reached. Additional increase in energy E is not recommended but can be produced manually or after a considered override by the surgeon. For example, it may be that no more than one incremental manual increase is recommended or established as a best practice.

Validation of the tool may be performed by comparing the quality of insertion (extractive force F4) produced by AI-PID with those produced by a mallet and standard impaction techniques. Specifically, the two distinct endpoints of (i) BFSF (achieved through AI-PID) and (ii) full seating (achieved through mallet strikes) will be compared to determine differences in the extractive force F4 and fracture incidence. A risk benefit analysis will be done to determine whether additional impacts and insertion beyond BFSF provided any significant value as to implant stability, or conversely led to increased incidence of fracture of the cavity. (As noted herein, it may be the case that BFSF may be achieved without full seating, a stated goal of many conventional procedures.)

It is anticipated that the measurements of F2, and ΔF2 and its comparative analysis with respect to number of impacts NOI will provide a principled and organized process for application of energy to achieve a desired endpoint of fixation BFSF. We expect that the first order relationship of ΔF2 will provide the information as to whether, for any particular level of applied energy, insertion is occurring or not; providing a guidance as to whether applied energy should be increased. We expect the rate of ΔF2 decay to zero will provide information about elastic/plastic behavior of the aperture, indicating when the maximum strain X, normal force FN, and extractive force F4 at the aperture of the bone cavity have been achieved. We anticipate reproducing the results of phase I aim 1, namely that there is a strong correlation between pull force F4 and rate of decay of ΔF2, that an inflection point exists in the elasticity factor, beyond which addition of impact energy will lead to marginal gains in extraction force F4 and depth of insertion, mitigating against goal of full seating as the best policy.

We have indicated that the grasp of bone (bone substitute) on an implant at the aperture can be modeled in some cases by formula such as FN*Us where FN represents the normal forces at the interface, and Us represents the coefficient of static friction. FN is estimated by Hooke's Law and is represented by K·X, where K represents the material properties of bone including the elastic and compressive moduli and X represents the difference in diameter between the implant and the cavity. We note that the value of K can vary dramatically between different ages and sexes. We anticipate this tool to be capable of automatically producing the proper amount of impact energy E, cup insertion CI, stretch on bone X, normal force FN, and extractive force F4 to achieve optimal press fit for patients of various ages and sexes, eliminating an over reliance on surgeon senses and experience.

Having access to this interface sensing phenomena, an embodiment may develop a simple controlled impaction process that allows the surgeon to quantize the impact energy, and deliver it in a controlled and modulatable fashion based on the above two parametric value representing the stress/strain behavior of bone. Some embodiments may develop the concept of controlled force application based on an evaluation of the interface force phenomena (forces felt at the prosthesis/cavity interface). This is in stark contradistinction of uncontrolled application of force with a mallet based on a VISUAL assessment/tracking of the depth of prosthesis insertion (MAKO, all navigation techniques, Fluoroscopy, Nikou—a navigation technique).

There may be many different ways to asses-rigidity factor and to asses—an elasticity factor. FIG. 11-FIG. 14 illustrates F2 approaching F1 and F5 approaching F1, as well as (ΔF2 approaching 0) and (ΔF5 approaching 0). Additional non-illustrated ways include F3 approaching F1 and ΔF3 approaching 0). As noted herein, data fusion may produce a fusion variable that can measure, evaluate, or indicate rigidity and/or elasticity. For example, one or more of F2, F3, and F5, appropriately weighted, may be fused into a variable that may be used such as by comparing to F1 or delta fused variable compared to a threshold value (such as zero).

Figure 11:
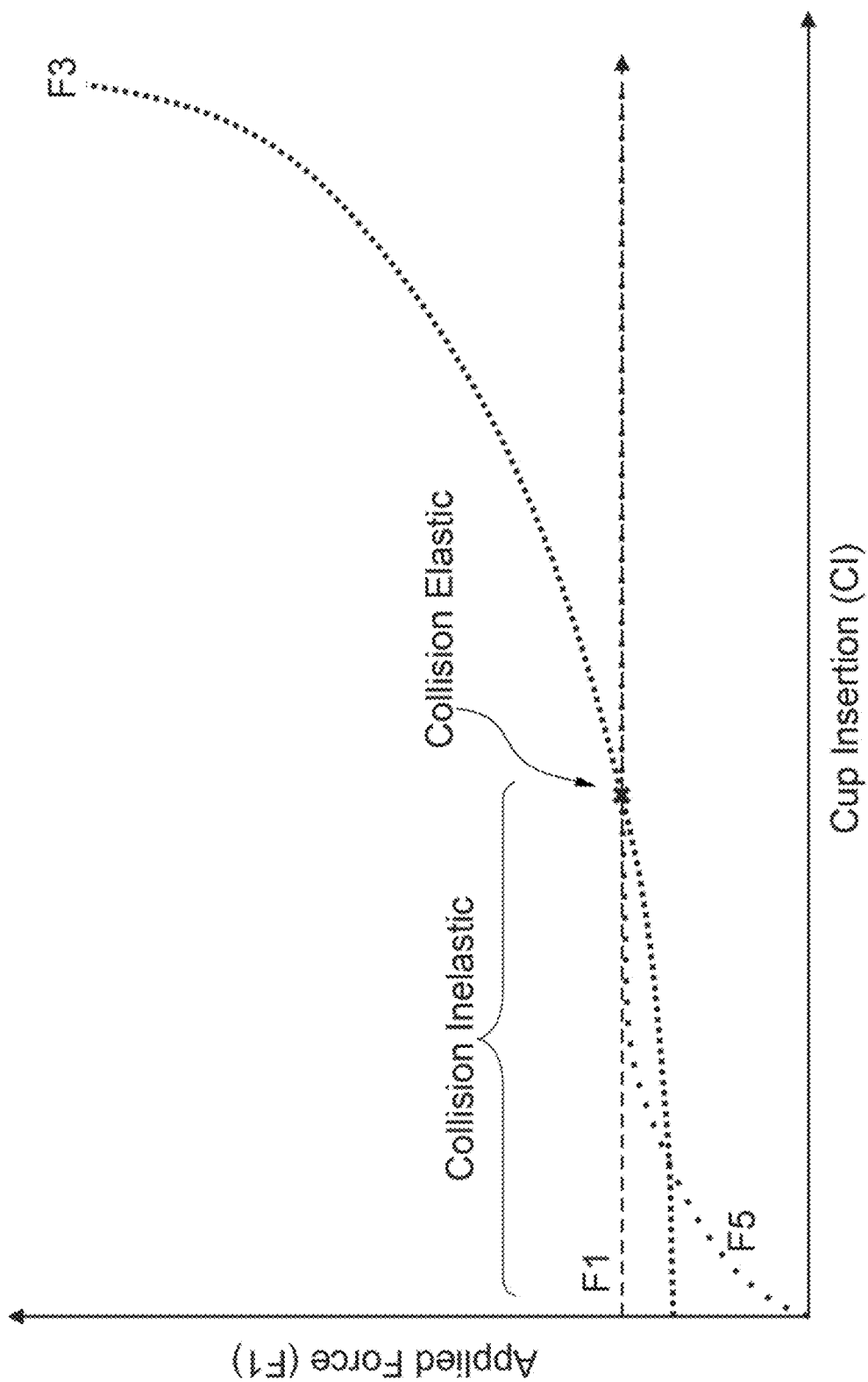
FIG. 11-FIG. 14 illustrate a set of rigidity metric measurements.
Figure 12:
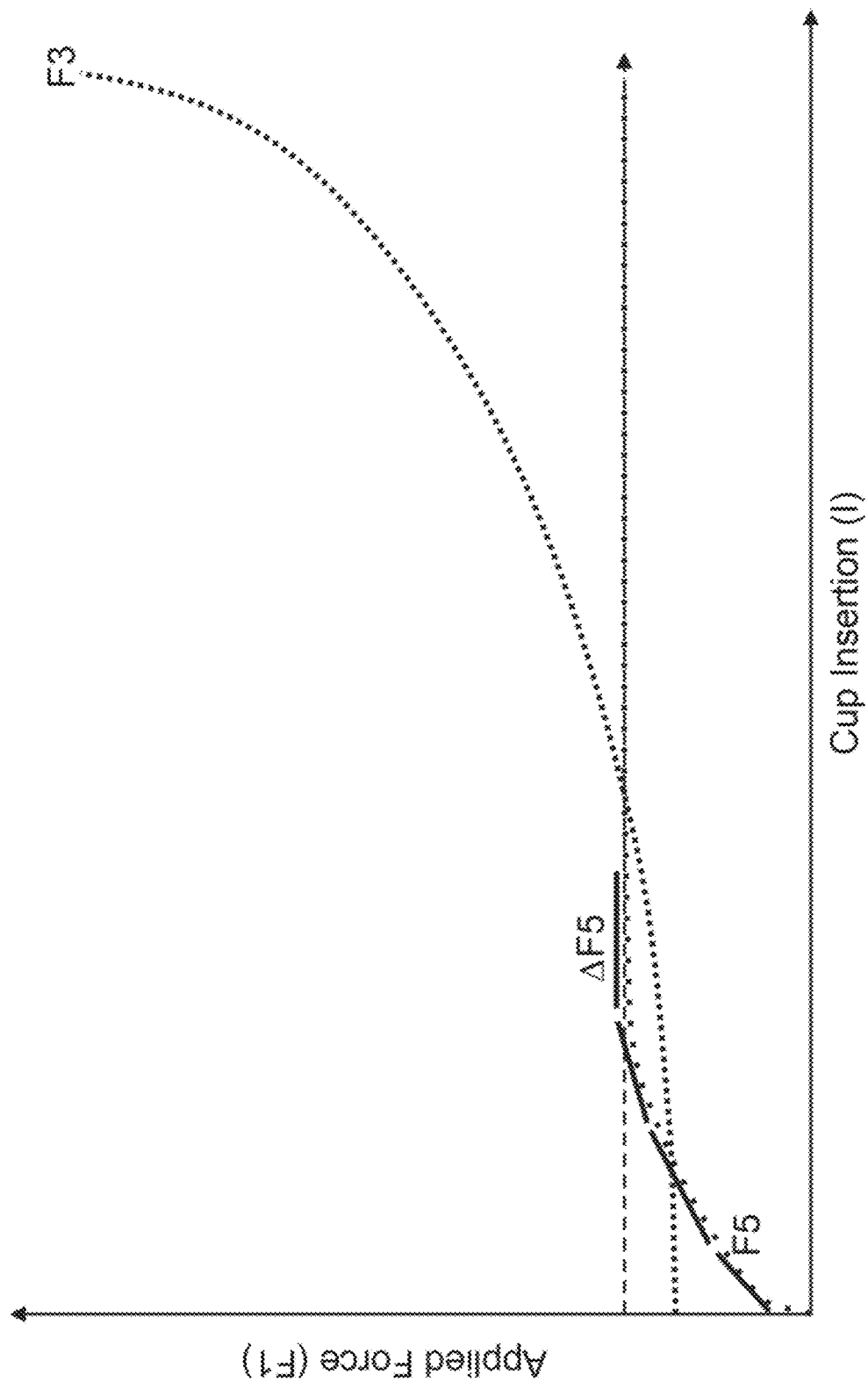
Figure 13:
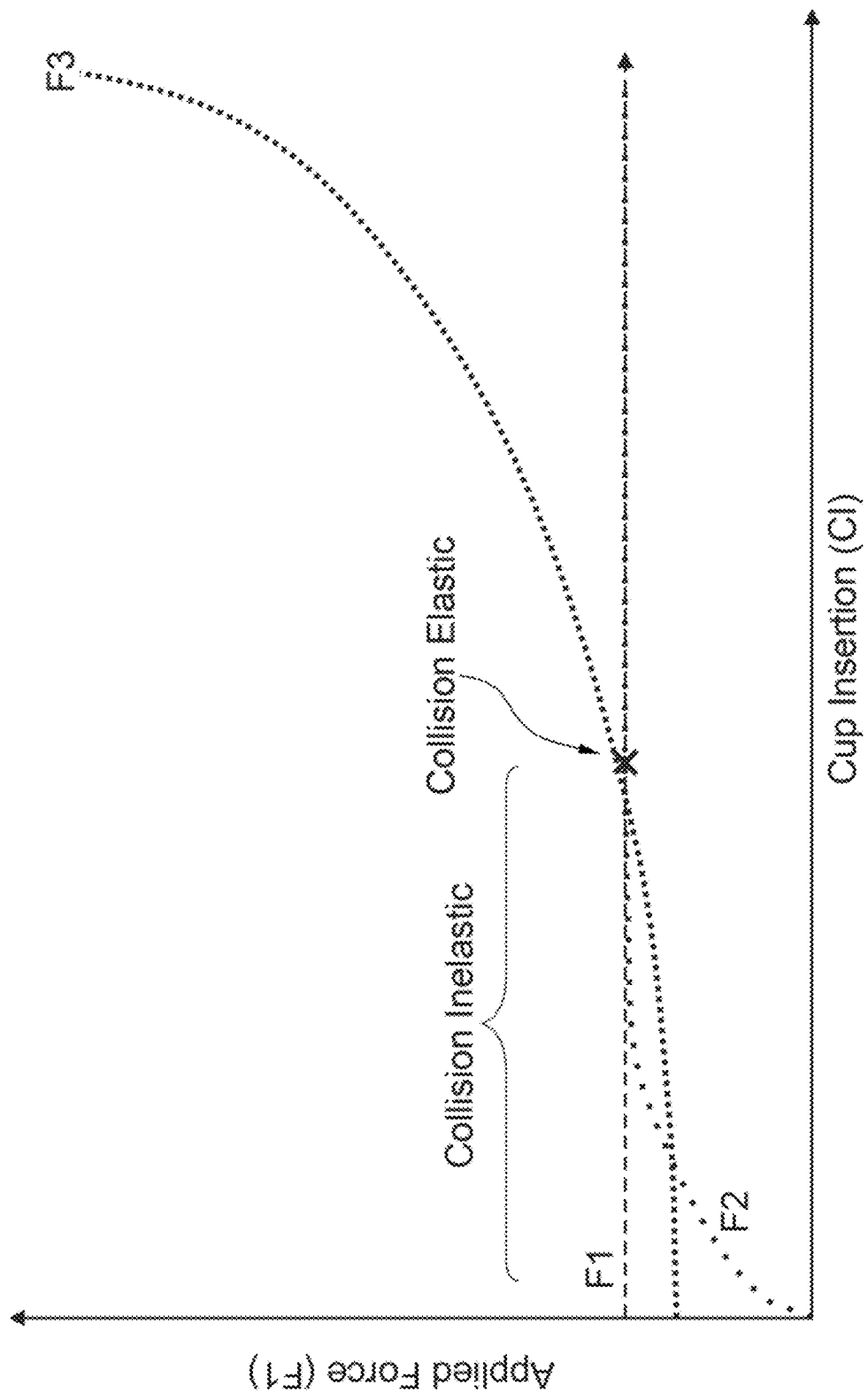
Figure 14:
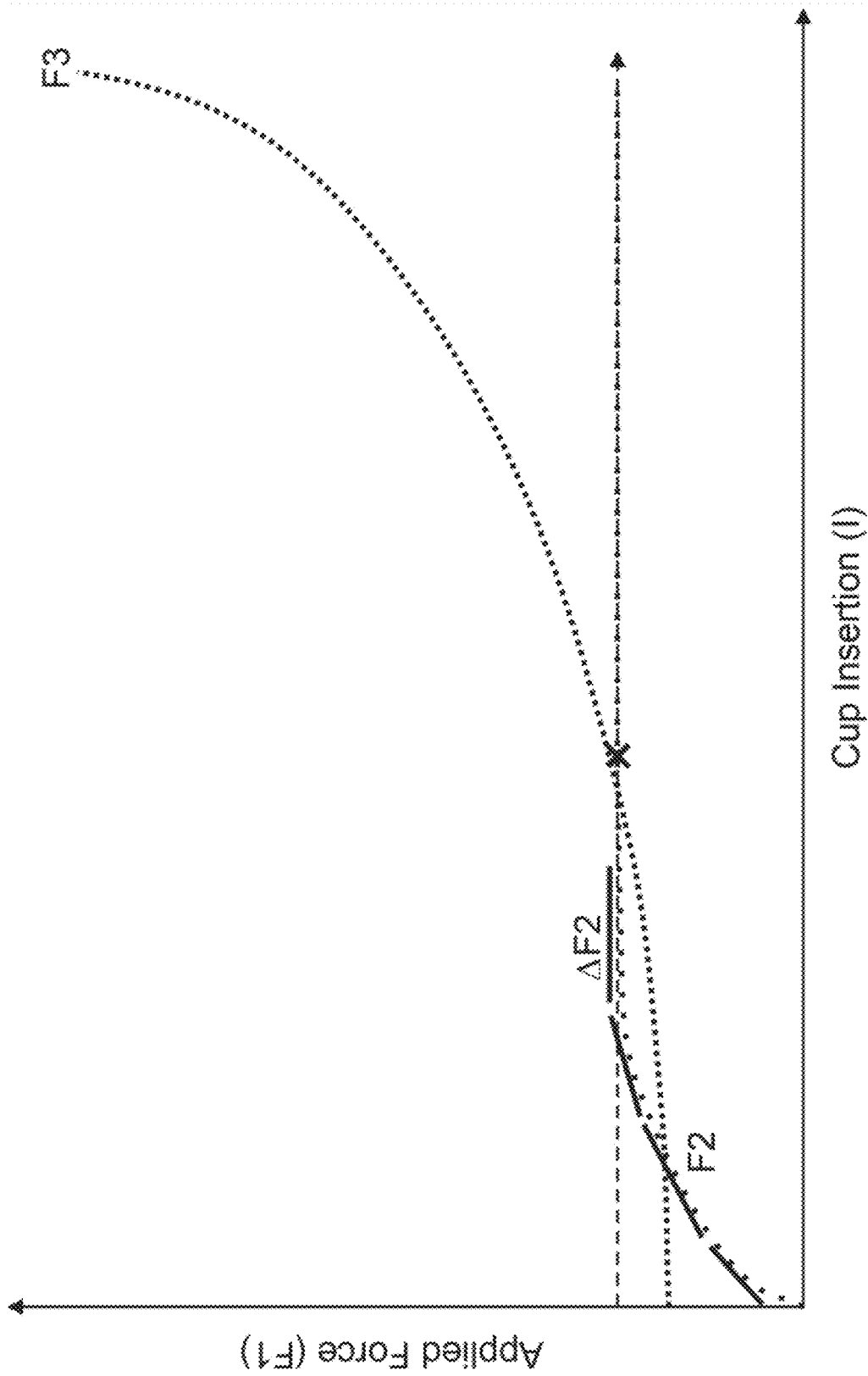

FIG. 11-FIG. 14 illustrate a set of rigidity metric measurements that may be used in the methods and systems described herein. FIG. 11 illustrates a comparison of F5 to F1; FIG. 12 illustrates a comparison of ΔF5 to a predetermined threshold (e.g., 0.0); FIG. 13 illustrates a comparison of F2 to F1; and FIG. 14 illustrates a comparison of ΔF2 to a predetermined threshold (e.g., 0.0).

Figure 15:
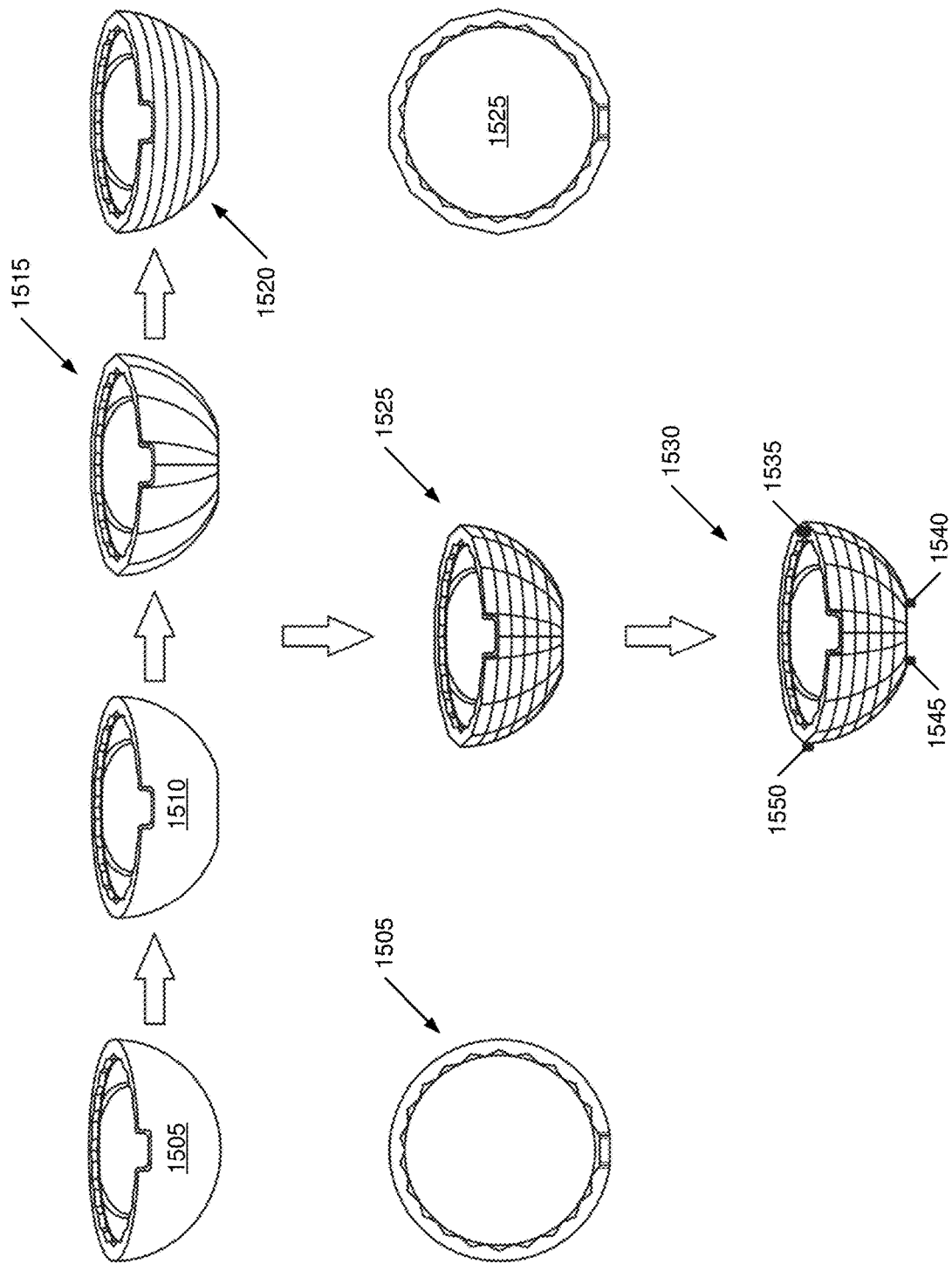
FIG. 15 illustrates an evolution of an acetabular cup consistent with improving press fit fixation.

FIG. 15 illustrates a possible evolution of an acetabular cup 1505 consistent with improving press fit fixation. As noted, a conventional acetabular cup for an implant includes a hemispherical outer surface designed to be installed/impacted into a prepared bone cavity (also hemispherical produced from a generally hemispherical reamer for example).

Different stages of evolution illustrate possible improvements to prosthesis embodiments that are responsive to assumptions and embodiments of the present invention. An assumption of some conventional systems is that full depth of insertion results in a maximum extractive press fit fixation. In contradiction to this assumption, it may be the case that embodiments of the present invention achieve maximum/optimal press fit fixation (BFSF) short of full insertion (i.e., intentional presence of a polar gap).

There may be advantages to reducing polar gaps, and rather than full insertion, a modification to the prosthesis may include a truncated hemisphere (snub nosed) cup 1510. There is a desire to reduce insertion forces while maximizing press fit fixation. Evolution of the prosthesis may incorporate several different ideas, including asymmetric deformation control using a truncated cup with longitudinally extending ribs 1515 and laterally extending planks 1520—the combination of ribs and planks cup 1525 may produce an asymmetric deformation to improve installation (such as making it easier to install and more difficult to remove). Further, a perimeter of an improved cup may include a discrete polygon having many sides. The reduced surface area contacting the prepared cavity may reduce force needed to install while the vertices of the polygon may provide sufficient press-fit fixation. Cup 1525 may include tuned values of the snub, different stiffnesses of ribs and planks, a perimeter configuration of the regular/irregular non-hemispherical polygonal outer surface. These vertices themselves may be angular and/or rounded, based upon design goals of a particular implementation of an embodiment to achieve the desired trade-offs of installation efficiency and press-fit fixation to improve the possibility of achieving BFSF.

These concepts have implications on how the acetabular (all press fit prosthesis) prosthesis are made. If it holds true that the dome of the cup mostly acts like a wedge to cause fracture, it may be best to eliminate the dome (flatten the cup) and change the geometry of the cup to be more like a frustum polygon with an N number of sides, or a hemisphere with a blunted dome.

A. With the ability to provide a proportional amount of force for any particular (implant/bone) interface, we can expect to use just the right amount of force for installation of the prosthesis (not too much and not too little). Additionally we have previously in U.S. patent application Ser. No. 15/234,927, expressly incorporated herein, discussed methods to manufacture prosthesis with an inherent tendency for insertion, MECHANICAL ASSEMBELY INCLUDING EXTERIOR SURFACE PREPAREATION. Specifically, we have descried the concept of two-dimensional stiffness incorporated within the body of the prosthesis, which would produce a bias for insertion due to the concept of undulatory motion, typically observed in Eel and fish skin.

FIG. 15 includes a side view of a prosthesis including a two-dimensional asymmetrical stiffness configuration, and illustrates a top view of prosthesis. The prosthesis may include a set of ribs and one or more planks disposed as part of a prosthetic body, represented as an alternative acetabular cup. The body may be implemented in conventional fashion or may include an arrangement consistent with prosthesis P. The ribs and plank(s) are configured to provide an asymmetric two-dimensional (2D) stiffness to body that may be more conducive to transmission of force and energy through the longitudinal axis of the cup as opposed to circumferentially. Ribs are longitudinally extending inserts within body (and/or applied to one or more exterior surfaces of body). Plank(s) is/are laterally extending circumferential band(s) within body (and/or applied to one or more exterior surfaces of body). For example, planks may be "stiffer" than ribs (or vice-versa) to produce a desired asymmetric functional assembly that may provide for an undulatory body motion as it is installed into position.

Based on our understanding of the acetabular prosthesis/ bone interface in our Invasive sensing studies in one or more incorporated patent applications and in conjunction with the incorporated '927 application of MECHANICAL ASSEMBELY INCLUDING EXTERIOR SURFACE PREPAREATION, we anticipate that the prosthesis of the future may have different characteristics.

A. The acetabular component may be shaped more like a frustum with Nth (e.g., 160 sides) and an amputated dome. The snubbed dome of the new prosthesis would not engage the acetabular fossa (Cotyloid fossa) allowing the new prosthesis fully to engage the stronger acetabular walls/rim (constituted by the ilum, ischium and pubic bones). This shape of prosthesis avoids the possibility of a wedge type fracture which can be produced by the dome of a hemispherical implant.

B. Each angle of the frustum may produce longitudinal internal rib extending from the rim distally, (developed within the structure of the prosthesis by additive manufacturing by controlling the material properties of crystalline metal), that is more flexible than the horizontal stiffer planks that extend from the rim to the snub distally in a circumferential fashion. (See the incorporated '927 application). This shape of prosthesis will have a strong bias for insertion due to undulatory motion, and will require less force for installation.

Permanent or Removable Sensors on the Surface of the Prosthesis.

A. As described herein, in some experiments that when F2 approaches F1, that in fact F1=F2=F3=F5. That is, when the implant/bone collision becomes elastic, the resistive force at the interface F3 and the forces felt in bone F5 can be inferred from applied force F1 and force felt in tool F2. This can provide the surgeon valuable information about the forces she is imparting to the bone. We also contemplate that F3 and F5 can be directly measured by application of mechanical and biologic sensors directly on a sensing prosthesis 1530. We believe given the mass production and ubiquitously available sensors, at some point, the prosthesis of the future would be equipped with its own sensor (biologic and or mechanical) to convey to the surgeon the forces being imparted into the bone, to prevent excessive forces on bone, as well as to prevent loose fitting prosthesis. Sensors on the applied on the surface of the prosthesis to measure interface or dome pressure (F3 or F5) can be permanent or removable i.e., a slot on the side of the prosthesis can allow incorporation of a small sliding sensor to provide information about the interface to the system. Examples of incorporated sensors, one or more which may be used, may include an internal sensor 1535, a mechanical sensor 1540, a biologic sensor 1545, and an external sensor 1550.

B. Data Fusion of F2, F5, F3 for most sensitive evaluation of stress response of Bone at the Implant Bone Interface— multiple parameters are weighted and merged or fused that may provide a robust parameter offering improved performance over reliance on a single parameter.

2. Application of Force Based on a Sensory (not Visual) Evaluation of Implant/Bone Interface.

A. For years surgeons have applied uncontrolled force to impact prosthesis into bone, and have assessed the quality of insertion by human visual, tactile and auditory means. More recently surgeons have begun to use visual tracking means such as fluoroscopy, computer navigation (including Nikou), and MAKO techniques to assess depth of insertion. We are the first to suggest that the application of force for installation of prosthesis should be predicated on the force sensing activity of the prosthesis/bone interface. This is a new technique that predicates application of force for installation of prosthesis to be based (NOT VISUAL TRACKING MEANS—depth of insertion) but rather (FORCE SENSING MEANS OF THE INTERFACE—proof resilience). This is a novel concept that will eliminate too tight and too loose press fit fixation of all prosthesis, and associated problems such as subsidence, loosening, and infection.

Figure 16:
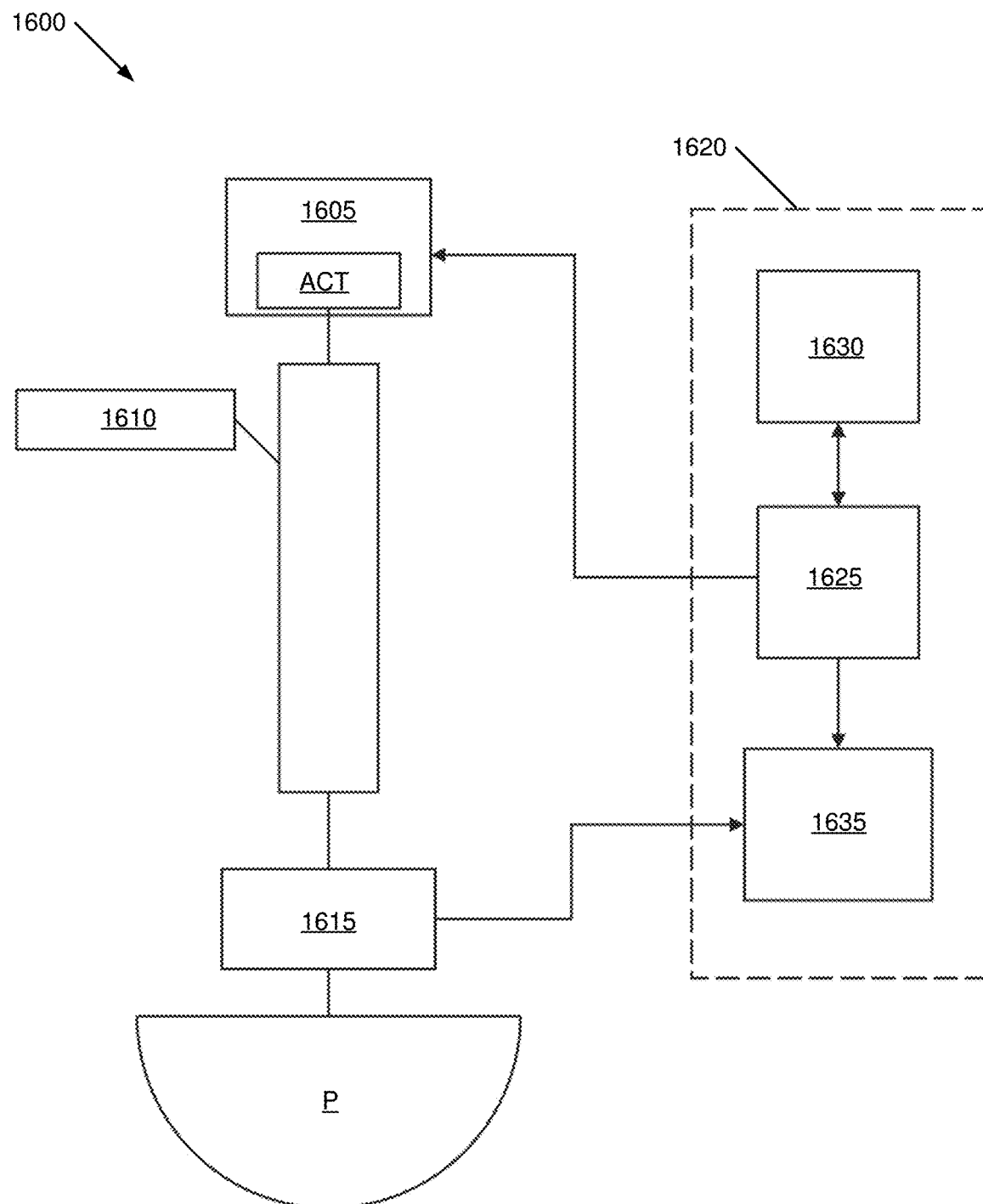
FIG. 16 illustrates a particular embodiment of a $BMD_X$ force sensing tool.

FIG. 16 illustrates a particular embodiment of a $BMD_X$ force sensing tool 1600. Tool 1600 allows indirect measurement of a rate of insertion of an acetabular cup and may be used to control the impact force being delivered to a prosthesis based upon control signals and the use of features described herein. Tool 1600 may include a controllable force applicator (e.g., an actuator) 1605, an impaction transfer structure 1610 (e.g., impaction rod), and a force sensor 1615.

Applicator 1605 may include a force sensor to measure/ determine F1 (in some cases applicator 1605 may be designed/implemented to apply a predetermined and knowna priori force.

Structure 1610 transfers force as an insertion agency (for prosthesis implant applications) to prosthesis P and sensing system 1615 measures a realtime (or near realtime) force response of prosthesis P to the insertion agency while it is being implanted into the implant site. There are many different possible force response mechanisms as described herein. For example, F2, F3, F5, and first/second order derivatives and combinations thereof as noted herein. In some cases, sensing system 1615 may include in-line or external sensor(s) associated with or coupled to structure 1610. In other cases, some embodiments of system 1615 may include sensor(s) associated with the bone or cavity or other aspect of the cavity, prosthesis, cavity/prosthesis interface or other force response parameter. System 1615, as noted herein, may include multiple concurrent sensors from different area including one or more of tool, prosthesis and bone/cavity.

One representative method for force measurement/response would employ such a tool 1600. Similar to the impaction rod currently used by surgeons, tool 1600 may couple to an acetabular cup (prosthesis P) using an appropriate thread at the distal end of structure 1610. Applicator 1605 may couple to a proximal end of structure 1610, and create an insertion agency (e.g., controlled and reproducible impacts) that would be applied to structure 1610 and connected cup P. A magnitude of the impact(s) would be controlled by the surgeon through a system control 1620, for example using an interface such as a dial or other input mechanism on the device, or directly by the instrument's software. System control 1620 may include a microcontroller 1625 in two-way communication with a user interface 1630 and receiving inputs from a signal conditioner 1635 receiving data from force sensing system 1615. Controller 1625 is coupled to actuator 1605 to set a desired impact profile including a set of force applications that may change over time as described herein.

Sensing system 1615 may be mounted between structure 1610 and acetabular cup P. System 1615 may be of a high enough sampling rate to capture the peak force generated during an actuator impact. It is known that for multiple impacts of a given energy, the resulting forces increase as the incremental cup insertion distance decreases/

This change in force given the same impact energy may be a result of the frictional forces between cup P and surrounding bone of the installation site. An initial impact may have a slow deceleration of the cup due to its relatively large displacement, resulting in a low force measurement. The displacement may decrease for subsequent impacts due to the increasing frictional forces between the cup and bone, which results in faster deceleration of the cup (the cup is decelerating from the same initial velocity over a shorter distance). This may result in an increase in force measurement for each impact. A maximum force for a given impact energy may be when the cup P can no longer overcome, responsive to a given impact force from the actuating system, the resistive (e.g., static friction) forces from the surrounding bone. This results in a "plateau", where any subsequent impact will not change either the insertion of cup P or the force measured.

In some embodiments, this relationship may be used to "walk up" the insertion force plot, allowing tool 1600 to find the "plateau" of larger and larger impact energies. By increasing the energy, the relationship between measured impact force and cup insertion should hold until the system reaches a non-linear insertion force regime. When the non-linear regime is reached, a small linear increase in impact energy will not overcome the higher static forces needed to continue to insert the cup. This will result in an almost immediate steady state for the measured impact force (mIF of a force application X is about the same as MIF of a force application X+1).

A procedure for automated impact control/force measurement may include: a) Begin operation of an insertion agency with a static, low energy; b) Record the measured force response (MIF); c) continue operation of the insertion agency until the difference in measured impact force approaches zero (dMIF=>0), inferring that the cup is no longer displacing; d) increase the energy of the operation of the insertion agency by a known, relatively small amount; and e) repeat operation of the modified insertion agency until plateau and increasing energy in a fashion (e.g., a linear manner) until a particular plateau patterning is detected. Instead, an increase in energy results in a "step function" in recorded forces, with an immediate steady-state. The user could be notified of each increase in energy, allowing a decision by the surgeon to increase the resulting impact force.

A goal of a validated ISM concept is to produce a sophisticated tool for a surgeon that provides automatic, intelligent prosthesis installation, with the capacity to provide access to an optimal best fixation short of fracture (BFSF) endpoint inherent in any implant/cavity system. This tool will allow surgeons of all walks of life, regardless of level of experience, to obtain the best possible press fit fixation of any cup/cavity system, without fear of too loose or tight press fit, as well as obviating the need for screw fixation with all its attendant problems.

The tool may include a handheld pneumatic instrument with a sliding mass component. It may have the following features: 1) ability to deliver precisely controlled axial impacts of known impact energy E, 2) ability to increase or modify applied force (F1) over the course of use, 3) ability to acquire the resulting F1, F2, F3, and F5 for each impact, 4) ability to automatically control the application of impact energy to optimally seat an acetabular cup (implant) using the algorithms determined in Phase I, 5) communicate data pertaining to ISM and BFSF to the surgeon, 6) allow for manual override and selection of impact energy by the surgeon.

Actuators of applicator 1605 may include a one or more of a wide variety of devices (or combinations thereof), including pneumatic actuators, electro-magnetic actuators, spring-loaded masses, and the like.

The device may have industry standard interfaces in order to allow for use with a variety of cup models. For the example implementation, the impact energy is controlled through a piston actuation control mechanism and by additional adjustments of sliding mass and travel distance. Once a final actuation method is selected, a working prototype will be designed and fabricated to allow for controlled insertion of acetabulum cups.

The instrument may be equipped with inline force sensors and wireless connectivity in order to determine resulting forces F1, F2, F3, F5 within the system. Applied force F1 and felt force within the tool (F2) will be measured using internal sensors, whereas the forces felt in bone (F5) and at the implant/bone interface (F3) will be measured separately with appropriately placed sensors in the system and the data conveyed to the central processing unit (CPU) through wireless (intranet) systems.

The tool will be controlled by integrated electronics that provide analysis of the inter-relationships between F1, F2, F3, F5 with respect to number of impacts (NOI) to full insertion, and impact energy. The magnitude of the impacts will be controlled by a CPU (FIG. 16) and associated software, where the system control may include a microcontroller in two-way communication with a user interface and receive inputs from a signal conditioner, which receives data (directly or indirectly) from the sensors within the system. The microcontroller will be coupled to the actuator to set a desired impact energy and run a fixation algorithm to obtain endpoint BFSF.

Programmed algorithms based on the binary decision system described in Phase I Specific Aim #1 will produce successive impacts of known energy, making two simultaneous decisions before each impact: 1. Continue applying force or not, and if so, then 2. Increase energy or not. These binary decisions will be based on parametric values produced by the control electronics, which provide essential feedback of the implant/bone interface, and the elastic response of bone at the aperture. The following algorithm provides a basic example of the binary "fixation algorithm" to be incorporated in the control mechanism: (i) apply energy E1 and measure F2, NOI, ΔF2; (ii) monitor F2 over NOI, and/or monitor ΔF2 as it approaches 0; (iii) when ΔF2 approaches 0, insertion is not occurring for that particular energy E1. If NOI required to achieve this point is sufficiently large (low rate of insertion), as determined by the control algorithm, then E1 is increased to E2; (iv) continue steps (i) through (iii) until the NOI required for ΔF2 to approach 0 is sufficiently small (high rate of insertion), as determined by the control algorithm; (v) the sophisticated tool will not generate automated impacts after this level is reached. Additional increase in energy E is not recommended but can be produced manually at the surgeon's discretion. No more than one incremental manual increase is recommended.

As noted earlier, our preliminary data indicate that force measurements directly at the interface (F3), and in bone (F5) will show similar trends and characteristics as F2, such that although independent, they may be considered redundant, complimentary and/or cooperative. We expect to be able to incorporate these data into an independent system architecture and utilize existing data fusion algorithms to potentially produce a higher resolution evaluation of the stress (force) field around the implant/bone interface than with each individual sensor alone.

Validation of the tool will be performed at Excelen and at the University of Minnesota Department of Engineering by comparing the quality of insertion (extractive force F4) produced by AI-PID—which automatically achieves endpoint BFSF—with the quality produced by a mallet and standard impaction techniques accomplished by a board certified orthopedic surgeon blinded to the study. Specifically, the two distinct endpoints of 1. BFSF (achieved through AI-PID) and 2. Full Seating (achieved through mallet strikes) will be compared to determine differences in F4 and fracture incidence. All parameters associated with these two endpoints will be compared and evaluated. Specifically, a risk benefit analysis will be performed to determine whether higher impact energies were required to obtain full seating, and if so, whether the additional impacts provided any significant value as to CI or F4, and whether there was any increase in fracture incidence (failure of the cavity) with either technique.

Interpretation of Results:

Measurements of F2 and ΔF2 and their first and second order derivatives and comparative analysis with respect to NOI to insertion may provide a principled and organized process for application of energy to achieve the desired optimal endpoint BFSF. It is anticipated that the second order relationship of ΔF2 to NOI, alternatively stated as the rate of decay of ΔF2 (how fast ΔF2 approaches 0) may provide an evaluation of elastic/plastic deformation and also contribute to achieving BFSF.

Biology of Graft Healing

Tendon graft healing to a bone tunnel is one important factor affecting a success of a reconstructed ACL. An unruptured ACL attaches to bone through "direct" type insertion, which has a highly differential morphology including four specific zones: tendon, fibrocartilage, mineralized fibrocartilage, bone. This small 1 mm zone plays an important mechanical role in allowing progressive distribution of tensile loads from the tendon (ligament) to subchondral bone.

A reconstructed ACL may sometimes attach to bone in a different fashion called "indirect" type insertion, which has a significantly simpler ultrastructure. Indirect insertion involves anchoring of the tendon (ligament) into bone without the intervening fibrocartilaginous zones (non-mineralized and mineralized fibrocartilage). These fibers represent the type of anchoring that occurs between periosteum and bone referred to as Sharpey fibers. The design of this type of insertion allows for micro motion at the insertion site. It is not as efficient as the "direct" type insertion in allowing transition of mechanical forces from ligament to bone.

Problem—Suspensory Cortical Fixation Versus Aperture Interference Screw Fixation There are broadly two types of fixation: suspensory cortical fixation and aperture interference screw fixation. There is general consensus that there are advantages and disadvantages to each method of fixation.

Suspensory Cortical Fixation

Figure 17:
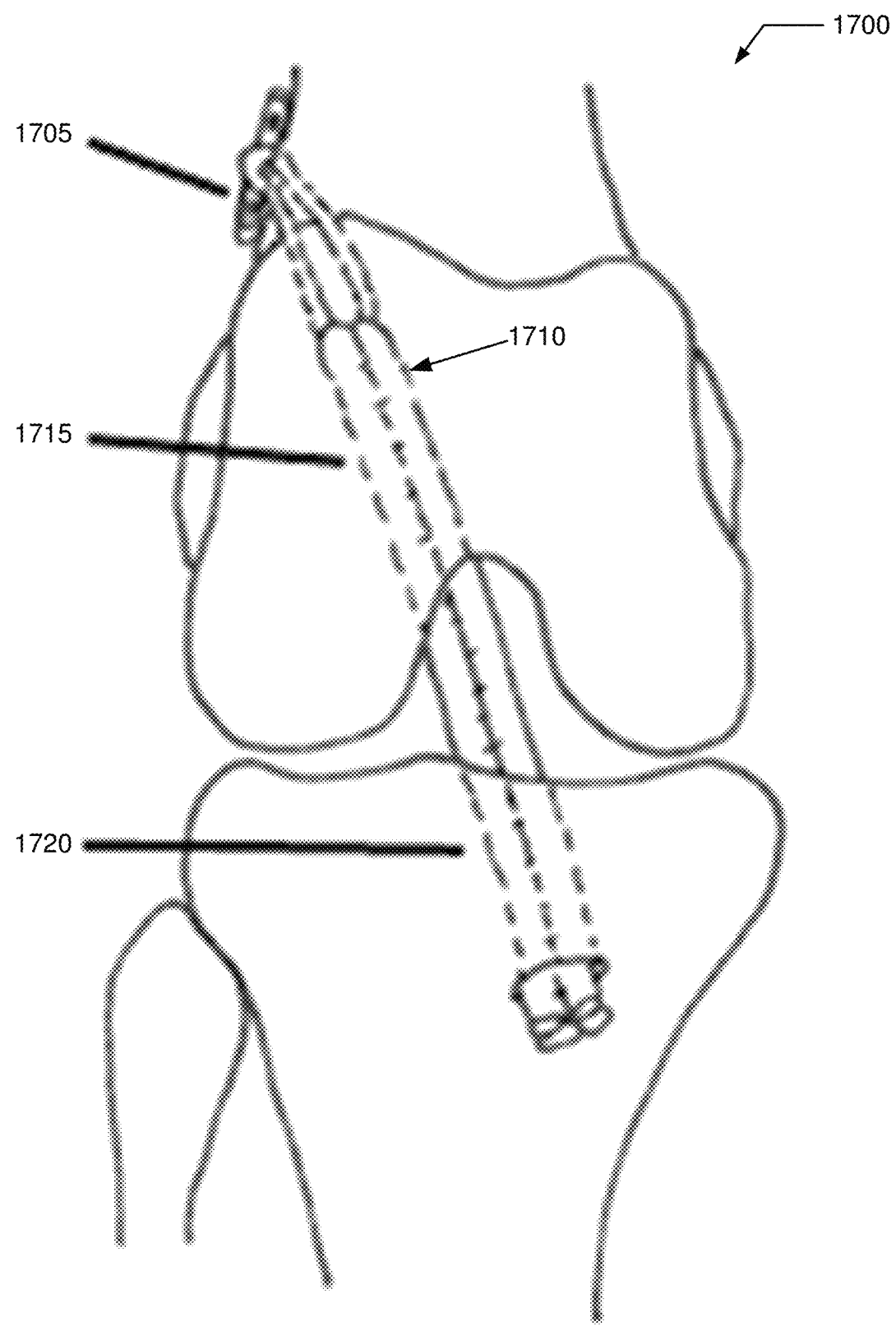
FIG. 17 illustrates an example of suspensory cortical fixation.

FIG. 17 illustrates an example of suspensory cortical fixation 1700. Fixation 1700 includes an endobutton 1705 supporting a graft 1710 through a femoral tunnel 1715 and a tibial tunnel 1720.

Advantages of fixation 1700 may include one or more of: (a) allows circumferential 360 degree contact between tendon and bone (maximized surface area contact for tendon to bone healing); (b) easier operation to perform; (c) less damage to bone and tendon at the time of surgery (less invasive—bone and tendon sparing); and (d) strong fixation.

Disadvantages of fixation 1700 may include one or more of: (a) allows micro motion at the aperture, including (i) bungee effect (lengthwise micro motion), (ii) windshield wiper (side-to-side micro motion), and/or (iii) increased propensity for increased risk of poor healing such as tunnel widening; (b) low tendon to bone compression forces at the interface (less than ideal healing: always heals with "indirect" type healing (Sharpey Fibers, no transitional zone of mineralized and non-mineralized fibrocartilage).

Aperture Interference Screw Fixation

Figure 18:
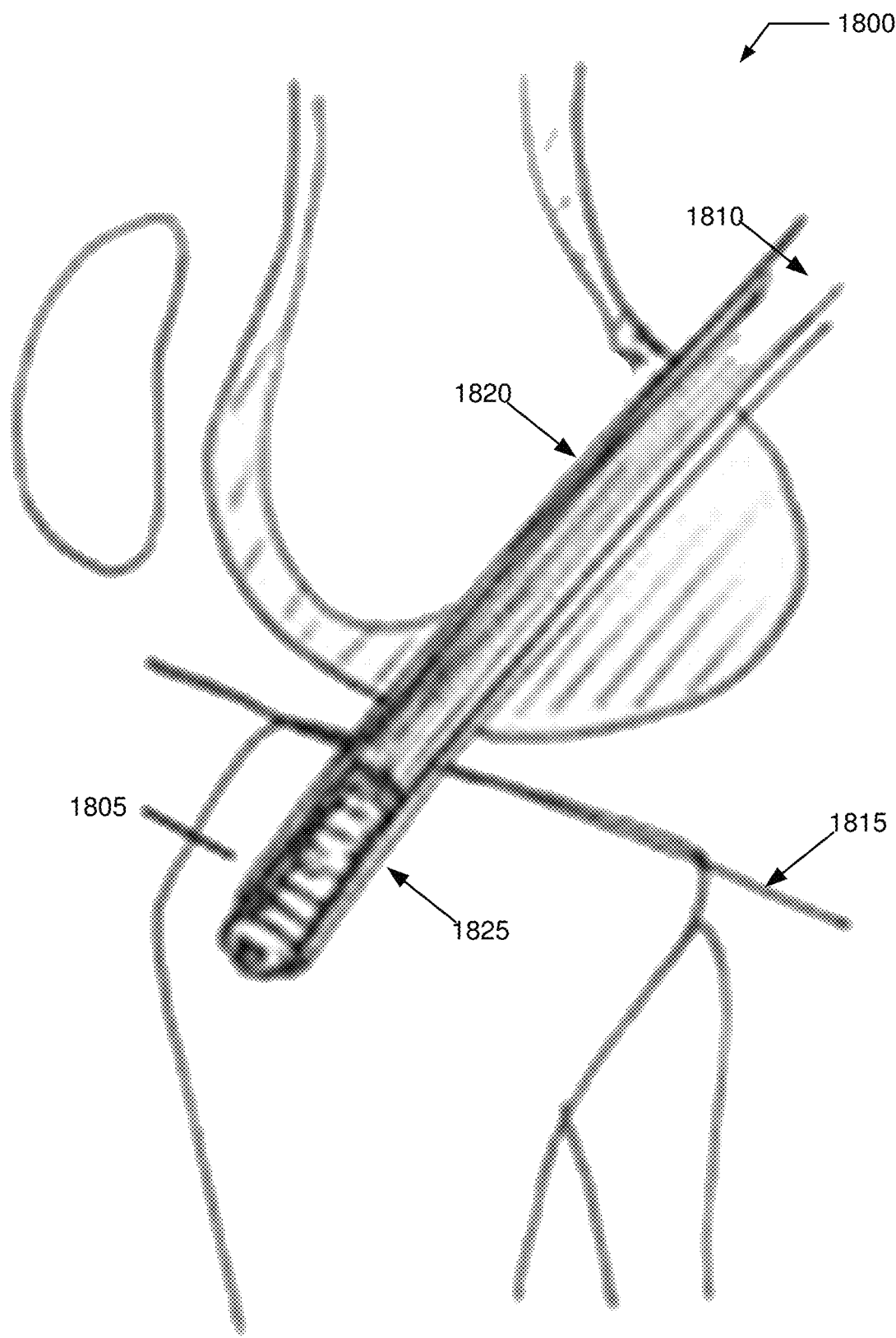
FIG. 18 illustrates an example of aperture interference screw fixation.

FIG. 18 illustrates an example of aperture interference screw fixation 1800. Fixation 1800 includes an interference screw 1805 attached to a graft 1810 that has the relationship illustrated between a tibial plateau 1815 and Blumensaat's line 1820 along with a tibial tunnel 1825 wherein screw 1805 is applied.

Advantages of fixation 1800 may include one or more of: (a) significantly higher compression forces between tendon/bone interface (by an order of magnitude) relative to fixation 1700; (b) rigid fixation with minimal or no micro motion in the bone tunnel; (c) ideal healing—graft 1810 heals to bone by "direct" type insertion with much higher specialization of the tendon bone interface, allowing for progressive force transfer from tendon to bone (formation of the four zones: tendon, fibrocartilage, mineralized fibrocartilage, bone); and (d) faster healing.

Disadvantages of fixation 1800 may include one or more of: (a) significant tissue damage to the graft and bone with interference screw fixation (weakening of the early fixation period—6 to 10 weeks); (b) loss of circumferential contact between tendon and bone, compromising maximal contact area between tendon and bone by at least 50%; and (c) inflammatory and cellular reaction to foreign body within the tunnel causing tunnel widening and cyst formation.

The present invention may be useful for a wide-range of connective tissue grafts used in a wide-range of repair techniques. With this understanding, to simplify the discussion a particular type of graft used in a particular type of repair technique: an ACL graft used for repair of a ruptured ACL.

The knee is a simple hinge joint at the connection point between the femur and tibia bones. It is held together by several important ligaments. The most important of these to the knee's stability is the Anterior Cruciate Ligament (ACL). The ACL attaches from the front part of the tibia to the back part of the femur. The purpose of this ligament is to keep the tibia from sliding forward on the femur. For this reason, the ACL is most susceptible to injury when rotational or twisting forces are placed on the knee. Although this can happen during a contact injury many ACL tears happen when athletes slow down and pivot or when landing from a jump.

After the ACL is torn the knee is less stable and it becomes difficult to maintain a high level of activity without the knee buckling or giving way. It is particularly difficult to perform the repetitive cutting and pivoting that is required in many sports.

Regardless of how the ACL is torn a physician will work with their patient to determine what the best course of treatment will be. In the case of an isolated ACL tear (no other ligaments are involved) the associated pain and dysfunction may often be successfully treated with rest, anti-inflammatory measures, activity modification and Physical Therapy. After the swelling resolves and range of motion and strength is returned to the knee a decision can be made as to how to proceed. Many people elect to use a sports brace and restrict their activity rather than undergo surgery to reconstruct the ACL. When a non-surgical approach is taken the patient must understand that it is imperative that she or he maintain good strength in her or his leg and avoid sports or activities that require pivoting or cutting. When conservative measures are unsuccessful in restoring function the patient and their physician may elect to have the torn ligament reconstructed.

ACL reconstruction surgery is not a primary repair procedure. This means that the ligament ends cannot simply be sewn back together. The new ACL must come from another source and grafted into place in the knee. There are a few different options as to what tissue is used for the ACL graft (three most common sources include patella tendon, hamstring tendon, and cadaver tendon) and each patient should consult with his or her surgeon to determine the best choice. During the procedure a set of tunnels are drilled within the tibia and femur and the new ACL graft is passed into these tunnels and anchored into place. Some or all of this anchoring, in embodiments of the present invention, occur by use of an in situ decompression of a compressed end portion of the ACL graft within a prepared tunnel.

The ACL graft includes a highly hydrated and compressible tissue. As observed by applicant, a diameter of a typical ACL graft may be compressed, for example by up to 2 to 4 millimeters, with special techniques that can be employed just prior to installation. The native ACL graft can be manipulated (e.g., compressed and/or stretched) to produce a manipulated ACL graft that has a smaller diameter than the native ACL graft. For this discussion, the native ACL graft may include a 10 millimeter diameter while the manipulated ACL graft may include a 7 millimeter diameter.

The manipulated ACL may subsequently be implanted at a significantly compressed diameter than its original form (i.e. 7 mm instead of 10 mm) and allowed to expand, in a delayed fashion, within bone tunnels formed and used during the repair procedure, producing high contact forces at an interface between the manipulated ACL graft and the bone of the tunnel (e.g., a tendon/bone interface).

This repair may be accomplished with all the positive attributes of suspensory cortical and aperture fixation and without any of the negative attributes of the two fixation methods.

This method of "biological press fit" fixation does not have the negative attributes of interference screw fixation including: without the use of an interference screw and its attendant negative attributes including: (i) damage to the graft and bone; (ii) loss of circumferential contact; and (iii) foreign material within the tunnels causing late inflammatory and destructive reactions in bone. Similarly, the "biological press fit" fixation dos not have the negative attributes of suspensory cortical fixation including: (i) micro motion at the aperture causing bungee (lengthwise micro motion) and windshield wiper (side-to-side micro motion) effects, (ii) increasing risk of tunnel widening; and (iii) low tendon-bone interface compression forces leading to "indirect" type healing (Sharpey Fibers, with no transitional zone of mineralized and non-mineralized fibrocartilage, for specialized transfer of force).

An embodiment of the present invention may allow all the positives attributes of both suspensory cortical and aperture fixation. "Biologic press fit" fixation may embody all the positive attributes of suspensory cortical fixation including: (i) circumferential 360-degree contact between tendon and bone (maximized surface area contact for tendon to bone healing); (ii) easier operation to perform; (iii) less damage to bone and tendon at the time of surgery (less invasive—bone and tendon sparing); (iv) strong fixation. "Biological press fit" fixation similarly may embody all the positive attributes of aperture fixation including: (i) significantly higher compression forces between tendon/bone interface; (ii) rigid fixation with minimal or no micro motion in the bone tunnel; (iii) ideal healing—by "direct" type insertion with specialization of the tendon bone interface, allowing for progressive force transfer from tendon to bone (formation of the four zones: tendon, fibrocartilage, mineralized fibrocartilage, bone); and (iv) faster healing.

The combination of factors noted above are believed to allow high interference forces that may be obtained soon after implantation (including decompression of manipulated ACL graft within a portion of a one tunnel), these interference forces due to the in situ decompression of the manipulated ACL graft, without interference of foreign material within the tunnels.

Some embodiments may include application of one or more remotely-readable biological sensors to the manipulated ACL graft. The sensors may, for example, include a capacity to measure contact forces at the tendon/bone interface of the expanding manipulated ACL graft within a tunnel. These sensors may be applied to the ACL graft as part of the preparation or provided to the surgeon prior to compression. There may be various uses of this/these sensor(s), in order to assess compressive forces produced at the tendon/bone junction at time zero and over defined periods of time.

Figure 19:
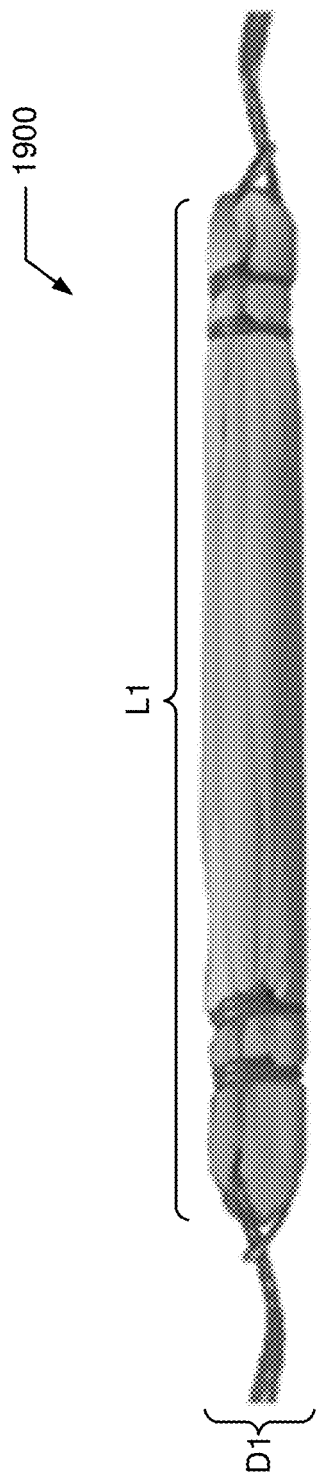
FIG. 19 illustrates an example of a native connective tissue graft.

FIG. 19 illustrates an example of a native connective tissue graft 1900. Graft 1900 is provided with predetermined general dimensions, including a length L1 and a diameter D1. For example, for an ACL reconstruction, graft may have L1 about 90-180 millimeters (determined by patient anatomy) and D1 about 10 millimeters.

Figure 20:
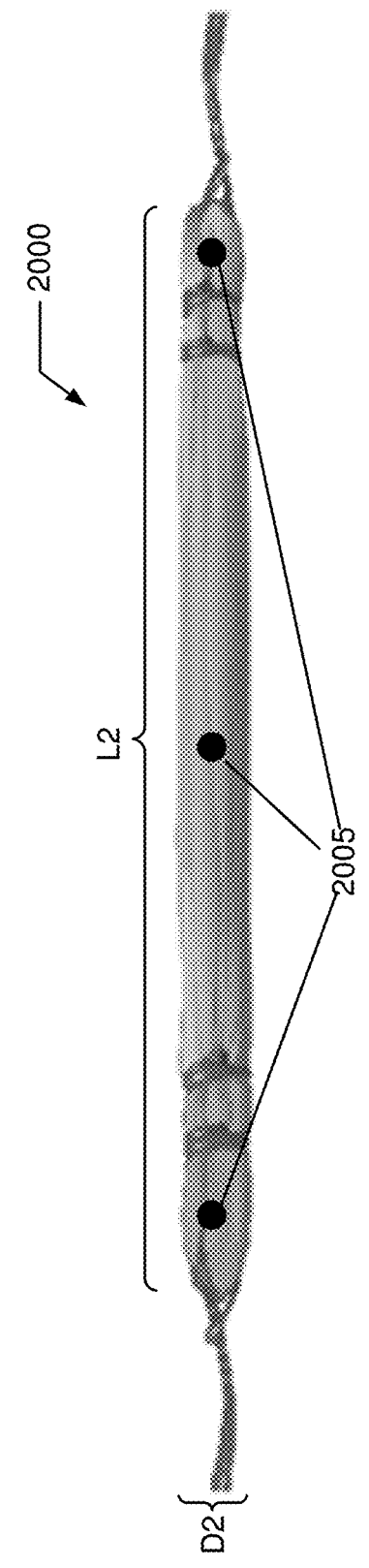
FIG. 20 illustrates an example of a compressed connective tissue graft that may result from a pre-operative compressive treatment of the native connective tissue graft of FIG. 19.

FIG. 20 illustrates an example of a compressed connective tissue graft 2000 that may result from a pre-operative compressive treatment of native connective tissue graft 1900. Graft 2000 includes a length L2 that may be about greater than or equal to L1 and further includes a diameter D2 that is less than D1. One or more remotely-readable biologic sensors 2005 may be included with graft 2000.

Sensor(s) 2005 may be included as part of graft 1900 (pre-manipulation) or may be applied to a surface of graft 2000 or bulk-integrated into a body of graft 2000 as part of, or attendant to, pre-reconstruction preparation of graft 2000.

Sensor(s) 2005 may be used for different purposes to assess a quality of various aspects of the reconstruction procedure. For example, a compression reading at one or more interfaces between one or more end portions of graft 2000 within the bone tunnel into which graft 2000 was installed may be used to measure healing and fixation. A sensor 2005 disposed outside of a tunnel between the femur and the tibia may include a stress-strain gauge to understand the potentially rupturing forces that the patient applies to the reconstructed ACL graft (after surgery) in the course of their activities. Readings may be taken immediately after installation and then at various subsequent times to assess a magnitude of the graft/bone interface at that/those portion(s). The readings may indicate that healing is progressing (and some metric of how well the healing has progressed), healing has largely completed past a predetermined threshold, or that there may be some complication in the healing process.

Figure 21:
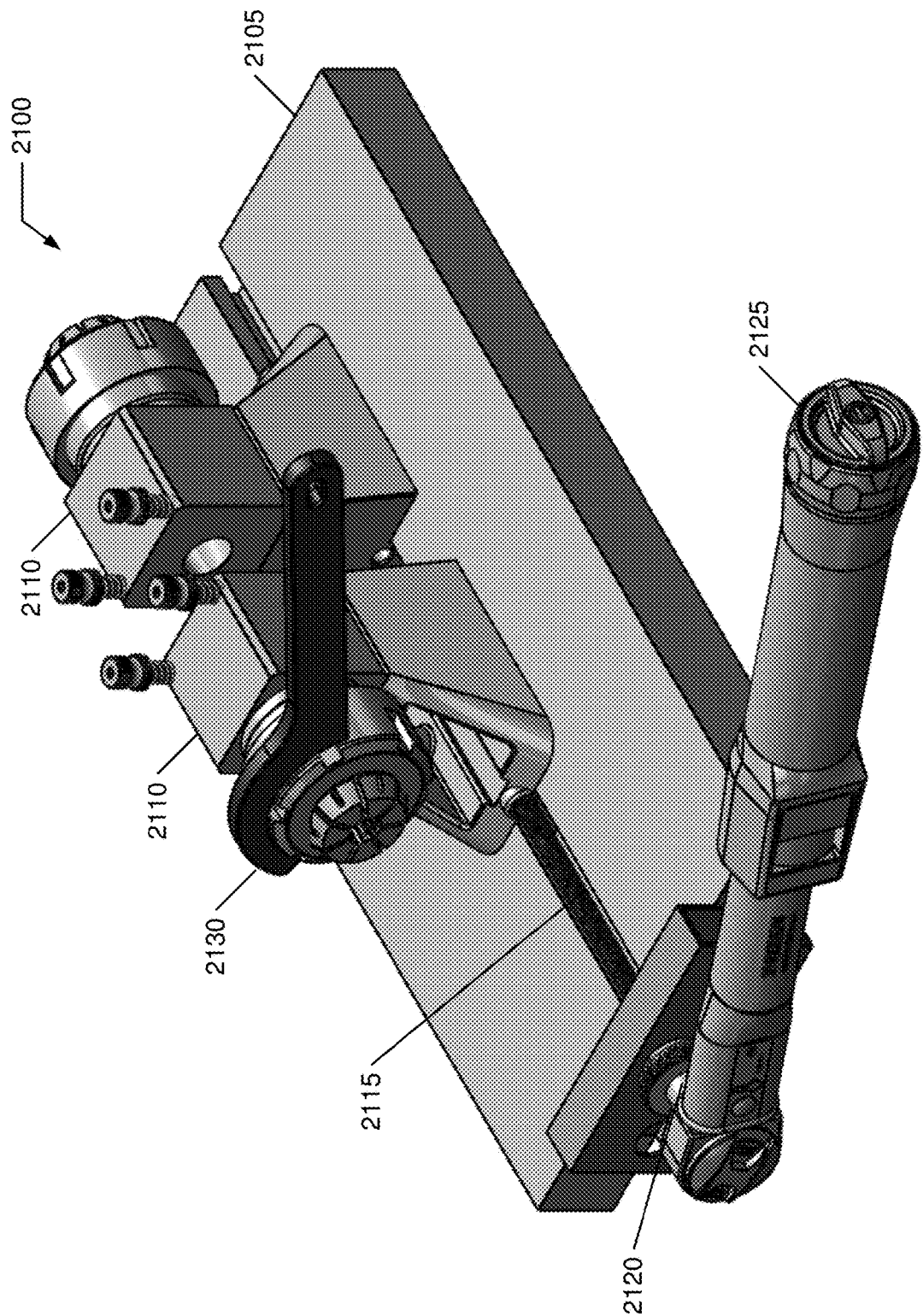
FIG. 21 illustrates a perspective view of a graft platform.

FIG. 21 illustrates a perspective view of a graft platform 2100. Platform 2100 may include a table 2105 supporting a pair of moveable sleeve housings 2110. Housings 2110 move relative to each other (one or both housings 2110 may move). Movement may be controlled by a drive rod 2115 having a knob 2120. Knob 2120 may be turned using a torque wrench 2125 to understand how much force is being used to separate housings 2110. One may want to be sure that not too small or too large force is used in separating housings 2110 as this influences an amount of tension/deformation to any graft being manipulated by platform 2100.

Each housing 2110 supports a graft sleeve that defines a conical internal sleeve structure into which a collet chuck is introduced and upon which a collet nut is threaded over the collet chuck within the internal sleeve structure using complementary threaded portions of an end of the graft sleeve. A wrench 2130 may be used to tighten the collet nut onto the graft sleeve. One or more suture holders may be used to support graft 1900 when initially installed into graft platform 2100. For purposes of this illustration FIG. 21, sleeve housings 2110 are shown facing away from each, while in actual operation housings 2110 are reversed as illustrated in FIG. 22.

Figure 22:
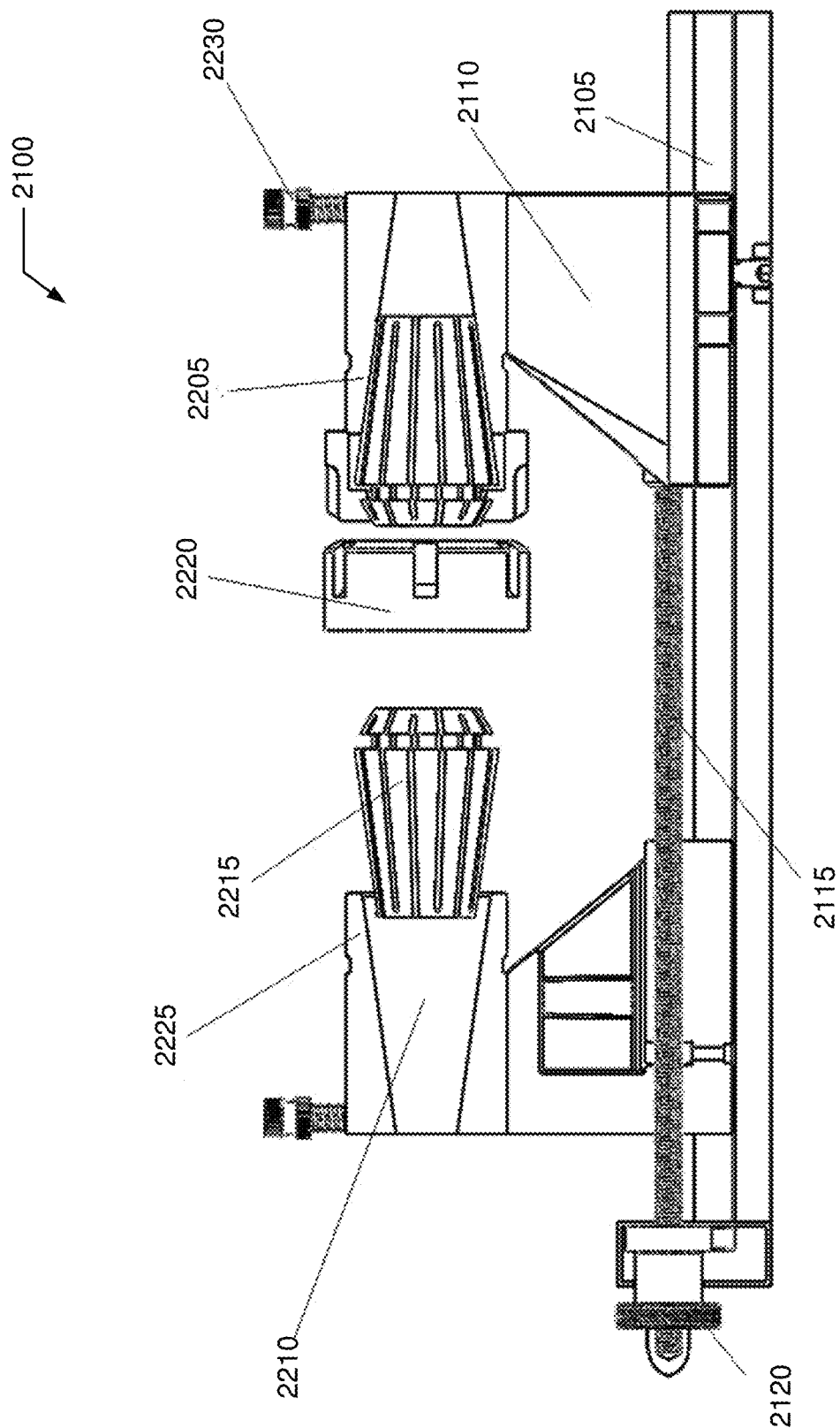
FIG. 22 illustrates a side view of the graft platform of FIG. 21 with repositioned stages.

FIG. 22 illustrates a side view of graft platform 2100 with repositioned housings 2110 to face each other. Platform 21500 includes a graft sleeve 2205 coupled to housing 2110. Each graft sleeve 2205 defines a conical internal sleeve structure 2210 into which a collet chuck 2215 is positioned. A threaded collet nut 2220 is positioned over collet chuck 2215 and is installed onto sleeve 2205 by use of a threaded end 2225 of graft sleeve 2205. Each graft sleeve 2205 includes one or more suture holders 2230.

In operation, graft 1900 is installed into graft platform 2100 with each sleeve 2205 gripping one end. There are different possible operational modes for graft platform 2100 to compress graft 1900 and produce graft 2000, depending upon the procedure agreed upon by the patient and surgeon.

Graft platform 2100 may compress some or all of graft 1900 by applying equal lateral compressive forces along its length (by appropriate positioning and tightening of collet chucks 2225 into structures 2210 using nut 2220 and/or separating housings 2110 from each other using knob 2120 to rotate rod 2115.

Figure 23:
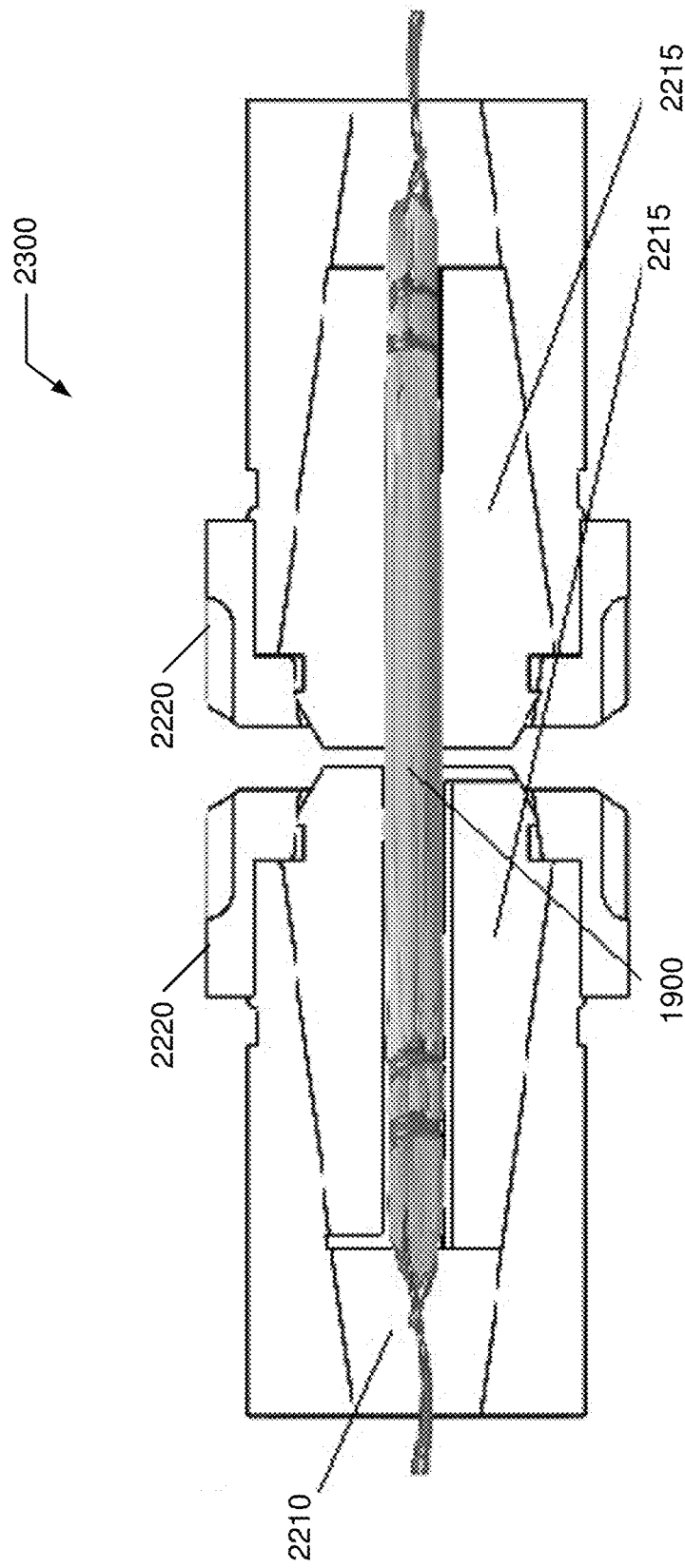
FIG. 23 illustrates a sectional view of a pair of collets gripping the native connective tissue graft of FIG. 19.

FIG. 23 illustrates a sectional view 2300 of a pair of collet chucks 2215 of platform 2100 gripping native connective tissue graft 1900 by being forced into structure 2210. Each collet chuck 2215 includes a longitudinal tunnel having a variable diameter. That diameter is greatest when it is initially installed into structure 2210. As nut 2220 is tightened, such as with wrench 2130, the corresponding chuck 2215 is forced deeper into conical structure 2210 which decrease the diameter of the longitudinal tunnel. Decreasing the longitudinal tunnel while a portion of graft 1900 is installed is one manner by which lateral compressive forces may be applied to that portion of graft 1900 (which decreases the diameter of that portion of graft 1900). Chuck 1915 may be designed to have a physically-determined minimum diameter to help ensure that graft 1900 is not excessively compressed.

Figure 24:
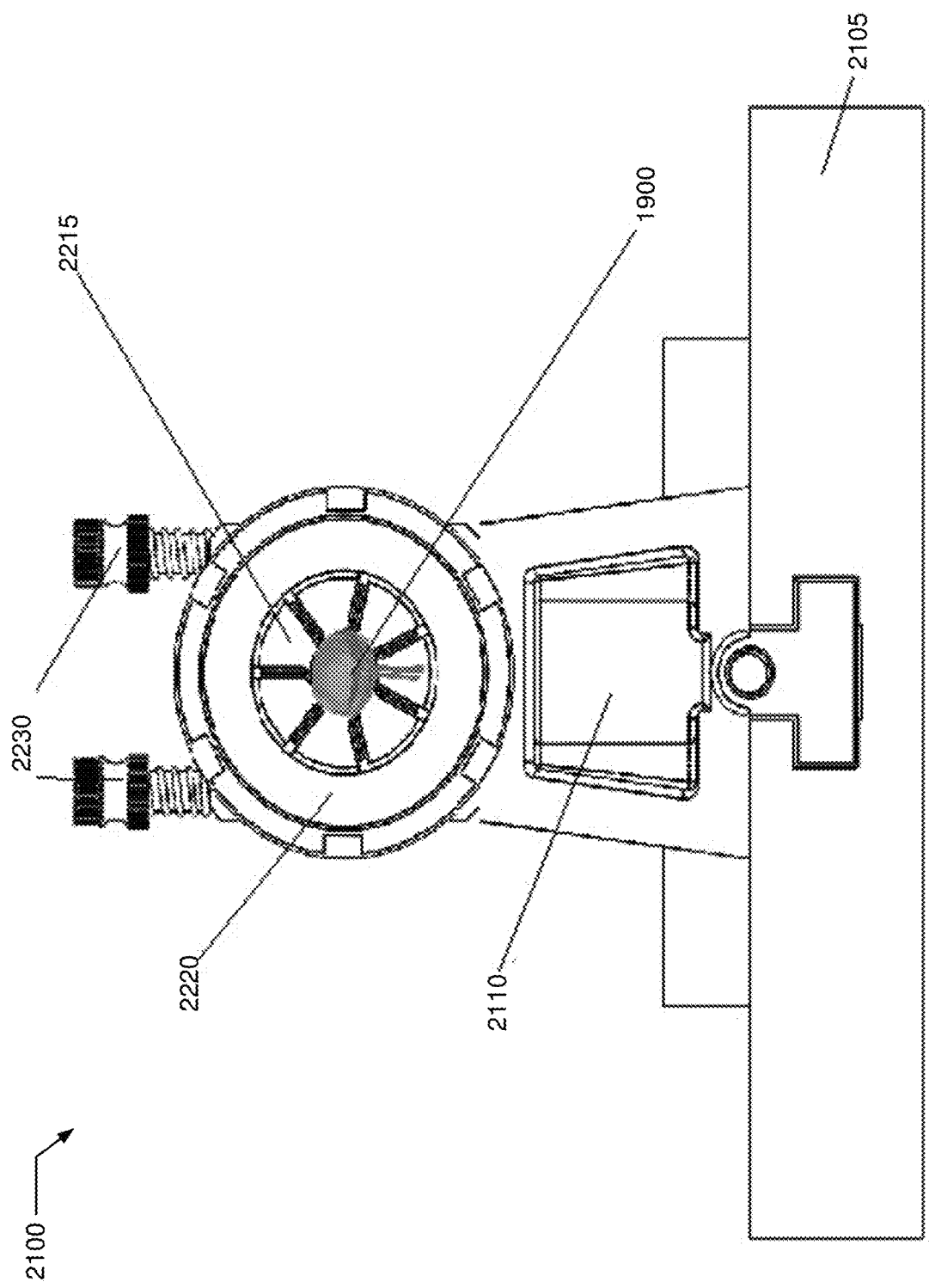
FIG. 24 illustrates an end view of FIG. 7.

FIG. 24 illustrates an end view of FIG. 23 in the context of platform 2100. In this view, chuck 2215 is in the initial or "open" state. Each collet chuck includes a number of tabs arrayed around the longitudinal tunnel, and in the open state, these tabs are separated. Forcing chuck 2215 into structure 2210 by turning nut 2220 moves these tabs closer together to narrow the longitudinal tunnel and to thereby compress graft 1900.

Figure 25:
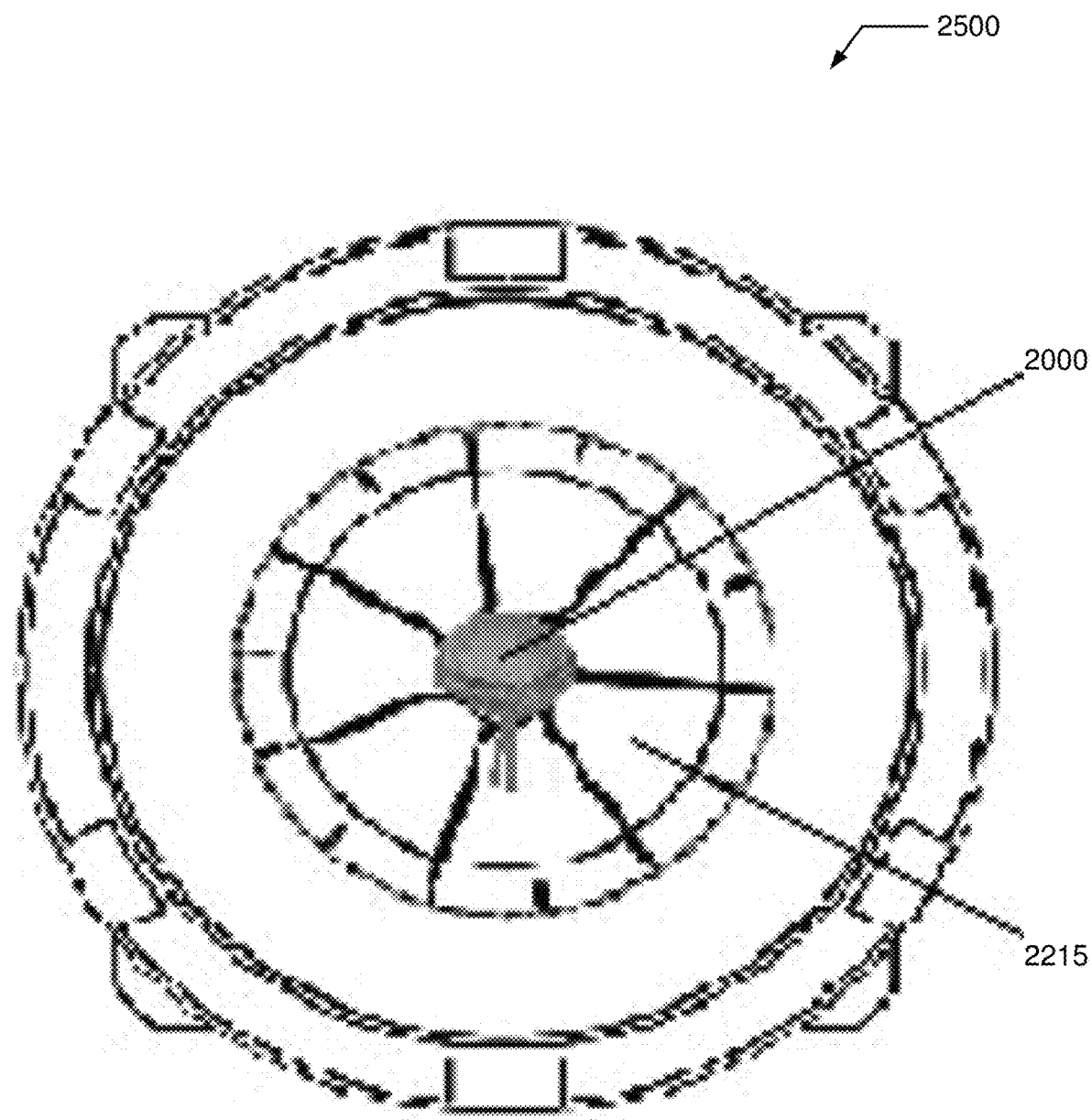
FIG. 25 illustrates an end view similar to FIG. 8 but after lateral compression to produce the compressed connective tissue graft of FIG. 20.

FIG. 25 illustrates an end view 2500 similar to FIG. 24 but after lateral compression (e.g., longitudinal tunnel of chuck 2215 closed) to produce compressed connective tissue graft 2000. In FIG. 25 the tabs of chuck 2215 are closed/touching which produces the smallest diameter longitudinal tunnel. This is in contrast to FIG. 24 where the tabs are separated and define a larger diameter longitudinal tunnel.

Figure 26:
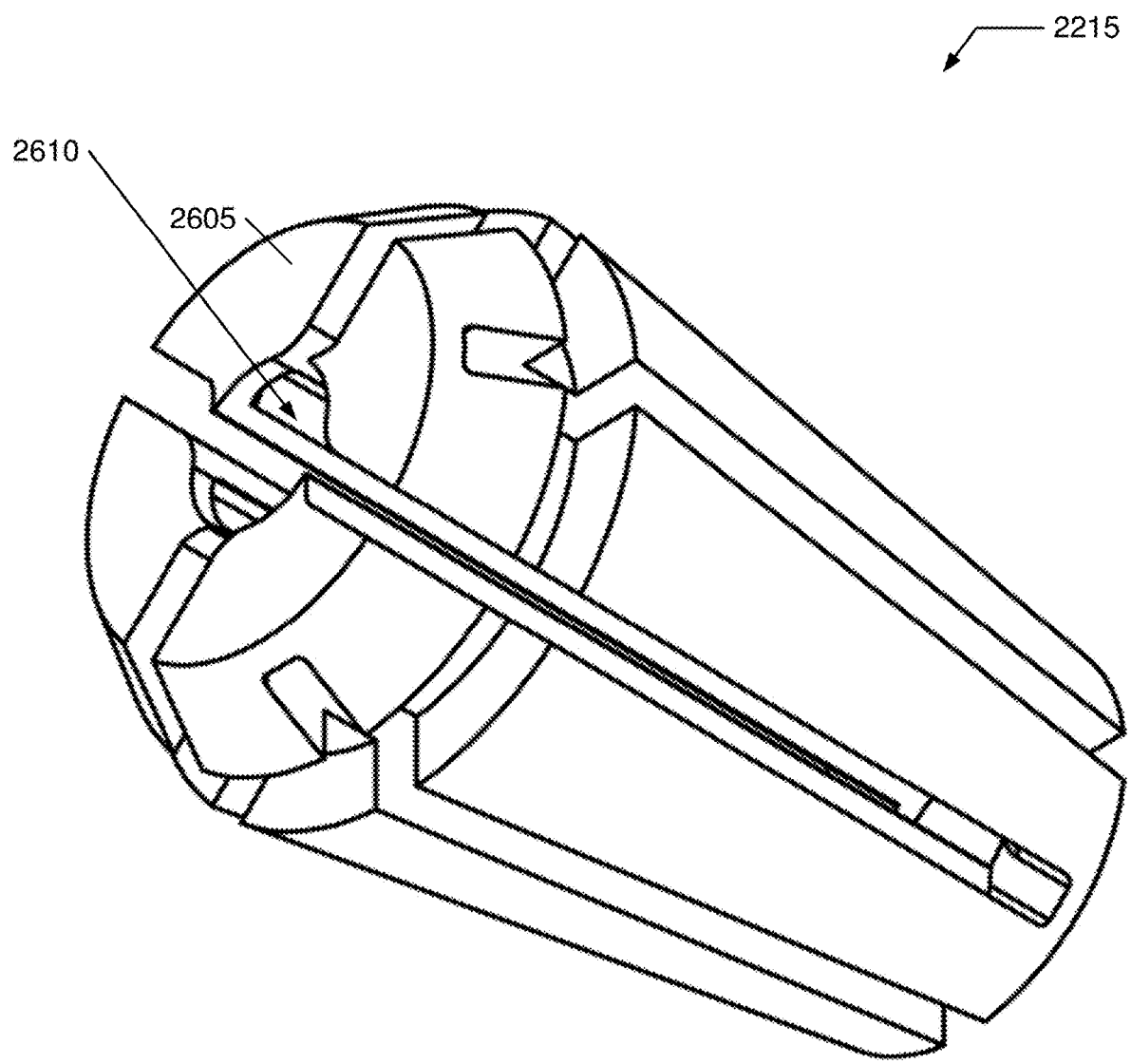
FIG. 26 illustrates a perspective view of a collet of the graft platform.
Figure 27:
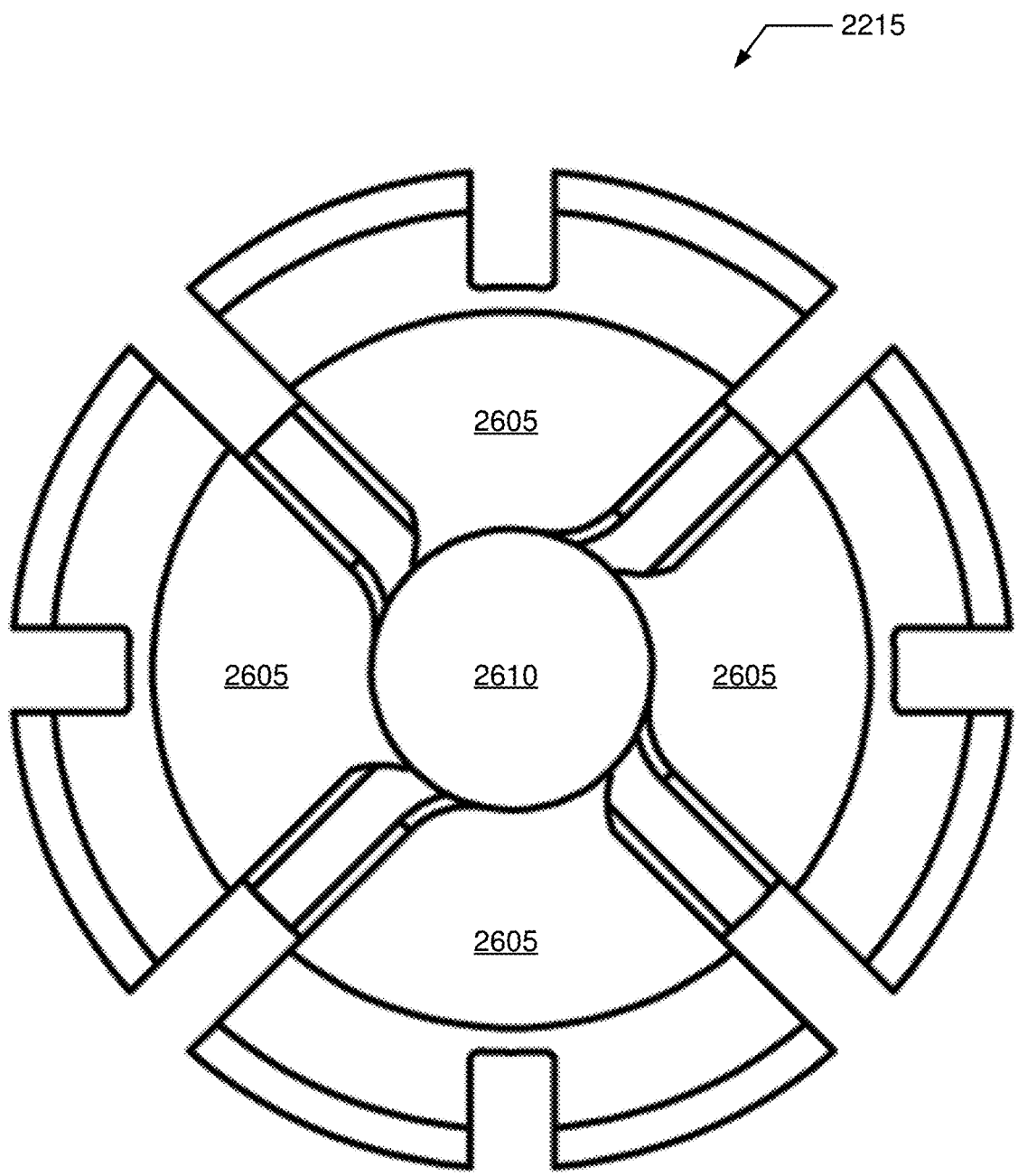
FIG. 27 illustrates an end view of the collet of FIG. 26.
Figure 28:
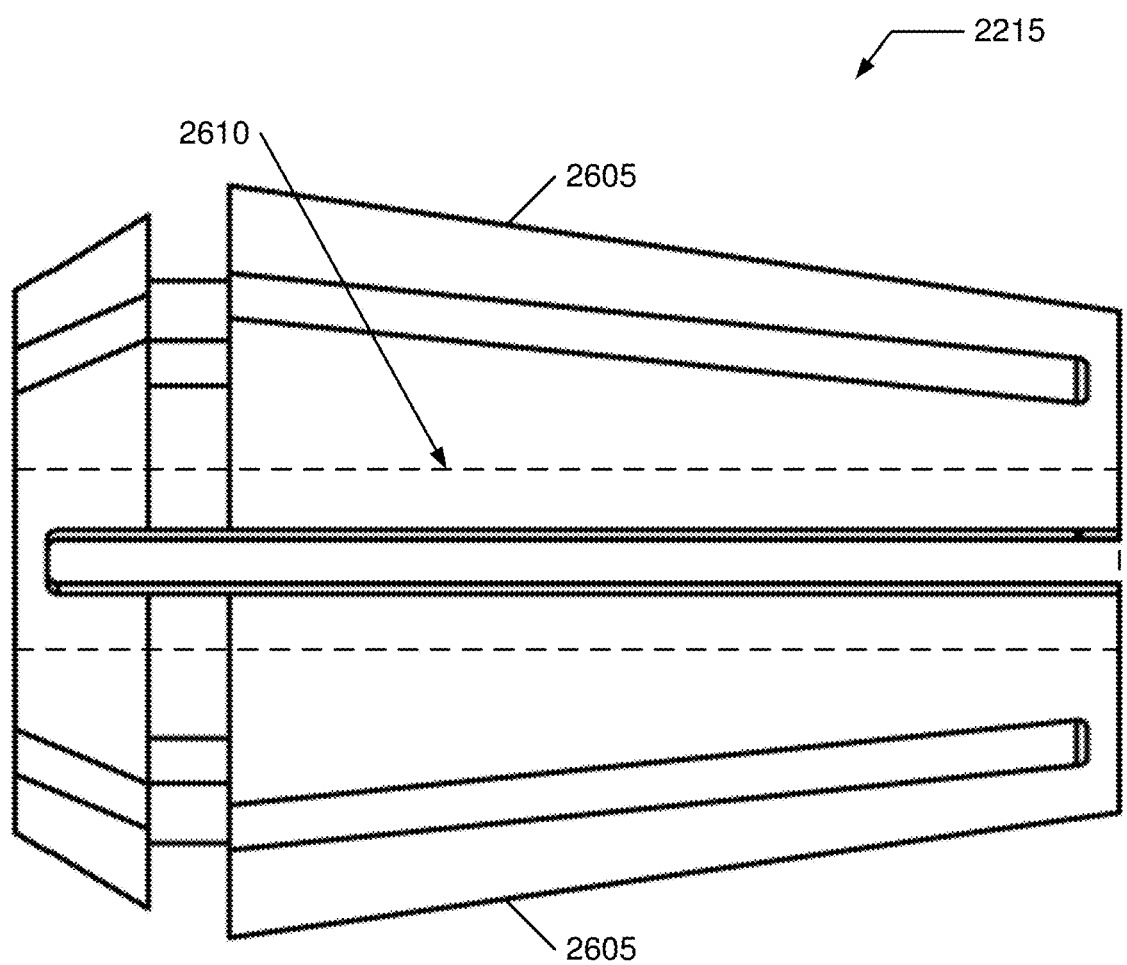
FIG. 28 illustrates a side sectional view of the collet of FIG. 26.

FIG. 26-FIG. 28 illustrate details of collet chuck 2215. FIG. 26 illustrates a perspective view of collet chuck 2215 of graft platform 2100; FIG. 27 illustrates an end view of collet chuck 2215 of FIG. 26; and FIG. 28 illustrates a side sectional view of collet chuck 2215 of FIG. 26. Collet chuck 2215 includes an N number, N≥2, of moveable tabs 2605 that collectively define a longitudinal tunnel 2610. N may be any integer two or greater and may often be an even number, for example N is an element of the set {2, 3, 4, 5, 6, 7, 8, 9, 10, 11, 12, . . . } depending upon various design considerations in compressing and shaping an outer perimeter of graft 1900 to produce graft 2000. In FIG. 26-FIG. 28, N=4. In FIG. 24 and FIG. 25, N=7.

In operation, platform 2100 may include one or more different modalities for decreasing D1 of graft 1900 and providing D2 of graft 2000 that may be significantly smaller. One modality includes inserting all or portion of graft 1900 into one or both collet chucks 2215 (chucks 2215 may have a length to accommodate the intended use. A single chuck 2215 that is long enough may compress an entire length of graft 1900. The tightening of the collet nut while some of all of graft 1900 is disposed inside the longitudinal tunnel of the corresponding collet chuck will compress D1 of graft 1900 to D2 of graft 2000.

In other embodiments, a portion of each end, up to one-half for example, of graft 1900 is installed into each of two opposing collet chucks on platform 2100. That end portion in each collet chuck may then be compressed by tightening the corresponding collet nut. In this example, one-half of graft 1900 is compressed by each stage. Variations are possible, such as where ⅓ of graft 1900 is installed into one chuck and the remainder ⅔ of graft 1900 installed into the other chuck. This allows for each end or portion of each end to be compressed to different diameters (the compressed diameter of one end may be different than the compressed diameter of the opposite end). Some procedures or protocols may be advantaged by producing differently sized or profiled tunnels in the different bones—one tunnel size or profile in a femur and a different one in the tibia for example. Some embodiments of the present invention allow for this as necessary or desired.

Another possible modality for decreasing D1 of graft 1900 is to use platform 2100 to grip ends of graft 1900 in each housing and then to use the drive rod to separate the housings. By using the torque wrench, an operator understands how much tension is applied to graft 1900 intermediate the gripped ends which tensions, stretches, and thins the intermediate portion. The degree of thinning of this intermediate portion is dependent upon the force applied and the tensile and compressive moduli (mechanical properties) of graft 1900. As long as the thinning occurs in the elastic deformation range, there will be a tendency for the intermediate portion thinned this way to return towards a thicker instance. The graft may also exhibit elastic and/or inelastic behavior frequently described in solids, where a subset of viscoelastic materials have a unique equilibrium configuration and ultimately recover fully after removal of a transient load, such that after being squeezed, they return to their original shape, given enough time. The transient strain is recoverable after the load or deformation is removed. Time scale for recovery may be short, or it may be so long as to exceed the observer's patience.

In some embodiments, it is thus possible to produce a diameter profile over a length L2 of graft 2000. Typically graft 2000 includes a single diameter D1 over the entire length L1. However, embodiments of the present invention may tailor each end or portion thereof with a desired diameter (the same or different from the other end) and with a desired diameter for the intermediate portion that is the same or different from either or both ends. Some amount of each end, and the intermediate portion, may have its diameter be relatively independently controlled. Any end or intermediate portion may have a greater or lesser diameter than another part of graft 2000. The intermediate portion may have the same, larger, or smaller diameter than one or both end portions. The same is true of each end relative to the other end and the intermediate portion.

In the above discussion, the grafts and tunnels, and structures complementary thereto have been described as generally elongate circular cross-sectional structures (e.g., cylindrical tunnels). This is because the current procedures provide for drilling tunnels in the implicated bones and the drilling produces generally circular cross-sectional tunnels. In general all ACL reconstructive techniques, whether performed arthroscopically or open, utilize the particular technique of initially proposing the tibial and femoral tunnels with a "guide wire", which is drilled in the desired position, and after confirmation, over-drilled with a cannulated drill bit to produce a perfect cylindrical tunnel.

In some instances, it may be possible to produce tunnels in the bones, possibly utilizing different techniques and completely different technologies, with the tunnels having other than circular (e.g., cylindrical) cross-sections. Perhaps healing and recovery may be better achieved with a generally elliptical cross-section tunnel such as a frustum (e.g., of a pyramid or cone or other closed three-dimensional cavity volume), a rectilinear cross-section tunnel, or a tunnel that has a varying diameter over its length. In some cases, a bone preparation tool may include a LASER, a 3-dimensional (3D) bone sculpting tool, or robotic instruments to define a desired regular/irregular/symmetric/asymmetric tunnel that varies from a same-sized cylindrical bore (iv) typically produced in the femur and the tibia for current ACL reconstructive techniques.

An advantage of some embodiments of the present invention when installing a compressed graft 2000 into any of these alternative types of tunnels (as well as the cylindrical bores from a drill) is that the graft 2000 may selectively expand to fill any variable profile of the tunnel in the femur and tibia.

Figure 29:
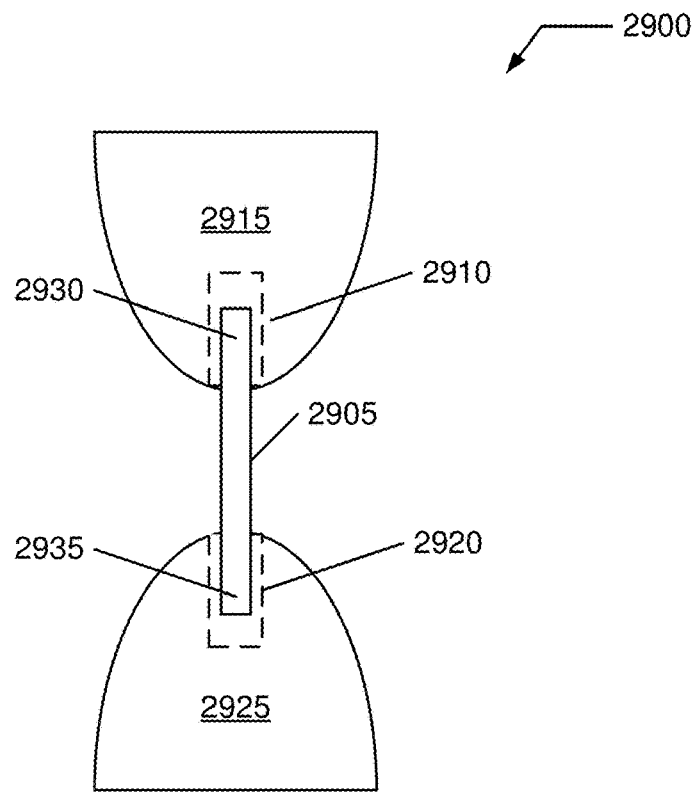
FIG. 29-FIG. 30 illustrates a reconstruction of an ACL in a pair of cylindrical bone tunnels.
Figure 30:
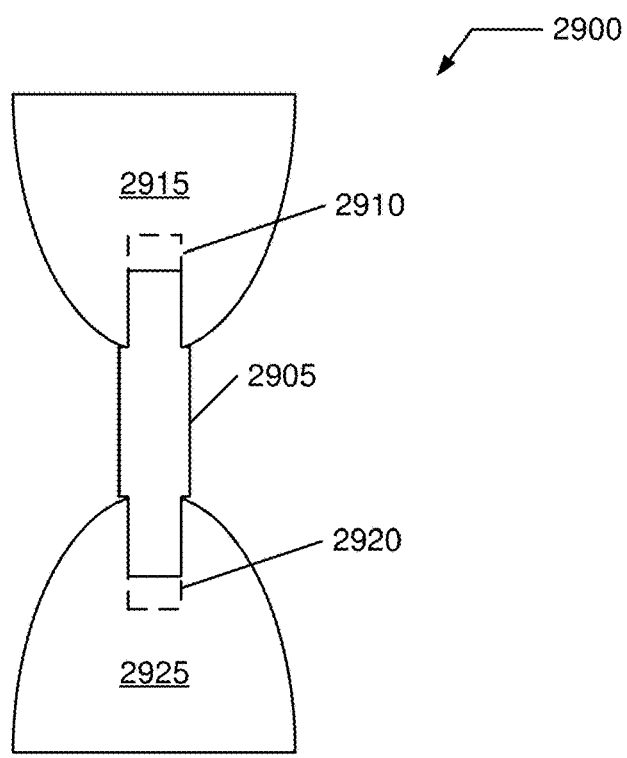

FIG. 29-FIG. 30 illustrate a reconstruction 2900 of an ACL in a pair of cylindrical bone tunnels. FIG. 29 illustrates pre-expansion of a compressed ACL graft 2905, such as an appropriately sized embodiment of graft 2000 in FIG. 20 and FIG. 30 illustrates a post-installation-expansion of compressed ACL graft 2905. A bone tunnel 2910 is prepared (e.g., profiled, sculpted, processed) in a portion of a femur 2915 and a bone tunnel 2920 is prepared in a portion of an adjacent tibia 2925. There may be several ways to prepare these bone tunnels, such as by installing a guide wire along a desired path and then using a cannulated drill bit to follow the guide wire to the desired depth. For example, these tunnels may have a diameter of about 9 millimeters and ACL graft may have an uncompressed diameter of about 10 millimeters and a compressed diameter of about 6-8 millimeters. With these dimensions, the compressed ACL graft may easily be installed into a prepared bone tunnel and an uncompressed ACL graft may produce significant lateral frictional forces holding it in place as the healing occurs and natural fixation completes itself to bond the uncompressed ACL graft into the prepared bone tunnels (with or without external fixation devices or structures).

After decompression of compressed ACL graft 2905 (in FIG. 30) the expanded ACL graft 2905 tightly fills each bone tunnel as it conforms to the cross-section profile (e.g. circle for a cylindrical bone tunnel). A diameter/profile of bone tunnel 2910 need not, but may be, the same as a diameter/profile of bone tunnel 2920. As long as portions of the diameters of the bone tunnels where the ACL graft is to be bonded (e.g., openings of the bone tunnels) are smaller than an original unexpanded diameter of the compressed ACL graft, temporary press-fit fixation from the decompression of the installed graft will secure the decompressing ACL graft into the bone tunnels and provide the advantages noted herein.

Once the bone tunnels are prepared, a first end 2930 of compressed ACL graft 2905 is installed into bone tunnel 2910 and a second end 2935 of compressed ACL graft 2905 is installed into bone tunnel 2920. As compressed graft decompresses it expands towards its original pre-compressed shape unless constrained (by a bone tunnel side wall for example).

Figure 31:
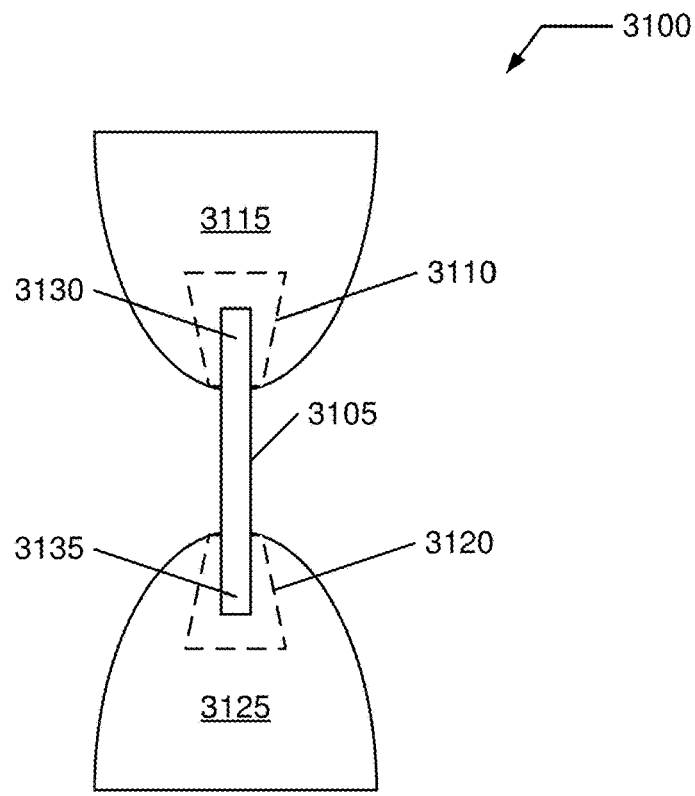
FIG. 31-FIG. 32 illustrates a reconstruction of an ACL into a pair of profiled bone tunnels.
Figure 32:
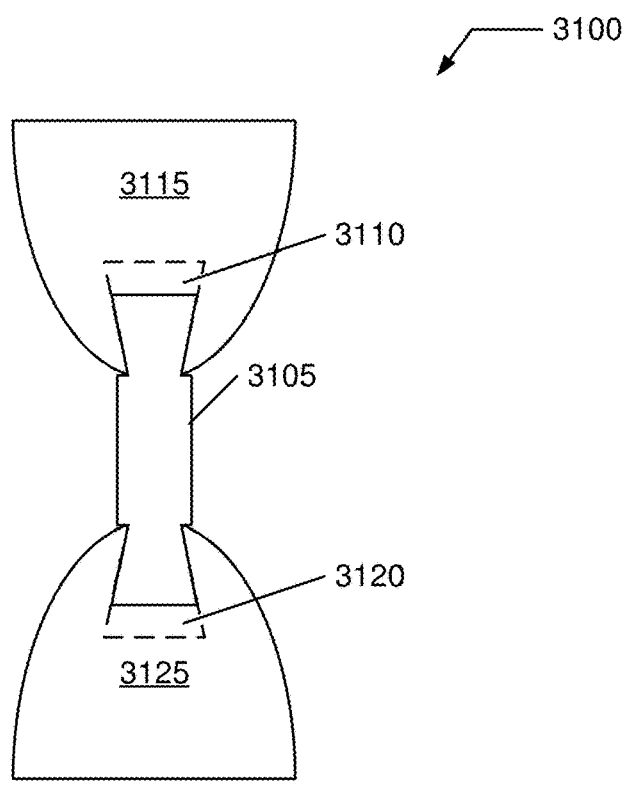

FIG. 31-FIG. 32 illustrate an alternative reconstruction 3100 of an ACL into a pair of profiled bone tunnels. FIG. 31 illustrates pre-expansion of a compressed ACL graft 3105 (which may be similar to ACL graft 2905 in FIG. 29), such as an appropriately sized embodiment of graft 2000 in FIG. 20 and FIG. 30 illustrates a post-installation-expansion of compressed ACL graft 3105.

Alternative reconstruction 3100 is similar to reconstruction 2900 with the exception of the shape of the bone tunnels (and consequently the manner of the formation of the profiled bone tunnels in FIG. 31 and FIG. 32. The noted characteristic of the conforming decompression of a compressed ACL graft 3105 is used in this alternative to expand into specially profiled bone tunnels that may have a number of shapes where an opening profile is purposefully and significantly smaller than a cavity profile deeper into the bone.

A profiled bone tunnel 3110 is prepared in a portion of a femur 2915 and a profiled bone tunnel 3120 is prepared in a portion of an adjacent tibia 2925. There may be several ways to prepare these profiled bone tunnels, such as by use of a surgical robot or three-dimensional bone sculpting, or LASER such as laser ablation of bone as described herein, for example in the discussion of FIG. 34 below. For example, these profiled tunnels may be generally shaped as a frustum have a narrower opening diameter of about 8 millimeters, a wider base diameter of about 9-10 millimeters, and the ACL graft may have an uncompressed diameter of about 10 millimeters and a compressed diameter of about 6-7 millimeters. With these dimensions, the compressed ACL graft may easily be installed into a prepared bone tunnel and a decompressing ACL graft, when decompressed, may produce significant frictional and mechanical forces (e.g., normal forces) holding it in place as the healing occurs and natural fixation completes itself to bond the uncompressed ACL graft into the prepared bone tunnels (with or without external fixation devices or structures).

After decompression of compressed ACL graft 3105 (in FIG. 31) the expanded ACL graft 3105 tightly fills each profiled bone tunnel as it conforms to the cross-section profile (e.g. circle for a cylindrical frustum bone tunnel). A shape of profiled bone tunnel 3110 need not, but may be, the same shape as the shape of profiled bone tunnel 3120. As long as portions of the diameters of the profiled bone tunnels where the ACL graft is to be bonded (e.g., openings of the bone tunnels) are smaller than an original unexpanded diameter of the compressed ACL graft, temporary "biologic press-fit" and mechanical fixation from the decompressing ACL graft will secure the ACL graft into the profiled bone tunnels and provide the advantages noted herein along with improved resistance to pull-out.

Once the bone tunnels are profiled, a first end 3130 of compressed ACL graft 3105 is installed into bone tunnel 3110 and a second end 3135 of compressed ACL graft 3105 is installed into bone tunnel 3120. As compressed graft decompresses it expands towards its original pre-compressed shape unless constrained (by a bone tunnel profiled side wall for example).

Figure 33:
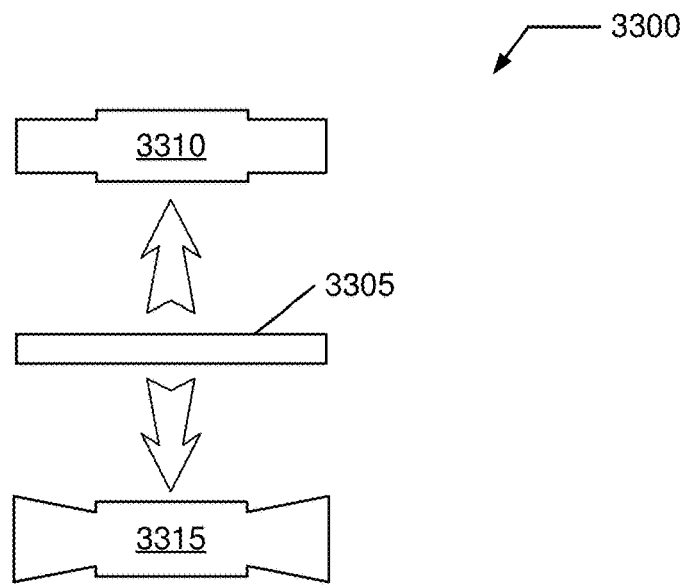
FIG. 33 illustrates different conforming expansions of a compressed ACL graft, dependent upon a preparation of a bone tunnel.

FIG. 33 illustrates different conforming expansions 3300 of a compressed ACL graft 3305, dependent upon a preparation of a bone tunnel and represent the examples from FIG. 29-FIG. 32. For example, when compressed ACL graft 3305 is installed into cylindrical bone tunnels (a simple example of a profiled bone tunnel), its decompression results in an uncompressed graft similar to graft 3310. When compressed ACL graft 3305 is installed into "inverted frustum" profiled bone tunnels (e.g., as illustrated in FIG. 31 and FIG. 32), its decompression results in an uncompressed graft similar to graft 3315.

Figure 34:
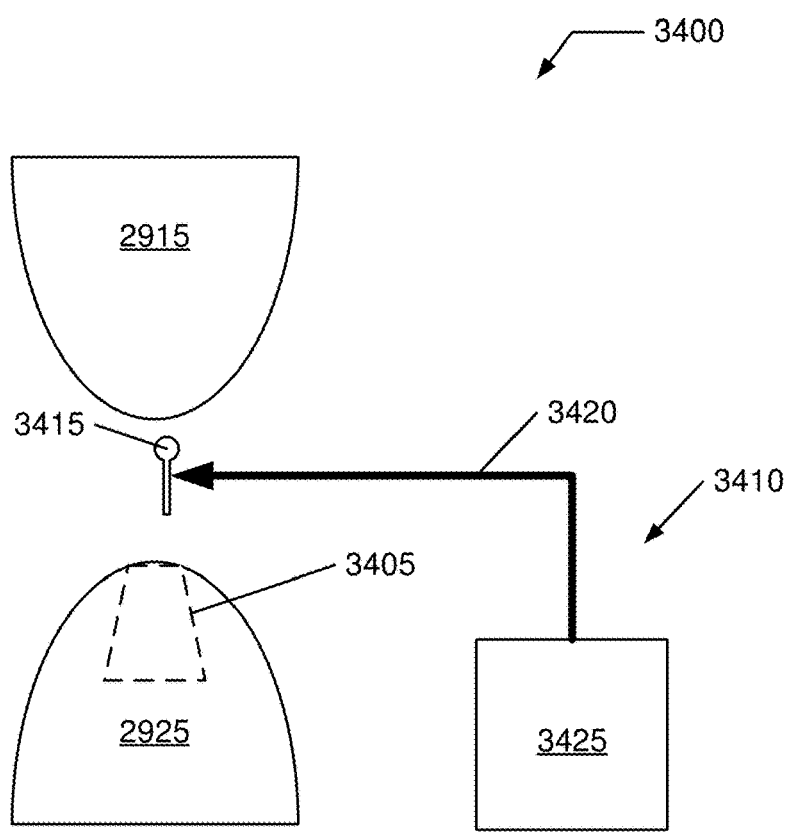
FIG. 34 illustrates a preparation of a profiled bone tunnel by an automated surgical apparatus.

FIG. 34 illustrates a bone profiling apparatus 3400 for a preparation of a profiled bone tunnel 3405 by an automated or semi-automated (constrained surgeon manipulation) surgical apparatus 3410. In FIG. 34, apparatus 3410 has produced a first profiled bone tunnel 3405 in tibia 2925 and is preparing to produce a second profiled bone tunnel in femur 2915. Apparatus 3410 includes a bone preparation implement 3415 having a mechanical coupling 3420 (direct or indirect) between a controller 3425 (e.g., a stored program computing system including processor executing instructions from a memory including a user interface to set user options and parameters).

There are automated assistive surgical devices which may fill the role of apparatus 3410, such as robotic assisted surgical platforms (e.g., MAKO, da Vinci, Verb, Medtronic, TransEnterix, Titan Medical systems, NAVIO blue belt, and the like). These platforms provide positional control/limitation of surgical implements operated by a surgeon, such that the robotic tools (some of which utilize custom software and CT data) resist the movements by the surgeon that may attempt to deviate from a planned procedure, bone preparation, or other processing. These platforms are often installed into a known reference frame shared by the patient so precise position control/limitation may be imposed. Installing bone preparation tool 3415 (e.g., a high-speed rotating burr or the like) the surgeon may operate the platform to form a precisely profiled bone tunnel as described herein (e.g., first profiled tunnel 3405). A profiled tunnel may be initiated from a bit-prepared cylindrical tunnel and then profiled from there or apparatus 3410 may prepare the entirety of the profiled bone tunnel.

Further, current ACL techniques require that the surgeon estimate the length of the graft to fit the combined length of the tibial and femoral tunnels plus the intra-articular length of the ACL graft, housed in the notch. Despite best efforts mismatches between the length of the graft and the tunnels is not infrequent, which adversely affects the outcome. The use of automated surgical devices noted above has the advantage of providing the exact lengths of the tibial and femoral tunnels as well as the intra-articular length of the ACL graft within the notch. These techniques allow bone resection of any profile with varying trajectories and depths based on planned procedure, for example to within a millimeter. The tunnel lengths can be determined pre-operatively or intra-operatively and correlated with the length and diameter of the prepared allograft. Growth factors can be applied to pre-prepared allograft with external of and/or internal sheaths, or to auto-grafts prepared at the time of surgery.

Apparatus 3410 may be used to produce internal ridges, dimples, or other irregularities in the lateral wall of a bone tunnel (profiled or "conventional" cylindrical tunnel). The uncompressing ACL graft will fill these irregularities which may further promote fixation and healing.

Described above are embodiments (apparatus and methods) for production of a compressed connective tissue graft. Such a graft may be prepared from patient or may be provided separately (e.g., a frozen pre-prepared allograft) that may be sized and compressed.

An embodiment of the present invention includes off-site advance preparation of compressed connective tissue graft that are shipped and stored in the compressed state. They may be frozen in the compressed state sufficiently partially thawed at the time of installation to allow appropriate decompression in situ. It may be that the pre-compressed allograft is delivered in a peel pack while freeze dried in the compressed state. The allograft is removed from the packaging and the surgeon will have some time for installation before it decompresses. In some cases, the allograft's decompression is accelerated by saline solution. Exposure of the compressed allograft to body fluids in the bone tunnels may also accelerate the decompression for fixation into the bone tunnel.

In other embodiments, a protective sheath may be provided that is installed after compression to maintain the connective tissue graft in the compressed state. Removal of the sheath allows for decompression. The sheath may be dissolvable in body fluids and installation into a bone tunnel begins the dissolution and decompression.

The sheath may be provided as a two-part element: an outer protective film prevents decompression and an inner layer that may temporarily inhibit decompression during the installation process. When ready to install, the outer layer is removed and the connective tissue graft (with inner layer) is inserted into the bone tunnel. Alternatively, the outer and inner sheaths of compressed ACL prepared grafts can be embedded with a combination of biological growth factors including the TGF family, bone morphogenic proteins (BMP), insulin like growth factors, matrix metalloproteinases, fibroblast growth factors, vascular endothelial growth factors, platelet derived growth factors, and or other stem cell derived growth factors (including epithelial and mesenchymal stromal cells), which alone or in combination can significantly improve healing of tendon to bone, promoting angiogenesis and osteogenesis at the tendon-bone interface after ACL reconstruction. The sheaths may also include other allogenic sources of growth factors such as amniotic membrane products and the like.

Figure 35:
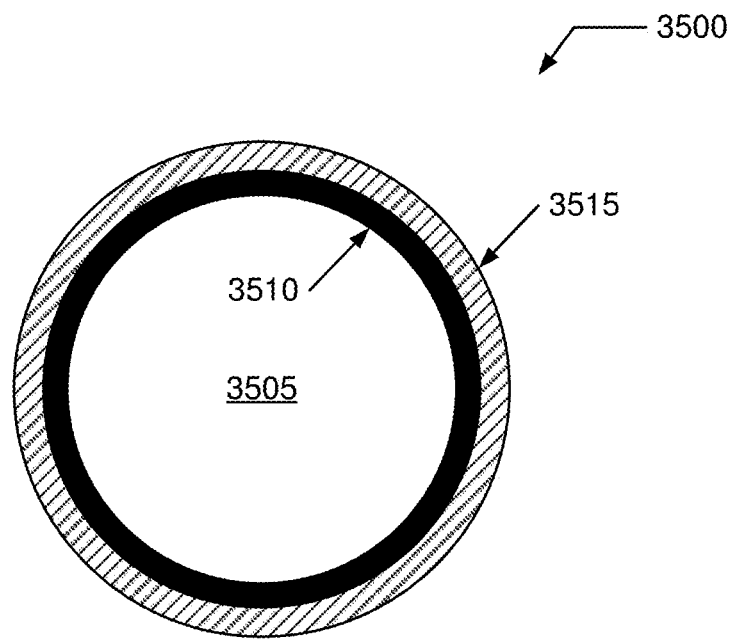
FIG. 35 illustrates an allograft system including a pre-compressed allograft with a sheathing subsystem having an outer sheath and an inner sheath.

FIG. 35 illustrates an allograft system 3500 including a pre-compressed allograft 3505 with a sheathing subsystem having one or more sheaths (e.g., an inner sheath 3510 and an outer sheath 3515). The sheathing subsystem may accomplish one or more functions depending upon implementation, to achieve desired goals as described herein. Those goals may include a number of functions, such as maintaining a pre-compressed allograft 3505 in its compressed mode until installed into a prepared bone tunnel for decompression as described herein. Other functions include enhancing preservation of sterility and delivery of growth factors into the bone tunnel at the graft/tunnel interface.

Figure 36:
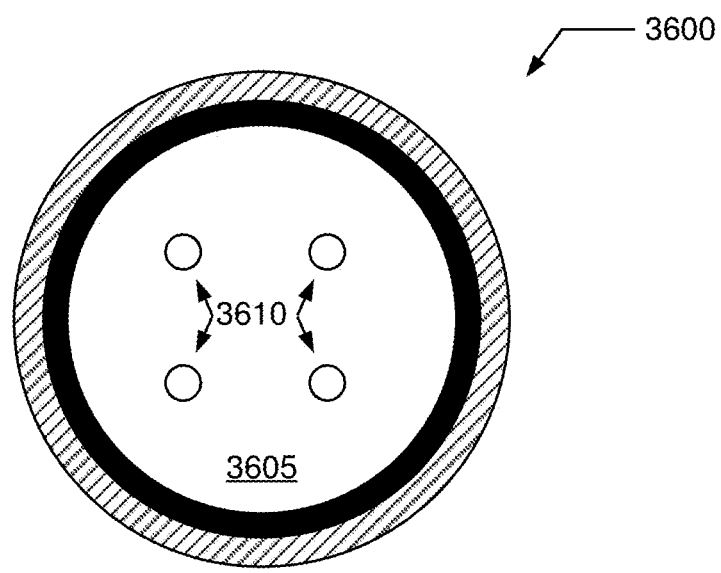
FIG. 36 illustrates an allograft system including a pre-compressed allograft with a prosthesis subsystem having at least one connective tissue prosthetic element.

FIG. 36 illustrates an allograft system 3600 including a pre-compressed allograft 3605 with an embedded prosthesis subsystem having at least one connective tissue prosthetic element 3610 that runs a length. There is a history of development and investigation of synthetic ACL grafts but have generally not proven to be successful. There are a number of problems of a pure synthetic connective tissue graft, including a) breakdown of the synthetic material with exposure in the joint that too often leads to synovitis and arthritis due to existence of the foreign material in joints; and b) not finding a synthetic graft that has equivalent material properties of connective tissue. There is not complete agreement on the mechanical properties needed or desired for such a synthetic graft: some materials discuss a "stiffness" of the synthetic material. However, it may be the case that a graft that has the similar "toughness properties" of native ACL may be preferable: i.e., more ductile than brittle (i.e. a larger plastic range).

Allograft system 3600 is believed to address some of these drawbacks as it is a hybrid system: native connective tissue on the outside with an embedded prosthetic element(s) inside. Illustrated is embedding the prosthetic elements inside a pre-compressed allograft as described herein. Some embodiments may embed these synthetic elements within a conventional allograft and use an alternative fixation method.

The one or more prosthetic elements may each include single strands of suitable material (e.g., natural and/or synthetic material) or may include a weave of such materials (including composite weaves of multiple different materials). The one or more embedded prosthetic elements do not provide for intra-articular bone exposure.

When embedded into a pre-compressed, the expansion fixation of the decompressing allograft into a bone tunnel secures the prosthetic elements along with the outer native decompressed graft.

Figure 37:
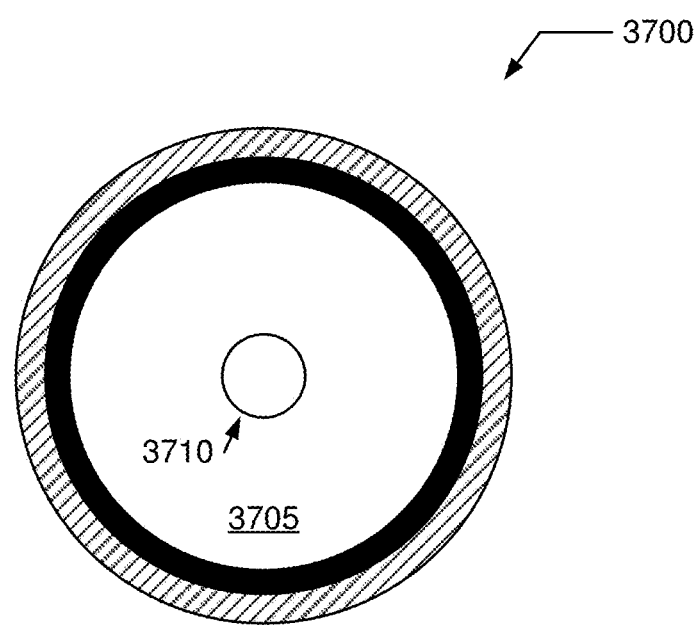
FIG. 37 illustrates an allograft system including a pre-compressed allograft with an expansion subsystem having at least one expansion element.

FIG. 37 illustrates an allograft system 3700 including a pre-compressed allograft 3705 with a expansion subsystem having at least one expansion element 3710 disposed in one or more portions that are to be expanded. These portions may be one or both end portions and/or middle portion. In some cases, the at least one expansion element may run a length of the compressed allograft. In many embodiments, the enlargement of a pre-compressed allograft has been described as a generally passive process in which a compressed allograft is allowed to decompress. It is the case that under some circumstances that natural connective tissue may expand somewhat when subjected to bodily fluids or pre-operative fluid baths (e.g., saline solution) for thawing an often-frozen allograft.

Allograft system 3700 includes an active expansion system which expands compressed native connective tissue. Expansion may be accomplished by use of the at least one embedded expansion element 3710. This at least one expansion element 3710 may be embedded into a pre-compressed allograft as described herein or embedded into a conventional allograft. In some implementations, the at least one expansion element 3710 may be part of, included within, integrated with, or provided as part of at least synthetic prosthetic element as illustrated in FIG. 37. For example, a structure may have a dual-use of providing the synthetic prosthetic element and the expansion element.

System 3700 introduces the concept of "internal expandable structures (e.g., tubes) for screw-less interference fixation of pre-compressed ACL grafts (it being noted that herein that these expandable structures may be used with conventional allografts and/or with conventional fixation methods).

One method to increase tendon/bone interface pressures (in lieu of interference screws) is a new concept of introducing expandable tubes, cages or stents within the ends of the allografts, and allowing the tube, cage or stent to expand passively or actively, to subsequently increase graft bone interface pressures to assure "direct" type fixation.

The material for the "intra graft tubes" can be synthetic non-absorbable material such as plastic and or polyester or similar material; or absorbable material.

Absorbable material could be polymer based as in polylactide (PLLA), polyglycolic acid (PGA), copolymers (PGA/PLA) poly paradiaxanone, and various stereoisomers of lactic acid, along with various bio-composite materials including a mix of polymers noted above plus calcium phosphate etc. Alternatively absorbable material could be magnesium alloy based with similar functionality where the material absorbs over time (e.g., over three months).

The expansion of the tubes may occur passively over defined period of time or actively. Active expansion can be done by balloon expansion after implantation of the graft, similar to what is done with balloon expandable stents in vascular procedures, where inflation of a balloon within the tube expands the tube inside the graft to increase intra graft pressure on the graft/bone interface, without any contact of the tube (whether bio absorbable or synthetic) with the tendon/bone interface. This concept theoretically eliminates the current problem of screw breakdown and release of inflammatory cytokines associated with tunnel widening and poor graft healing. Active expansion can also occur by "unsheathing the tube" or "pulling a rip cord" immediately after implantation of the graft, which is also done in vascular procedures.

FIG. 38-FIG. 46 illustrate aspects of biologic installation structures including a set of sensors. Cement-less arthroplasty has been recognized as one of the most successful operations of the 20th century providing pain relief for millions of patients suffering from osteoarthritis. However, cement-less arthroplasty is still plagued with failures related to aseptic loosening, infections, and metallosis. There has been increasing concerns regarding these failure modes as more surgeons with less experience perform an increasing proportion of these operations, leading to failure rates of as high as 25% (for example in hip replacement surgery) over the last 10 years.

Aseptic loosening in total joint arthroplasty is directly related to a lack of ability to precisely calibrate (interference fit) at the prosthesis/bone interface. It is generally known that micromotion of greater than 50 μm will lead to poor osteointegration (bone ingrowth), leading to fibrous tissue formation at the interface and eventual aseptic loosening, which accounts for 75% of total joint failures (including total hip and knee replacements). A prosthesis that is too loose-fitting may lead to fibrous tissue formation, while one that is too tight-fitting may lead to occult fracture, both scenarios subsequently lead to poor interference fit fixation and aseptic loosening. These problems have resulted in significant pain and suffering for patients, as well as producing tens of billions of dollars of additional cost to society.

Infections of artificial joints cause severe damage to patients bone and joints and are difficult to diagnose and treat. In particular, a diagnosis of an infected prosthesis installation involves a use of multiple laboratory tests including blood analysis, X-rays, MRIs, CAT scans, nuclear medicine scans, and a variety of chemical analysis performed on joint fluids. These tests individually and collectively yield poor results and are neither highly specific nor sensitive. The surgeon is frequently called upon to make a "clinical judgement" in assessment of prosthetic joint installation infections and ultimately is faced with incorporating the varied and frequently conflicting data provided through these tests.

Metallosis is recently a recognized clinical syndrome that has caused significant concern for the orthopedic community. Morse taper technology has been utilized in orthopedics to bond modular prosthesis to each other (described in US patent applications (Ser. No. 15/362,675 filed 28 Nov. 2016), (Ser. No. 15/396,785 2 Jan. 2017), and (Ser. No. 14/965,851 10 Dec. 2015)). Micromotion at the modular prosthesis interface has led to production of metal debris, which through the process of Mechanically Assisted Crevice Corrosion (MACC) led to the clinical syndrome of Trunnionosis and Metallosis causing Adverse local Tissue Reactions ALTR with significant damage to bone, joints and soft tissues, as well as metal toxicity.

Current diagnostic methods for evaluation of aseptic loosening, infection and metallosis in orthopedics (especially cement-less arthroplasty) are highly inaccurate, lacking both specificity and sensitivity, often leaving the surgeons to rely on "clinical judgement" without the benefit of clear and convincing evidence.

Ligament reconstruction techniques in orthopedics similarly involve application (placement) of ligaments grafts as prosthetic devices in prepared bone tunnels. These (soft tissue prosthetic) replacements share the some of the same concerns as metal alloy prosthetic replacements including infection and loosening (graft rejection), as well as graft failures with subsequent traumatic injuries.

Dental procedures similarly involve application of prosthesis or implants into bone and can be plagued by similar problems (as in orthopedic surgery) such as aseptic loosening, infection, and metallosis. For example, an early infection of a dental implant may not be easily detectable through standard testing with X-rays and laboratory tests. When laboratory tests are negative, but the patient is symptomatic, dentists typically treat patients empirically with oral antibiotics. However, deep infections do not respond well to oral antibiotic treatment, which can lead to progression of the disease and development of antibiotic resistance. Biosensors, as described for orthopedic Prosthetic Interface Point of Care Testing PI-POCT described in the subsequent sections, have similar uses and utility in dental surgery, particularly in diagnosis of infections and implant loosening.

What is needed is in the field of orthopedic surgery, in particular in cement-less arthroplasty and ligament reconstruction techniques (essentially all aspects of orthopedic surgery where a prosthesis is introduced into the body), as well as dental surgery, is a development of prosthesis interface point-of-care (POC) testing devices which can provide diagnostic tests and 'sensing' in situ, directly, and at the actual site of possible pathological process, to facilitate evidence-based diagnosis. We term this phenomena Prosthetic Interface Point of Care Testing PI-POCT.

Current diagnostic methods for evaluation of failures of orthopedic arthroplasty and soft tissue prosthetic replacements are varied and expensive and collectively produce low yield. There is a need for methods to produce POC tests in orthopedic arthroplasty (and ligament reconstruction) that are affordable, user friendly, specific, sensitive, robust and equipment free.

Recent advances in biosensors, semiconductors and wireless communication techniques have attracted significant interest in multiple industries. Wireless POC devices as described herein offer an advantage of continuous monitoring of biologically and physically relevant parameters, metabolites and bio-molecules relevant to pathologic conditions such as aseptic loosening, infections, metallosis, and graft failures.

Biosensors are ubiquitous in biomedical diagnosis as well as other POC monitoring of disease, drug discovery, forensics, and biomedical research. A wide range of methods have been used for development of biosensors.

A biosensor includes two components: a bioreceptor and a transducer. In its most basic form the bioreceptor is a biomolecule that recognizes a target analyte, and a transducer converts the recognition event into a measurable signal. A uniqueness of the biosensor includes that these two components are integrated into a single sensor (unit), which measures the target analyte without use of a reagent. A simplicity and a speed of measurement requiring no specialized laboratory skills are some advantages of a biosensor.

Figure 38:
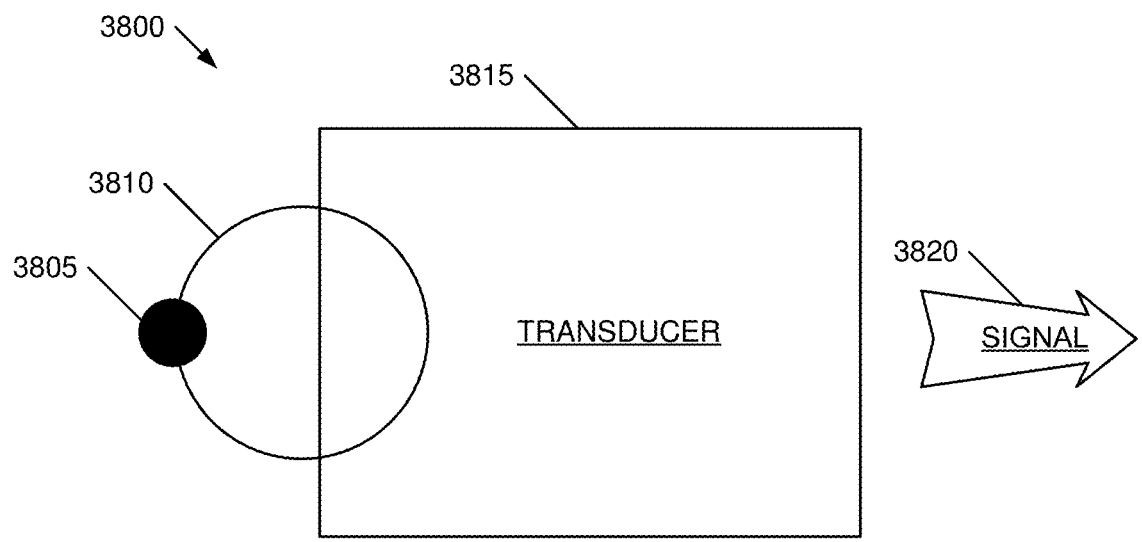
FIG. 38-FIG. 46 illustrate aspects of biologic installation structures including a set of sensors.

FIG. 38 illustrates a generalized biosensor 3800. An analyte 3805 is recognized by a bioceptor 3810 through a recognition event. The recognition event is transformed by a transducer 3815 into a signal 3820 that may be measured/quantified.

Biosensor research has experienced explosive growth over the last two decades. A modern biosensor is an analytical device that converts a biological response into a quantifiable processable signal. Biosensors are employed in disease monitoring, drug discovery, detection of pollutants and disease-causing microorganisms.

Recent advances in integrated biosensors and wireless communication have created a new breed of POC diagnostic devices which may include one or more of the following components: (a) an analyte—a substance of interest that needs detection; (b) a bioreceptor—a molecule/material/compound that specifically recognizes the analyte is known as a bioreceptor with enzymes, antibodies, DNA, RNA, aptamers, cells, receptor proteins included as examples of bioreceptors wherein an interaction of the bioreceptor with the analyte is termed bio-recognition; (c) a transducer—the transducer converts one form of energy into another, which when incorporated into a biosensor means the transducer converts the bio recognition signal into a measurable signal, which may include either an electrical signal (e–) or and optical signal; (d) a set of electronics—for example integrated circuits and wireless systems wherein the transduced signal may be processed and amplified for display; and (e) a user interface—for example an indicator or display mechanism which may involve hardware and software that interprets the results of a biosensor in a user-friendly/perceptible manner.

Figure 39:
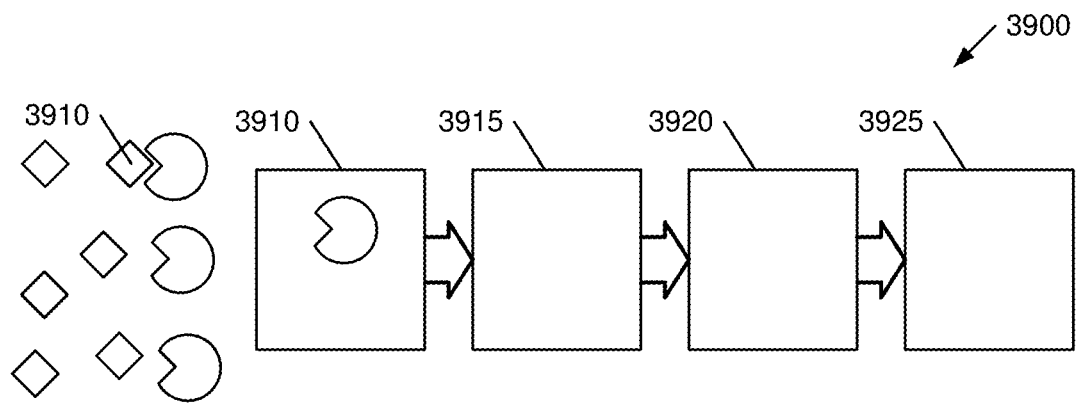

FIG. 39 illustrates a point-of-care (POC) diagnostic device 3900. Device 3900 is responsive to an analyte 3905 using a bioreceptor 3910. Bioceptor 3910, in the presence of analyte 3905, produces a bio-recognition event that is converted by a transducer 3915 into a signal, sometimes referred to as signalization. The signalization is processed by a set of electronics 3920 and may be presented to a user by some type of a display 3925 or indicator or may be otherwise analyzed or incorporated into post-conversion activities of a system or process that makes incorporates device 3900.

Bioreceptor 3910 may include an enzyme, cell, aptamer, DNA, nanoparticle, and antibodies producing the bio-recognition event which may include production of light, heat, pH change, mass change, and combinations. These bio-recognition events are processed by transducer 3915 which may include a photodiode, pH electrode, quartz electrode, field-effect-transistor (FET), and the like and combinations thereof.

Transducer 3915 produces a transducer signal that is received by electronics 3920 which may convert from analog-to-digital and/or include signal conditioning structures, systems, and processes. Electronics 3920 produces a processed signal for display 3925.

In such manner biological molecules are "immobilized" (attached) on sensing electrodes for detection of a target analyte. The target analyte interacts with immobilized bioreceptors on the surface of sensing electrodes which further induces a change in an electrical signal such as conductance, current, potential, frequency, phase, amplitude, impedance or capacitance. The signal response is monitored and correlated to the concentration to the target analyte through a calibration curve.

Wireless biological electronic sensors have been created by integrating a bio-receptor sensing transducer with wireless antennas. The wireless aspect of (biological electronic systems) are classified into following categories: wireless radio frequency identification, wireless acoustic waved based biosensors, wireless magneto elastic biosensors, wireless self-powered biosensors and wireless potentiostat-based biosensors.

To develop wireless biological electronic sensors, a sensing transducer is immobilized (attached) to bioreceptor to make a biosensing transducer. This biosensing transducer is further integrated with a wireless communication element to transmit sensing signals to external receiving device.

Several types of sensing transducers have been used and include electrochemical electrodes, transistors, resistors, capacitors, surface acoustic wave electrodes, magnetic acoustic plates, magnetoelastic ribbons.

The bioreceptors mainly include catabolic based bioreceptors such as enzymes or binding/hybridization based bioreceptors such as antibodies, DNA, RNA, aptamers, peptides, or phages.

Among different type of sensing transducers, electrochemical electrodes are a basic and widely used class of transducers, majority of which are amperometry based ($H_2O_2$ or $O_2$ measurement), potentiometry based (pH or plon measurement), or photometry based utilizing optical measurements. All of which may act to convert action of the bioreceptor molecule (a biorecognition event) into a signal.

Over time different methods of transduction have been developed and will be developed, some of which may be bio-compatible for use with a biologic structure for compatible installation in a living body. In principle any method that is affected by the biorecognition reaction can be used to generate a transduced signal and may, in some cases, be included in an embodiment of the present invention.

Piezoelectric materials and surface acoustic wave devices offer a surface that is sensitive to changes in mass. For example, piezoelectric silicon crystals called quartz crystal microbalance QCM may be used to measure very small changes in mass in the order of picograms.

Conductimetric transducers may be used when a biorecognition reaction causes a change in the dielectric measurement of the medium.

Thermometric transducers may be used when the biorecognition event is accompanied with the creation or absorption of heat.

For some implementations of the present invention, there may be advantages associated with miniaturization. Mass production has led to the development of field-effect-transistor (FET) technology for application as a transducer which may be incorporated into some biosensors as described herein. Field-effect transistors (FETs) are used extensively in semiconductor industry in memory and logic chips and respond to changes in an electric field. The construction of multi-analyte conductance biosensors and conductive polymer-based devices have been, and will be, enhanced by a rapid development of semiconductor technology and sensor integration with microelectronics devices producing FET devices.

In recent years an emerging field of nanotechnology has produced interesting materials (such as nanowires, nanotubes, nanoparticles, nanorods, thin films, graphene and graphene oxide, carbon nanotubes), all of which are increasingly being used as building blocks of biosensing techniques and new transduction technologies, advancing biosensor development.

The nanostructures sometimes are associated with extraordinary electronic properties, enhanced electron transport ability, mechanical strength, pliability and impermeability, and have found their place in several biosensors such as biological field effect transistors Bio-FET which couple a transistor device with a bio-sensitive layer that can specifically detect bio-molecules by detecting changes in electrostatic potential due to binding of analyte. Commonly used Bio-FET systems in medical diagnostics include: (ion-selective field-effect transistor ISFET and enzyme field-effect transistor EnFET).

Specifically, reducing a size of a biosensor to nanoscale may result in a better signal to noise ratio, as well as requiring smaller sample volumes for detection. In particular, in the nanoscale dimension, a surface to volume ratio of the sensing active area increases and the size of the detecting electrode and the target analyte become comparable. This may result in both better sensitivity and specificity providing the promise of single molecule detection. Nanomaterials provide new and enhanced methods of biosensing by improving sensitivity, increasing stability and shelf life, achieving better signal to noise ratio, better response time and so on, and while at the same time reducing fabrication costs, and allowing development small compact biosensing devices.

Another use of nanotechnology involves creation of nanopores and nanochannels with encapsulation techniques (lipid, hydrogel, Sol-Gel, lipid bilayers) to produce "ion channels" and to make use of a concept of transport process across appropriate membranes to create highly sensitive transduction elements.

Traditional electrochemical measuring methods (with electrodes) have largely contributed to the current advanced understanding of transduction mechanisms. Over time the integration of sensors with field-effect transistor technology (FET) and nanotechnology have produced devices that can be highly specific, sensitive and compact with low cost of fabrication. The fusion of electrochemical biosensing, nanotechnology, and field effect transistor FET technology makes this technology adaptable for point of care (POC) diagnostics in orthopedic surgery and post-operative care and monitoring.

In addition to an integration of electrochemistry with microelectronics and nanotechnology, novel and complementary biosensing techniques have emerged that provide specific additional strengths in biosensing, providing the ability to detect changes in mass and optical evanescence. For example, Electrochemical Surface-Plasmon Resonance EC-SPR and Optical Waveguide Light Mode Spectroscopy (OWLS) can be combined with electrochemical transducers to provide direct observation of changes in optics and mass absorption, in addition to electrical change. Electrochemical Quartz Crystal Microbalance (EC-QCM) uses the inherent resonance of crystals and its decrease with mass absorption to detect biological reactions.

The varied and extensive biosensing methods and techniques discussed herein will continue to develop more sophistication over time. The field of orthopedic surgery and post-operative care (and monitoring) has not so far benefited from PI-POCT diagnostic methods. In the discussion below various representative embodiments outline some concepts of PI-POCT diagnostics that may be utilized in orthopedic surgery and post-operative care.

Press Fit Measurement in Orthopedic Arthroplasty

As noted herein, aseptic loosening is a major cause of failure of cement-less arthroplasty. An embodiment of the present invention may make use of implantable sensors on prosthesis, to be utilized at the prosthesis/bone interface, specifically as a PI-POCT device, to provide real-time information about a quality of the interference fit of the implant into its implant location, both during installation and after implant installation. Implant PI-POCT may be accomplished with (i) pressure and force sensors; and/or (ii) distance, proximity and displacement sensors. Once an appropriate interference fit of any particular prosthesis/bone interface is determined through in vivo and in vitro studies, a calibration curve can be produced to determine how much force, pressure, distance, and displacement is necessary to obtain appropriate and optimal press fit. A biosensor, suitably positioned for permanent implantation on the surface of a prosthesis, to be engaged at a prosthesis/bone interface can provide necessary data (i.e., force and/or displacement measurement) in real-time fashion. In this way the surgeon will know immediately as to whether appropriate (optimal) interference fit fixation has been obtain at the time of implantation, and may be used for subsequent post-operative evaluation.

Figure 40:
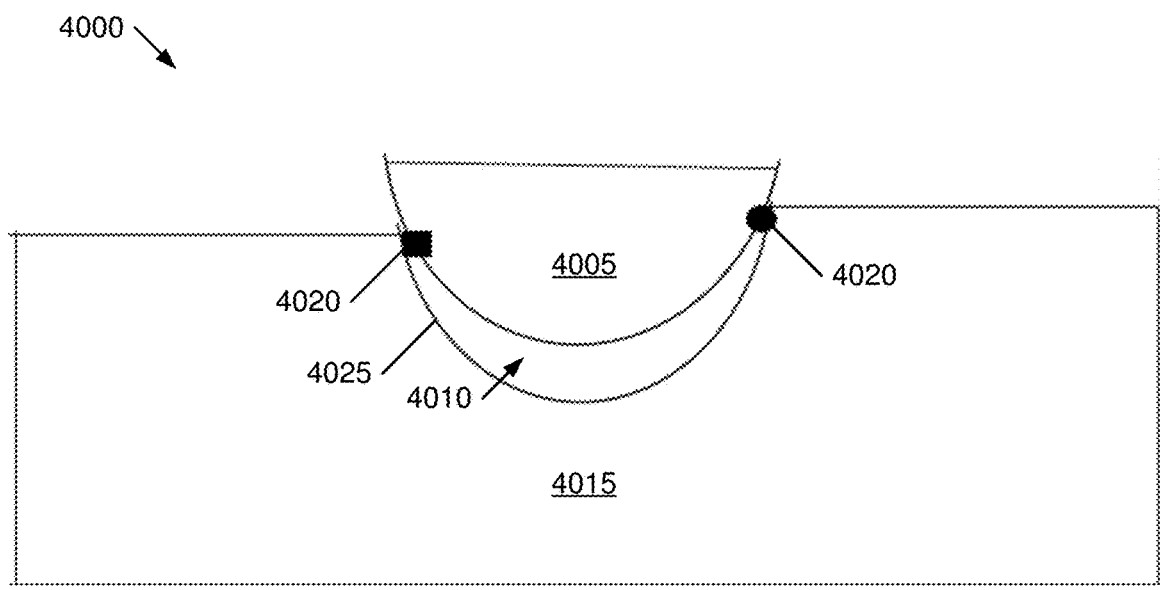

FIG. 40 illustrates an implementation of force/displacement sensing embodiment 4000 with interference fit fixation for installation of an implant 4005 into a prepared cavity 4010 in a portion of bone 4015. One or more biosensors 4020 may be installed on implant 4005 and/or at an bone/implant interface 4025. Biosensor 4020 may include a force and/or displacement transducer.

Aseptic Loosening in Orthopedic Arthroplasty

An electromechanical biosensor incorporated within a prosthesis surface at an anticipated junction of the prosthesis/bone interface can provide information regarding a loose prosthesis that is experiencing micromotion greater than 50 to 150 m. Motion detectors such as Linear Variable Displacement Transformers LVDT applied permanently at this bone/implant interface may provide immediate PI-POCT diagnostics of a loose prosthesis.

Figure 41:
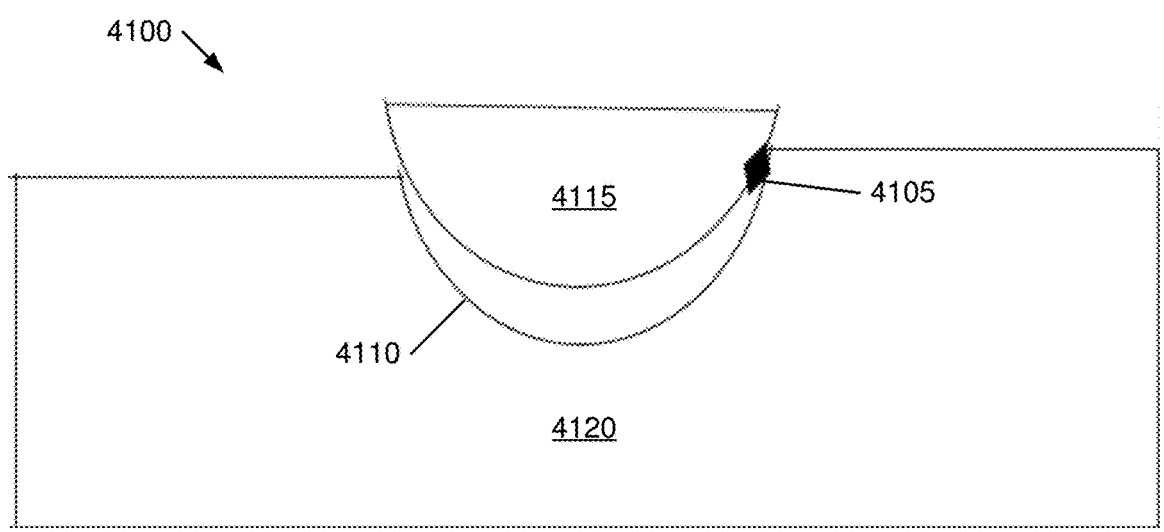

FIG. 41 illustrates an implementation of an aseptic loosening sensing embodiment 4100, including a biosensor 4105 having an LVDT transducer, disposed at an interface 4110 of an implant 4115 and a portion of bone 4120, implant 4115 installed an interference fit fixation.

Infection in Orthopedic Arthroplasty

Infection of prosthesis with micro-organisms produces a variety of metabolic and electrochemical byproducts including pH, plons, $O_2$, production of electrical currents and optical signals, as well as metabolites associated with specific infections. Common examples of substrates used to assess an infectious process include leukocyte estrace, alpha-defensing, nitrates, white blood cells, inflammatory debris to name a few. Given the advancement in biosensor technology and in particular its fusion with nanotechnology and integrated chips, it is advantageous to construct biosensors in the nanoscale with bioreceptors and transduction mechanisms that are highly specific to infectious processes. Any of the metabolites discussed above can be chosen as analytes to be detected. Bioreceptors (enzymes, antibodies, DNA, aptamers etc.) for detection the chosen analyte can be chosen and immobilized to transduction elements (capacitors, electrodes, transistors, FET, etc.), which are incorporated in integrated electronic chips with the capacity to transfer information wirelessly for interpretation and display.

In addition to monitoring the metabolites associated with infections, biosensor chip technology can directly measure the concentration of microorganisms. For example, Complementary Metal Oxide Semiconductor (CMOS) based integrated microelectrodes can be used to monitor growth of specific bacterial pathogens, such as methicillin resistant *Staphylococcus*, which are of particular interest in orthopedics.

Figure 42:
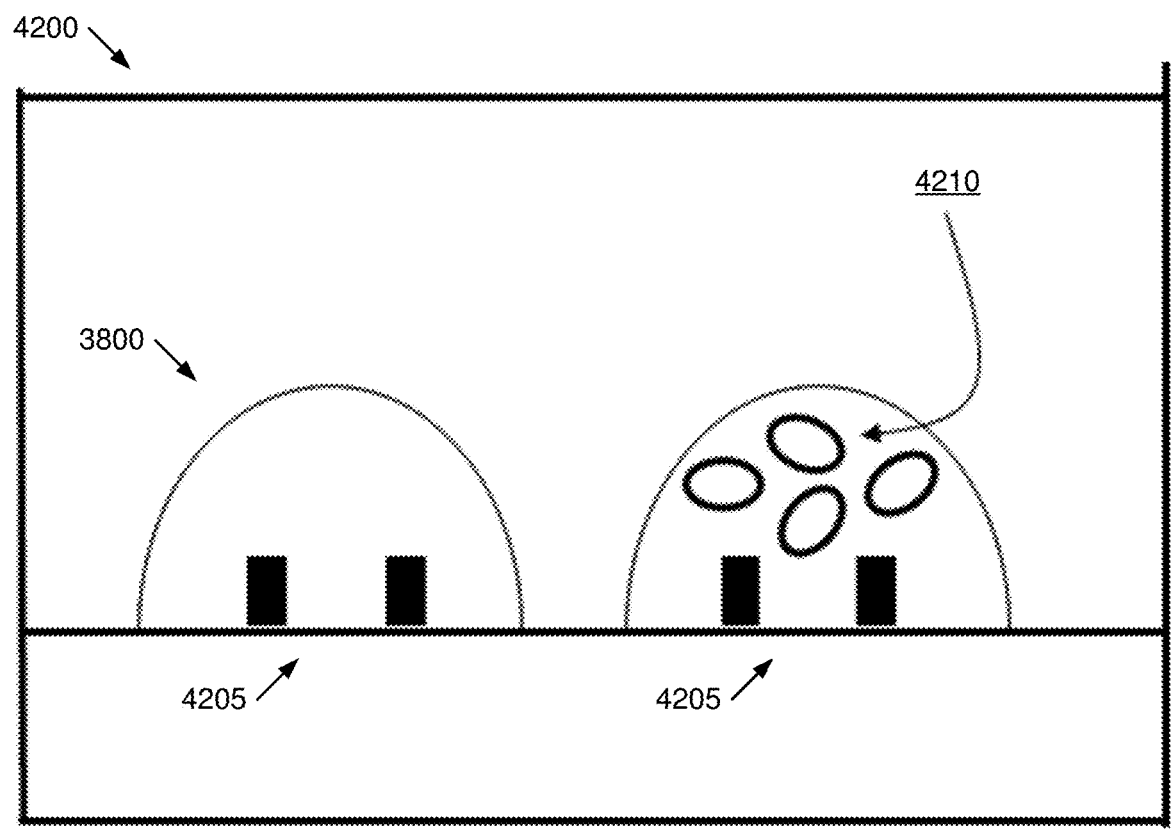

FIG. 42 illustrates a biosensor integrated microelectronic biosensor 4200 implemented in a CMOS package. Biosensor 4200 includes a set of electrodes 4205 for detection of one or more pathogens, such as bacteria 4210.

Metallosis and Trunnionosis in Orthopedic Arthroplasty

A presence of metallic debris in orthopedics is caused by micromotion between modular prosthesis. High concentrations of metal ion debris such as cobalt, chromium, titanium in the joint fluid and surrounding soft tissues occur as a result of poor interference fit between modular components. Metallosis can be a significant, and up to now, unrecognized source of inflammatory debris which can secondarily lead to loosening and infection. The current diagnostic methods for evaluation of metallosis and trunnionosis and are complex and indirect and generally result in poor yields in the early stages of the condition. The bio sensor technology noted herein may be incorporated and adapted for a PI-POCT device for detection of, immediate, and early diagnosis of metallosis and associated conditions such as Adverse Local Soft Tissue Reactions ALTR and metal toxicity. The biosensors are placed within a prosthesis or in the vicinity of the prosthesis directly embedded in bone. The analyte to be examined would be ion debris such as Cobalt, Chromium or Titanium. A variety of bioreceptors can be chosen to recognize the ion debris and proper transduction mechanisms can convert the biorecognition of metal debris into an electrical or optical signal which is wirelessly transferred for interpretation and display.

A concept of PI-POCT biosensor diagnostics for infectious conditions and metallosis in orthopedics (PI-POCT-IMO) may be included in an embodiment of the present invention, and may provide structures and methods to quickly, accurately and with high degree of specificity and sensitivity (purely evidenced based) confirm or rule out these conditions, at the same time eliminating or reducing a need for multiple expensive tests and overreliance on surgeon judgement, which frequently leads to late diagnosis and damage to the patient.

Figure 43:
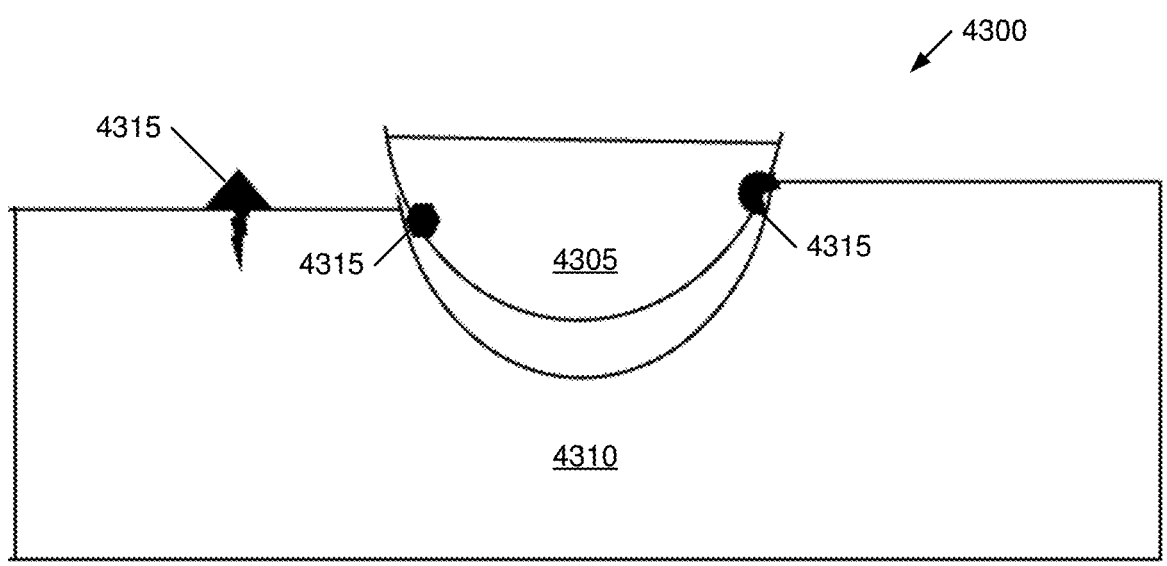

FIG. 43 illustrates a biosensing system 4300 for assessing metallosis and trunnionosis including at or near an implant 4305 installed into a portion of bone 4310. One or more biosensors 4315 for biosensing of metal debris (e.g., cobalt, chromium, and titanium) in or around implant 4305.

Optimal Press Fit in Ligament Reconstruction

Embodiments described herein may make use of permanent wireless implantable biosensors for orthopedic arthroplasty. In US patent application CONNECTIVE TISSUE GRAFTING, U.S. Application No. 62/742,851 filed 8 Oct. 2018 and CONNECTIVE TISSUE GRAFTING, U.S. Application No. 62/743,042 filed 9 Oct. 2018, both applications are hereby expressly incorporated by reference thereto in their entireties for all purposes, embodiments were described that make use of biosensors for assessment of tension, torsion and shear force of the reconstructed ligaments.

Electromechanical biosensors can be utilized at a reconstructed ligament/bone interface, in much the same manner which was described in press fit arthroplasty embodiments described herein, to assess a pressure (force) and interference fit (displacement) at this ligament/bone junction, to assure proper and optimal interference fit is obtained at the time of implantation. Increased interfacial pressures between graft and tunnel may lead to direct type healing which is preferred over indirect type healing.

Figure 44:
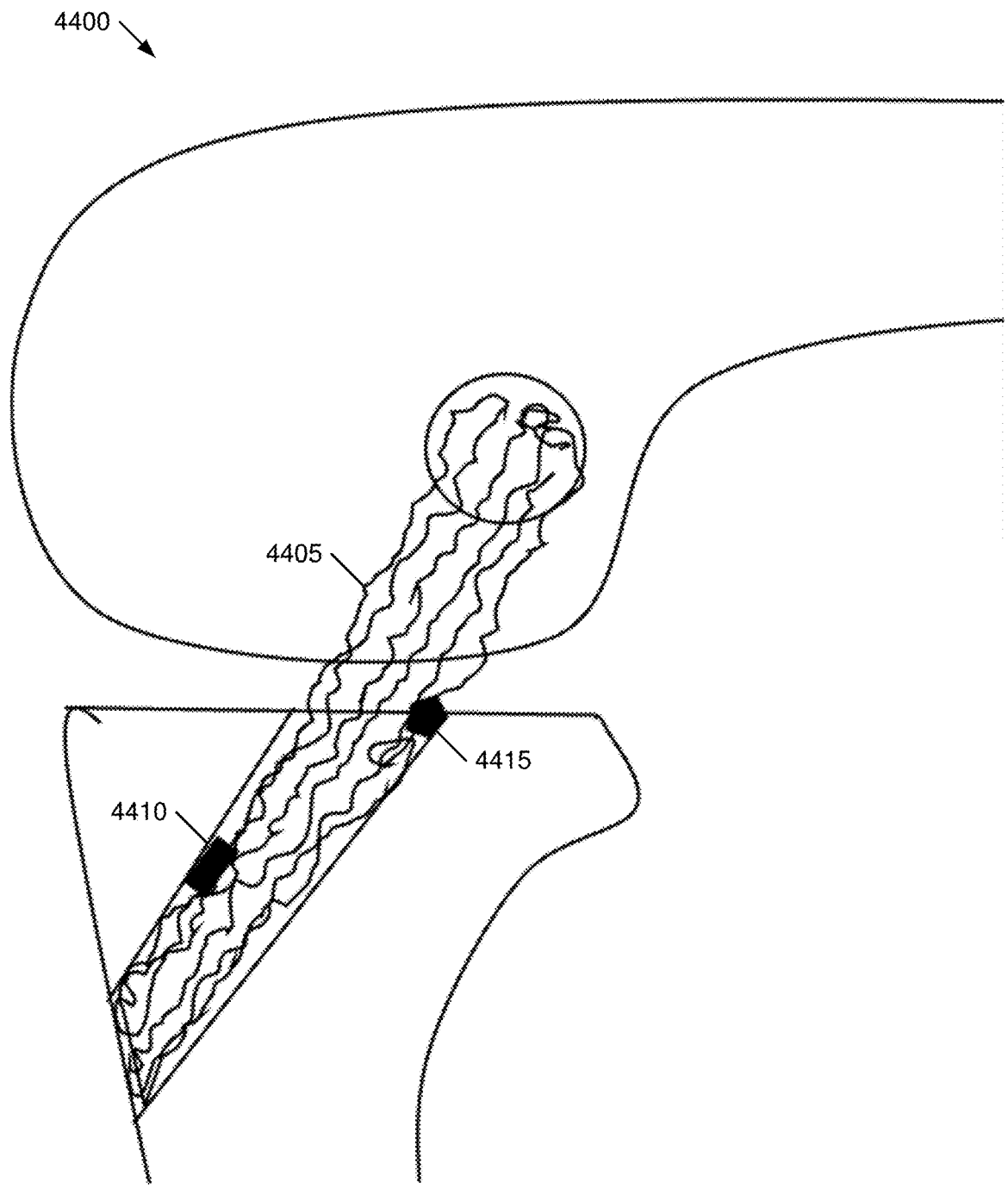

FIG. 44 illustrates a sensing system 4400 for assessing optimal press fit in ligament reconstruction. An installed reconstructed ligament 4405 may include one or more of a displacement biosensor 4410 and/or a force biosensor 4415.

Poor Healing of Reconstructed Ligaments to Bone Assessment

Biosensors with displacement sensors such as LVDT can assess loosening and poor adhesion of the ligament graft to bone at the ligament/bone interface by measuring excessive micromotion at the ligament bone interface.

Figure 45:
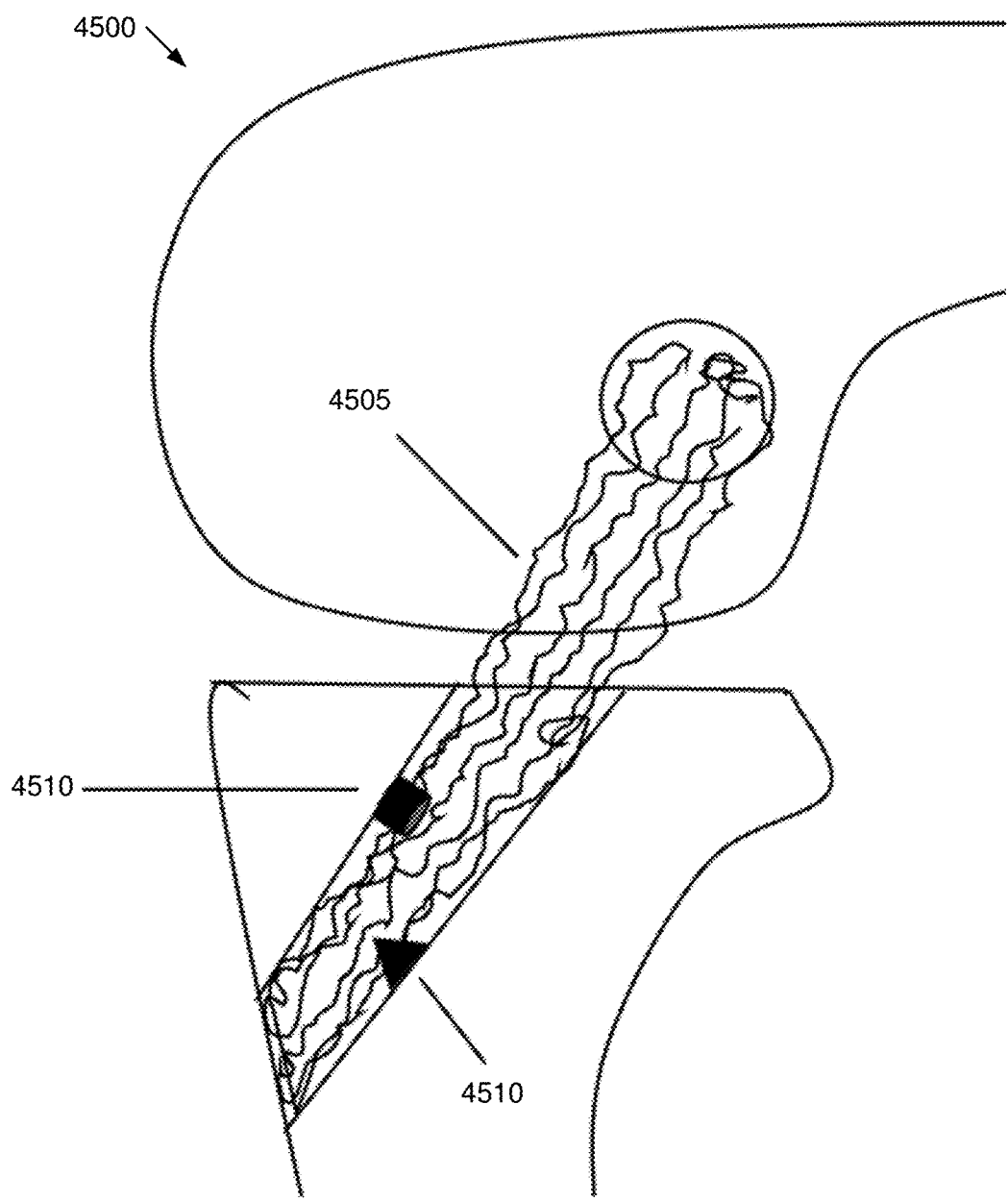

FIG. 45 illustrates a sensing system 4500 for assessing poor healing of a reconstructed ligament 4505. Installed reconstructed ligament 4505, or a ligament/bone interface, may include one or more biosensors 4510 including an LVDT transducer.

Failure Mode Assessment of Reconstructed Ligament Grafts with PI-POCT Biosensors Electrochemical biosensors can also be used in the body of the ligament or at the tendon bone junction to evaluate a nature of damaging forces that may ultimately lead to failure of the ligament graft, which may include tension, torsion and or shear forces.

Figure 46:
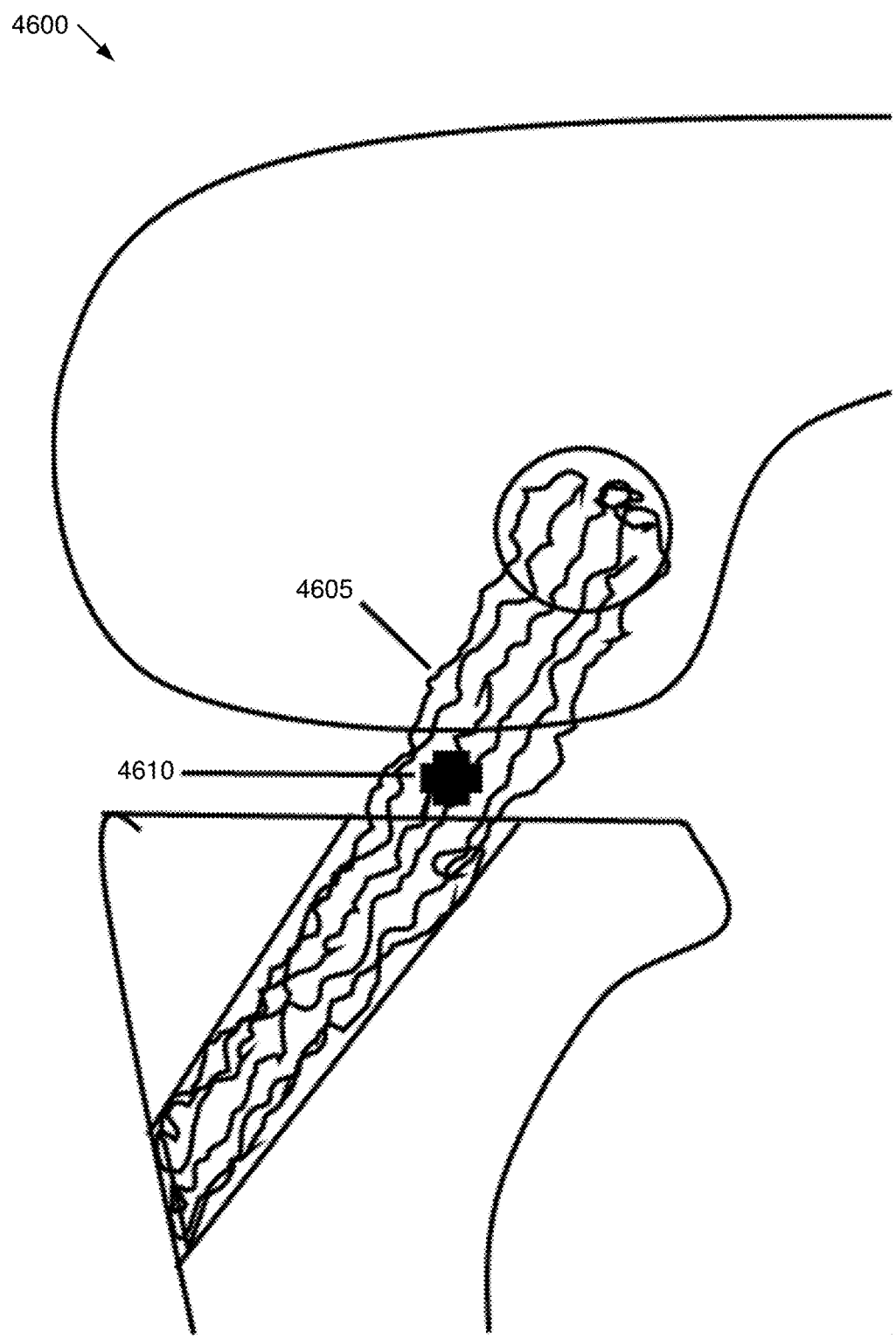

FIG. 46 illustrates a sensing system 4600 for assessing various failure modes of a reconstructed ligament graft 4605. A biosensor 4610 may include one or more of a tension, shear, torsion, and/or displacement transducer.

In a case where a graft has failed before embarking on revision surgery. Certain causes of failure are easier to diagnose such as tunnel mal-positioning with the help of radiographic techniques such as X-ray and MRI studies. However, many times failures occur even with perfect tunnel placement. Frequently, in these scenarios the source of failure remains unknown. Repeat high force traumatic injury is one possibility and more likely in contact sports. Poor graft incorporation and healing is another possible source of failure. These scenarios can be sharply distinguished and clearly diagnosed with PI-POCT orthopedic monitoring of graft reconstructions. For example, if a graft does not heal and becomes loose over a period of 12 months (typical healing phase of an ACL graft), LVDT type biosensors employed at the time of graft implantation as PI-POCT systems may convey the information to the surgeon through wireless transmission during routine clinic visits. Alternatively, if a major traumatic event causes the rupture of a graft, a force biosensor implanted within the body of the ligament or at the ligament/bone junction may reveal the exact mechanism of injury by conveying the specific forces (tension, torsion, shear or combination thereof) involved in the ligament rupture.

The concept of post-operative monitoring of Prosthetic Interface Point of Care Testing PI-POCT naturally leads to the concept of Prophylactic Monitering Point of Care Testing PM-POCT.

Traumatic and repetitive stress injuries in professional and recreational athletic population is very common.

Generally speaking traumatic high velocity injuries particularly in professional and collegiate athletes are more likely to be witnessed revealing the source and mechanism of injury. However, higher level understanding of these traumatic injuries can further be garnered with the use of PM-POCT devices applied to the tendons, bones and ligaments of high-level athletes to evaluate in real time the repetitive and traumatic stresses which produced a tear, rupture or failure of tissues. This ability can pin point certain biomechanical weaknesses in the athletes body (ligament, tendon, bone, muscle function and tightness) that can be addressed acutely in order to decrease the chance of major career ending injuries. In addition, gaining knowledge and the ability to accumulate data base on specific mechanisms of injury, through direct PM-POCT observation of the forces (tensile, compressive, torsional and shear or combination) involved in tissue failure, provides a level of understanding that has not been previously available. This can lead to development of better training techniques and protective orthotics for high level athletes.

Repetitive stress injuries, on the other hand are generally multifactorial, nonetheless frequently related to poor body mechanics. These include stress fractures of the lower extremity (i.e. tibia, metatarsals, calcaneus) and tendinitis problems (i.e. achilleas tendinitis and plantar fasciitis) and peripheral neuropathies (Morton's neuroma and tarsal tunnel syndrome).

As an example, poor body mechanics such as tight hip flexors and hamstrings in the proximal joints (hips) can constrain the range of motion of the lower extremity joints including hip, knee, ankle and feet, leading to stress fractures and/or tendinitis in the distal joints.

Figure 47:
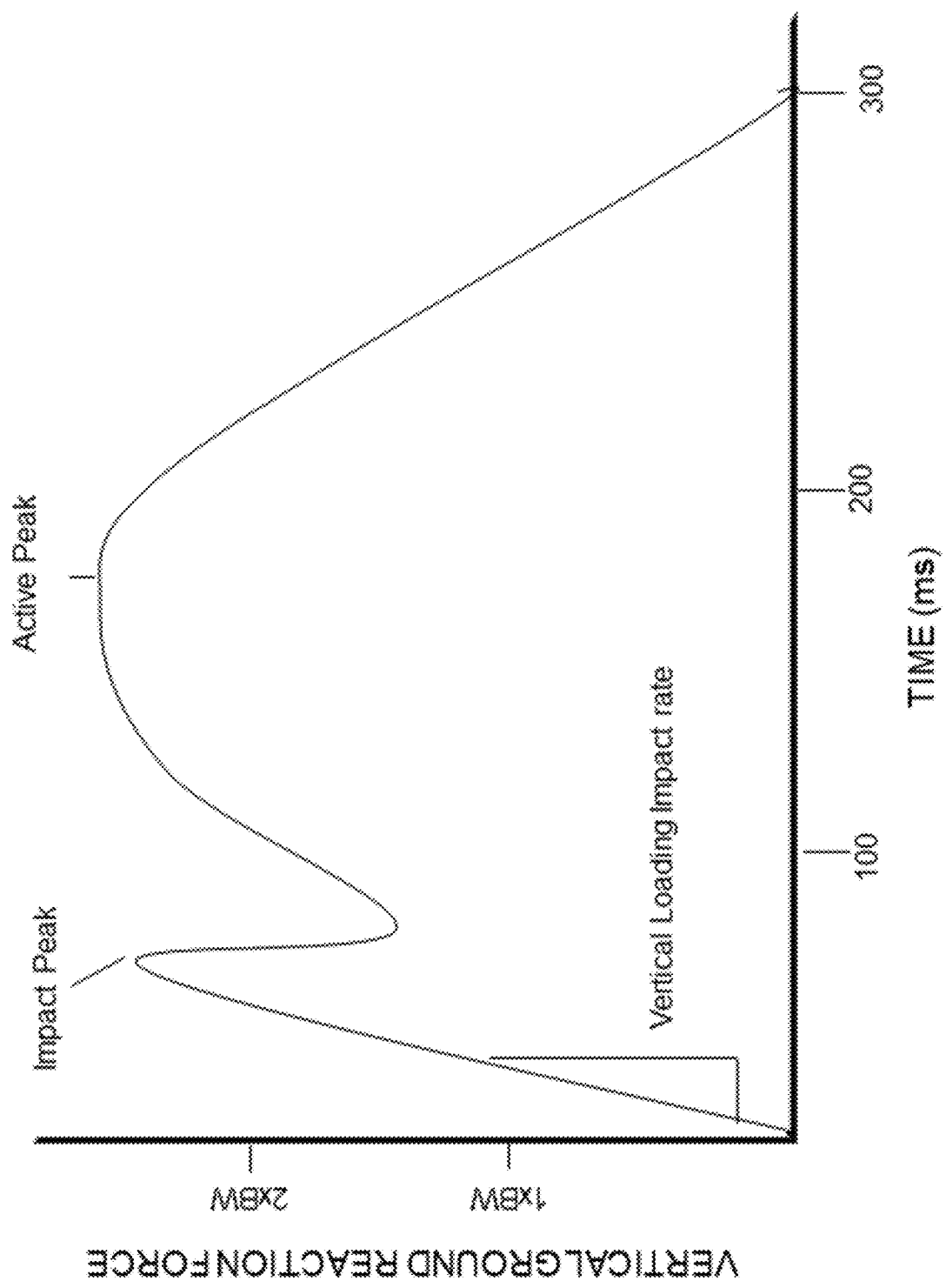
FIG. 47 illustrates a first gait reaction force over time for a step.

During gait cycle every time the foot lands on the ground the foot impacts the ground with certain amount of force which is countered by an equal and opposite amount of force applied by the ground to the foot called the ground reaction force GRF. The GRF has several components depending on the axis of movement being evaluated (including the x, y, and z axis). In the y axis or vertical GRF (straight up and down) motion, the foot experiences different stresses depending on whether the person strikes the ground initially with the hind foot or forefoot. A sample of the vertical GRF for a heel striker is illustrated in FIG. 47.

The Y axis is represented by body weight. The X axis is represented by milliseconds. The amount of time each foot is in contact with the ground varies for different runners but 300 ms is an average amount for a recreational runner. For a heel striker there are two distinct impacts. The impact peak which represents the initial force applied by the ground to the foot at the time of initial heel contact. The active peak which is a function of the force experienced by the foot during midstance. The slope of the impact peak (rise over run) is called vertical loading rate. The vertical loading rate represents how quickly the impact force is applied. A rapid sharp impact peak represents a large vertical load spread over a short time period. A gentler slope of indicates that the force being felt on the heel is being "diffused" or "spread" over a longer period of time.

Figure 48:
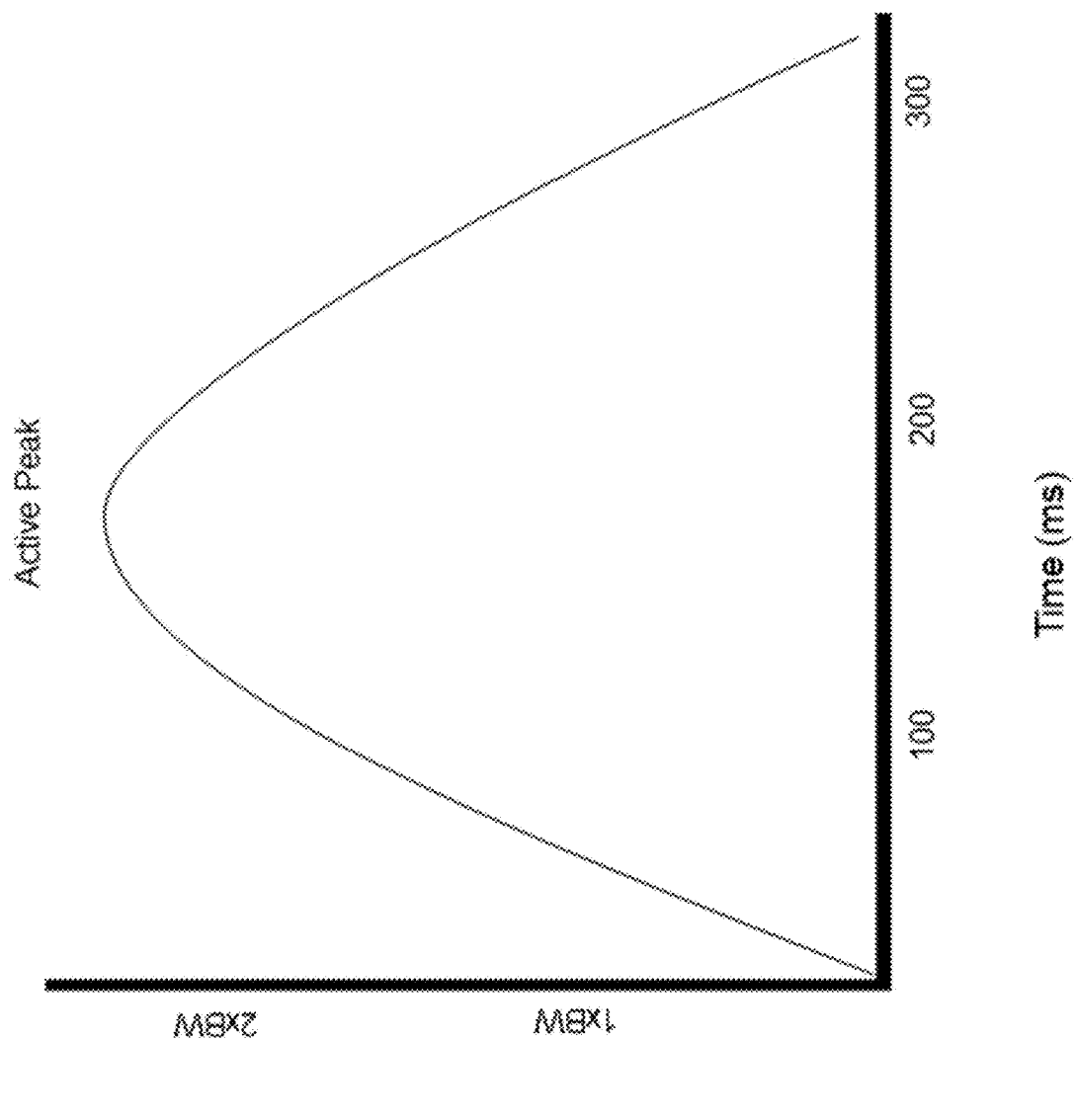
FIG. 48 illustrates a second gait reaction force over time for a step.

Forefoot runners, in contrast, do not have a large or significant impact peaks, illustrated in a gait chart in FIG. 48.

By eliminating the heel strike the forefoot runner has eliminated the impact peak, and the initial slope of the vertical loading rate is lower (smaller slope). The main reason for this transition is that the forefoot runner, now instead of directly impacting on the heel, has started to use the elaborate mechanical properties of the (foot/ankle) that allow absorption and release of energy and (i.e., an interplay of the arch of the foot, plantar fascia, achilleas tendon and gastric soleus muscle) to cushion the blow on the ground. The foot and ankle can collectively work as a very sophisticated shock absorber to absorb and store kinetic energy in the joints and muscles (during impact) and through and elaborate unwinding of the joints and windlass mechanism release the energy (during propulsion).

Therefore, when a runner runs with a very prominent heel strike, the natural shock absorbing mechanisms of the foot and ankle are not utilized, which leads to a "stiff system" with no compliance. This subsequently leads to increased stresses being transferred to the proximal bones and joints, which is one of the many mechanisms that leads to development of stress fractures, such ones in the tibia and calcaneus; as well as aggravation of the knee joint and development of tendon partial tears and tendinitis, such as achilleas tendinitis and plantar fasciitis.

The ability to apply, through small incisions or percutaneously, small biosensors within tendons, bones, and ligaments provides the possibility of Prophylactic Monitoring Point of Care Testing in orthopedics (PM-POCT).

It is well known that when patients generally present with early signs of tendinitis and stress fractures, that the X-rays and MRIs are typically negative and frequently provide minimal diagnostic value. The patient has a painful joint, bone or tendon (particularly with activity) and the studies are all negative. The physician typically has to make a "clinical diagnosis" of, for example, tendinitis but has no means of measuring the extent of this condition. A qualitative assessment based on experience is made. Currently there is no test that is sensitive and specific enough to diagnose or quantify "repetitive stress injuries" in the field of orthopedics.

Similar problems have arisen in repetitive stress injuries at work. In the day and age of computer science, time spent on computers and monitors has led to a significant number of upper extremity repetitive stress injuries, including tendinitis and peripheral neuropathies such as carpal tunnel syndrome and lateral epicondylitis. This has led to loss of productivity for society as well as pain and suffering for patients. There is no current method to diagnose or quantify these "work related" repetitive stress injuries at an early stage, and unfortunately, many of these patients are written off as malingerers.

PM-POCT provides the capability to apply biosensors within tendons, ligaments, and bone in order to monitor the amount of stress, micromotion, and inflammatory metabolites that typically accompany repetitive stress injuries. This capability can provide a means for early detection and correction of certain motions, positions and ergonomics that lead to these attritional injuries. The ability to collect precise data about repetitive stress injuries produces the ability to develop a database, that can be utilized to abstract formulas, algorithms and recommendations for prevention of these injuries. As well, the ability to store accumulated point of care POC information in large data bases, in combination with software development, can lead to the creation of derivative recommendations through machine learning and Artificial intelligence for injury prevention.

In the example of the heel striking runner discussed above, a biosensor applied to the calcaneus, tibia, plantar fascia, Achilleas tendon and the tarsometatarsal ligaments of the foot, with ability to measure force (loading), displacement (LVDT sensor), directionality (IMU inertial measuring units), and inflammatory metabolites (i.e., mast cells, macrophages, cytokines, chemokines, histamine, and the like) can not only detect whether microtears and inflammation are actually occurring through the (PM-POCT) process, but also determine WHY they are occurring.

In the example note above, the heel strike runner with very tight hamstring, adductor (groin muscle) and hip flexors (iliopsoas) will have a very short gait pattern (or stride length) without the ability to full flex and extend the hips producing less forward propulsion in the horizontal direction and more upward and downward motion leading to large vertical ground reaction forces GRF, and large vertical loading rate. This alteration in mechanics can clearly lead to a stress fracture of the calcaneus or tibia (and/or damage to the knee joints) for example. Similarly, any imbalance in the biomechanical function of the lower extremity musculotendinous system (typically tight and contracted muscle units) can lead to excessive loading (over repeated cycles) of certain bone and joints causing microtears, tendinitis, stress fractures and other repetitive stress injuries.

The ability to know this information through the PM-POCT process allows clinicians to make proper adjustments by focusing on the systems that are primarily responsible for causing the injury. For example, if the PM-POCT data reveal a correlation between lack of hip extension (tight iliopsoas) and excessive vertical loading rate and large impact peaks in a heel strike runner, emphasis on stretching of the hip flexors will be prescribed to decrease the chance of developing calcaneal and tibial stress fractures. Stretching of the hip flexors may be overemphasized over stretching of the adductor (groin) muscles and or other muscle groups such as the quadriceps or the Iliotibial band, particularly if these muscle groups are not excessively tight or contracted.

PM-POCT therefore allows insight to orthopedic and sports and work related repetitive stress injuries, through point of care testing, that was heretofore not conceivable and/or possible. This new capability allows early diagnosis and intervention of repetitive stress injuries, as well as a means for production of databases that can be exploited for better understanding of the musculoskeletal system mechanics and injuries through machine learning and Artificial Intelligence.

Figure 49:
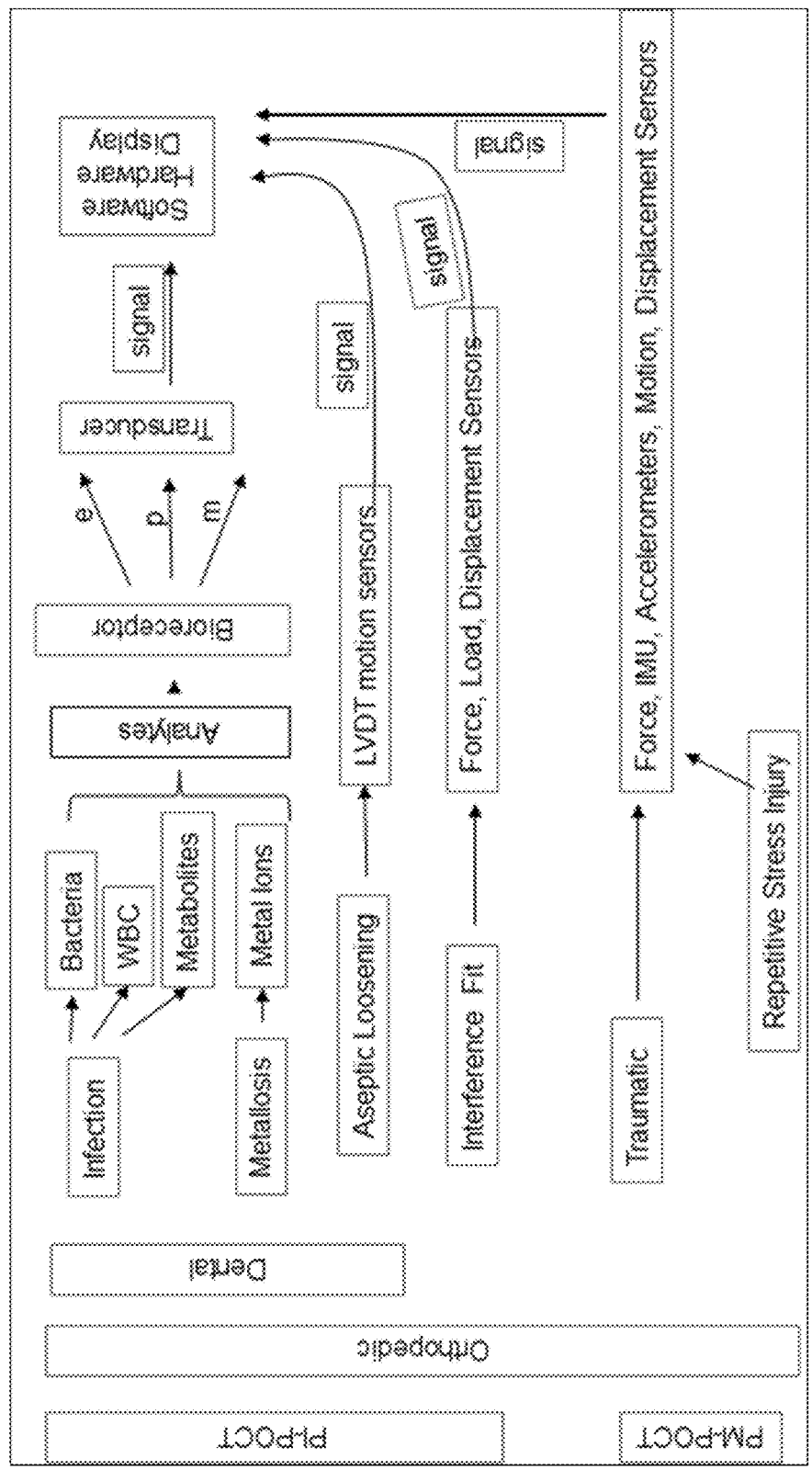
FIG. 49 illustrates a biologic sensing architecture.

FIG. 49 illustrates a comprehensive diagram of point of care testing in orthopedic and dental surgery where PI-POCT and PM-POCT combine to provide real-time data from the immediate site of care for intra-operative decision making and post-operative monitoring of diseases, injuries, infections and implant failures.

Infection or Graft Rejection Assessment with PI-POCT Biosensors.

Similarly, to the embodiments described herein, embedded and implantable biosensors my be designed to detect infectious processes in arthroplasty for determination of infections processes in ligament reconstruction (i.e., ACL grafts) by measuring the infectious organisms directly or measuring the metabolic byproducts of the infectious condition.

The following references, expressly incorporated by reference hereto in their entireties for all purposes, support one or more of the concepts or ideas presented herein, including: 1) Udomkiat P, Dorr L D, Wan Z. Cementless hemispheric porous-coated sockets implanted with press—fit technique without screws: average ten-year follow-up. J Bone Joint Surg. 2002; 84A:1195.; 2) Takedani H, Whiteside L A, White S E, et al. The effect of screws and pegs on cementless acetabular fixation. Trans Orthop Res Soc 1991; 16:523; 3) lAhnfelt, L., P. Herberts, H. Malchau, and G. Andersson. Prognosis of total hip replacement: a swedish multicenter study of 4664 revisions. Acta Orthop. Scand. 61:2-26, 1990; 4) Corbett, K. L., E. Losina, A. A. Nti, J. J. Prokopetz, and J. N. Katz. Population-based rates of revision of primary total hip arthroplasty: a systematic review. PLoS ONE 5:e13520, 2010; 5) Huiskes, R. Failed innovation in total hip replacement: diagnosis and proposals for a cure. Acta Orthop. Scand. 64:699-716, 1993; 6) Harris, W. Aseptic loosening in total hip arthroplasty secondary to osteolysis induced by wear debris from titanium—alloy modular femoral heads. JBJS. 73:470-472, 1991; 7) Kobayashi, S., K. Takaoka, N. Saito, and K. Hisa. Factors affecting aseptic failure of fixation after primary charnley total hip arthroplasty multivariate survival analysis. JBJS. 79:1618-1627, 1997; 8) Lombardi Jr, A. V., T. Mallory, B. Vaughn, and P. Drouillard. Aseptic loosening in total hip arthroplasty secondary to osteolysis induced by wear debris from titanium-alloy modular femoral heads. JBJS. 71:1337-1342, 1989; 9) Huiskes, R. Failed innovation in total hip replacement: diagnosis and proposals for a cure. Acta Orthop. Scand. 64:699-716, 1993; 10) Clohisy, J. C., G. Calvert, F. Tull, D. McDonald, and W. J. Maloney. Reasons for revision hip surgery: a retrospective review. Clin. Orthop. Relat. Res. 429:188-192, 2004; 11) Kim, Y. S., J. J. Callaghan, P. B. Ahn, and T. D. Brown. Fracture of the acetabulum during insertion of an oversized hemispherical component. JBJS. 77:111-117, 1995; 12) Sharkey, P. F., W. J. Hozack, J. J. Callaghan, Y. S. Kim, D. J. Berry, A. D. Hanssen, and D. G. LeWallen. Acetabular fracture associated with cementless acetabular component insertion: a report of 13 cases. J. Arthro-plast.14:426-431, 1999; 13) Weeden, S. H. and W. G. Paprosky. Minimal 11-year follow-up of extensively porous-coated stems in femoral revision total hip arthroplasty. J. Arthroplast. 17:134-137, 2002; 14) Ulrich A D, Seyler $T_M$, Bennett D, Celanois R E, Saleh K J, Thongtrangan I, Kuskowski M, Cheng E Y, Sharkey P F, Parvizi J, Stiehl J B, Mont M A. Total hip arthroplasties: What are the reasons for revision? International Orthopedics (SICOT) (2008) 32: 597-604; 15) Olory, B., E. Havet, A. Gabrion, J. Vernois, and P. Mertl. Comparative in vitro assessment of the primary stability of cementless press-fit acetabular cups. Acta Orthop. Belg. 70:31-37, 2004; 16) Meneghini, R. M., C. Meyer, C. A. Buckley, A. D. Hanssen, and D. G. Lewallen. Mechanical stability of novel highly porous metal acetabular components in revision total hip arthroplasty. J. Arthroplast. 25:337-341, 2010; 17) Fehring, K. A., J. R. Owen, A. A. Kurdin, J. S. Wayne, and W. A. Jiranek. Initial stability of press-fit acetabular components under rotational forces. J. Arthroplast 29:1038-1042, 2014; 18) Georgiou, A., and J. Cunningham. Accurate diagnosis of hip prosthesis loosening using a vibrational technique. Clin. Biomech. 16:315-323, 2001; 19) Balch C M, Freischlag J A, Shanafelt T, Stress and Burnout Among Surgeons. ARCH SURG/VOL 144 (NO. 4) April 2009; 20) Shanafelt T D, Balch C M, Bechamps G J, Tussell T, Dyrbye L, Satele D, Collicott P, Novotny P J, Sloan J, Freischlang J A Burnout and Career Satisfaction Among American Surgeons Ann Surg 2009; 250: 107-115; 21) Ulrich A D, Seyler $T_M$, Bennett D, Celanois R E, Saleh K J, Thongtrangan I, Kuskowski M, Cheng E Y, Sharkey P F, Parvizi J, Stiehl J B, Mont M A. Total hip arthroplasties: What are the reasons for revision? International Orthopedics (SICOT) (2008) 32: 597-604; 22) Kurtz S, Ong K, Lau E, Mowat F, Halpern M, Projections of Primary and Revision Hip and Knee Arthroplasty in the United States from 2005 to 2030 JBJS (2007) Am 89: 780-785; 23) Nakasone S, Takao M, Nishii T, Sugano N, Incidence and Natural Course of Initial Polar Gaps in Birmingham Hip Resurfacing Cups. J of Arthroplasty Vol 27, (9) 1676-1682; and 24) Springer B D, Griffin W L, Fehring T K, Suarez J, Odum S, Thompson C Incomplete Seating of Press-Fit porous Coated Acetabular Components (2008) J of Arthroplasty Vol 23 (6) 121-126.

The system and methods above has been described in general terms as an aid to understanding details of preferred embodiments of the present invention. In the description herein, numerous specific details are provided, such as examples of components and/or methods, to provide a thorough understanding of embodiments of the present invention. Some features and benefits of the present invention are realized in such modes and are not required in every case. One skilled in the relevant art will recognize, however, that an embodiment of the invention can be practiced without one or more of the specific details, or with other apparatus, systems, assemblies, methods, components, materials, parts, and/or the like. In other instances, well-known structures, materials, or operations are not specifically shown or described in detail to avoid obscuring aspects of embodiments of the present invention.

Reference throughout this specification to "one embodiment", "an embodiment", or "a specific embodiment" means that a particular feature, structure, or characteristic described in connection with the embodiment is included in at least one embodiment of the present invention and not necessarily in all embodiments. Thus, respective appearances of the phrases "in one embodiment", "in an embodiment", or "in a specific embodiment" in various places throughout this specification are not necessarily referring to the same embodiment. Furthermore, the particular features, structures, or characteristics of any specific embodiment of the present invention may be combined in any suitable manner with one or more other embodiments. It is to be understood that other variations and modifications of the embodiments of the present invention described and illustrated herein are possible in light of the teachings herein and are to be considered as part of the spirit and scope of the present invention.

It will also be appreciated that one or more of the elements depicted in the drawings/figures can also be implemented in a more separated or integrated manner, or even removed or rendered as inoperable in certain cases, as is useful in accordance with a particular application.

Additionally, any signal arrows in the drawings/Figures should be considered only as exemplary, and not limiting, unless otherwise specifically noted. Combinations of components or steps will also be considered as being noted, where terminology is foreseen as rendering the ability to separate or combine is unclear.

The foregoing description of illustrated embodiments of the present invention, including what is described in the Abstract, is not intended to be exhaustive or to limit the invention to the precise forms disclosed herein. While specific embodiments of, and examples for, the invention are described herein for illustrative purposes only, various equivalent modifications are possible within the spirit and scope of the present invention, as those skilled in the relevant art will recognize and appreciate. As indicated, these modifications may be made to the present invention in light of the foregoing description of illustrated embodiments of the present invention and are to be included within the spirit and scope of the present invention.

Thus, while the present invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the present invention. It is intended that the invention not be limited to the particular terms used in following claims and/or to the particular embodiment disclosed as the best mode contemplated for carrying out this invention, but that the invention will include any and all embodiments and equivalents falling within the scope of the appended claims. Thus, the scope of the invention is to be determined solely by the appended claims.

What is claimed as new and desired to be protected by Letters Patent of the United States is:

1. An acetabular cup for a prepared cavity in a portion of bone, comprising:
   an exterior shell portion defining a generally hemispherical interior cavity; and
   said generally hemispherical exterior shell further includes a set of sensors; and
   wherein each said sensor of said set of sensors each include a bioreceptor and a transducer communicated to said bioreceptor;
   wherein each said bioreceptor is configured to produce a recognition event upon a recognition of a target analyte; and
   wherein each said transducer is configured, responsive to said recognition event, to produce a recognition signal.

2. The acetabular cup of claim 1 wherein one or more of said sensors of said set of sensors are selected from the group consisting of a general sensor, a biologic sensor, a mechanical sensor, and combinations thereof.

3. The acetabular cup of claim 1 wherein said set of sensors include a set of bioreceptors immobilized on transducers configured to bio-recognize one or more of bacteria, white blood cells, and variety of a set of byproduct metabolites produced as a result of one or more of an infectious process, an accumulation of metal debris, an accumulation of implant debris, or an accumulation of polymer debris as analytes.

4. The acetabular cup of claim 3 wherein said biorecognition includes a biorecognition event and wherein said set of biorecptors transduce said biorecognition event into a signal configured for one or more of a measurement, quantification, and processing of diagnostic information.

5. The acetabular cup of claim 1 wherein said set of sensors include one or more wireless biological electronic sensors.

6. The acetabular cup of claim 1 wherein said set of sensors include one or more mechanical and biomechanical sensors as motion and linear displacement detectors.

7. The acetabular cup of claim 1 wherein said set of sensors include one or more force, load and displacement sensors directly at an implant/bone interface.

8. The acetabular cup of claim 1 wherein each said sensor of said set of sensors are configured for a continuous monitoring of said target analyte.

9. The acetabular cup of claim 1 wherein said target analyte includes a predetermined in situ substance producing said recognition event in said associated bioreceptor.

10. The acetabular cup of claim 9 wherein said recognition signal is produced, responsive to said recognition event, without receipt of a recognition signal.

11. An implant configured for an association with a portion of bone, comprising: a structure configured for an engagement with the portion of bone; and a set of sensors integrated with said structure; and wherein each said sensor of said set of sensors each include a bioreceptor and a transducer communicated to said bioreceptor; wherein each said bioreceptor is configured to produce a recognition event upon a recognition of a target analyte; and wherein each said transducer is configured, responsive to said recognition event, to produce a recognition signal, wherein the portion of bone includes a prepared cavity, wherein the association includes an installation into said prepared cavity, and wherein said structure includes an acetabular cup configured for said installation.

12. The acetabular cup of claim 11 wherein each said sensor of said set of sensors are configured for a continuous monitoring of said target analyte.

13. The implant of claim 11 wherein said target analyte includes a predetermined in situ substance producing said recognition event in said associated bioreceptor.

14. The implant of claim 13 wherein said recognition signal is produced, responsive to said recognition event, without receipt of a recognition signal.

* * * * *